(12) United States Patent
Edwards et al.

(10) Patent No.: US 10,221,161 B2
(45) Date of Patent: Mar. 5, 2019

(54) INHIBITORS OF PLASMA KALLIKREIN

(71) Applicant: Kalvista Pharmaceuticals Limited, Salisbury (GB)

(72) Inventors: Hannah Joy Edwards, Salisbury (GB); David Michael Evans, Salisbury (GB); Premji Meghani, Nottingham (GB); Andrew Richard Novak, Nottingham (GB)

(73) Assignee: Kalvista Pharmaceuticals Limited, Salisbury, England (GB)

( * ) Notice: Subject to any disclaimer, the term of this patent is extended or adjusted under 35 U.S.C. 154(b) by 0 days.

(21) Appl. No.: 14/907,842

(22) PCT Filed: Aug. 14, 2014

(86) PCT No.: PCT/GB2014/052510
§ 371 (c)(1),
(2) Date: Jan. 27, 2016

(87) PCT Pub. No.: WO2015/022546
PCT Pub. Date: Feb. 19, 2015

(65) Prior Publication Data
US 2016/0168123 A1    Jun. 16, 2016

Related U.S. Application Data

(60) Provisional application No. 61/865,732, filed on Aug. 14, 2013, provisional application No. 61/865,756, filed on Aug. 14, 2013.

(51) Int. Cl.
| | |
|---|---|
| *C07D 401/14* | (2006.01) |
| *C07D 413/14* | (2006.01) |
| *C07D 401/10* | (2006.01) |
| *C07D 401/12* | (2006.01) |
| *C07D 403/10* | (2006.01) |
| *C07D 403/14* | (2006.01) |
| *C07D 417/14* | (2006.01) |
| *C07D 471/04* | (2006.01) |

(52) U.S. Cl.
CPC ......... *C07D 401/14* (2013.01); *C07D 401/10* (2013.01); *C07D 401/12* (2013.01); *C07D 403/10* (2013.01); *C07D 403/14* (2013.01); *C07D 413/14* (2013.01); *C07D 417/14* (2013.01); *C07D 471/04* (2013.01)

(58) Field of Classification Search
USPC ..................................................... 514/230.5
See application file for complete search history.

(56) References Cited

U.S. PATENT DOCUMENTS

| 5,187,157 A | 2/1993 | Kettner et al. |
|---|---|---|
| 2007/0254894 A1 | 11/2007 | Kane et al. |
| 2010/0113782 A1 | 5/2010 | Bolin et al. |
| 2011/0152533 A1 | 6/2011 | Sinha et al. |
| 2012/0298326 A1 | 11/2012 | Born |
| 2015/0315198 A1 | 11/2015 | Li et al. |

FOREIGN PATENT DOCUMENTS

| EA | 2012-00917 | 6/2011 |
|---|---|---|
| EP | 2281885 | 2/2011 |
| JP | 2010-520294 | 6/2010 |
| RU | 2485114 | 6/2013 |
| WO | WO 92/004371 | 3/1992 |
| WO | WO 94/029335 | 12/1994 |
| WO | WO 95/007921 | 3/1995 |
| WO | WO2003035076 A1 | 5/2003 |
| WO | WO 03/076458 | 9/2003 |
| WO | WO2004069792 A2 | 8/2004 |
| WO | WO2005079800 A1 | 9/2005 |
| WO | WO 2005/123680 | 12/2005 |
| WO | WO 2008/016883 | 2/2008 |
| WO | WO 2008/049595 | 5/2008 |
| WO | WO2008121670 A1 | 10/2008 |
| WO | WO2009083553 A1 | 7/2009 |
| WO | WO 2010/142801 | 12/2010 |
| WO | WO 2011/118672 | 9/2011 |

(Continued)

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802.*
A Simple, Sensitive and Selective Fluorogenic Assay to Monitor Plasma Kallikrein Inhibitory Activity of BCX4161 in Activated Plasma, BioCryst Pharmaceuticals, Inc., Journal of Allergy and Clinical Immunology, Feb. 2014, 133(2 Supp), Abstract AB40, p. 1.
"BCX4161, an Oral Kallikrein Inhibitor: Safety and Pharmacokinetic Results of a Phase 1 Study in Healthy Volunteers", BioCryst Pharmaceuticals, Inc., Journal of Allergy and Clinical Immunology, Feb. 2014, 133(2 Supp), Abstract AB39, p. 1.
Bhoola et al., "Bioregulation of Kinins: Kallikreins, Kininogens and Kinases", Pharmacological Rev., Mar. 1992, 44(1), 1-80.

(Continued)

Primary Examiner — Marcos L Sznaidman
(74) Attorney, Agent, or Firm — Baker & Hostetler LLP

(57) ABSTRACT

The present invention provides compounds of formula (I), compositions comprising such compounds; the use of such compounds in therapy (for example in the treatment or prevention of a disease or condition in which plasma kallikrein activity is implicated); and methods of treating patients with such compounds; wherein R5, R6, R7, R12, R13, A, L, B, n, W, X, Y and Z are as defined herein.

(I)

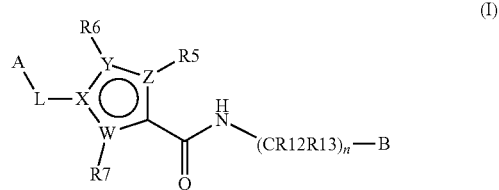

32 Claims, No Drawings

(56) References Cited

FOREIGN PATENT DOCUMENTS

| WO | WO 2012/004678 | 1/2012 |
| WO | WO 2012/017020 | 2/2012 |
| WO | WO 2012/142308 | 10/2012 |
| WO | WO 2013/111107 | 8/2013 |
| WO | WO 2013/111108 | 8/2013 |
| WO | WO2015103317 A1 | 7/2015 |
| WO | WO2015171526 A2 | 11/2015 |
| WO | WO2015171527 A1 | 11/2015 |
| WO | WO2016011209 A1 | 1/2016 |

OTHER PUBLICATIONS

Bryant et al., "Human Plasma Kallikrein-Kinin System: Physiological and Biochemical Parameters", Cardiovascular & Hematological Agents in Medicinal Chemistry, Jul. 2009, 234-250.

Caddick et al., "Convenient Synthesis of Protected Primary Amines From Nitriles", Tetrahedron Letters, Apr. 2000, 41, 3513-3516.

Campbell, "Towards Understanding the Kallikrein-Kinin System: Insights from the Measurement of Kinin Peptides", Brazilian Journal of Medical and Biological Research, Jun. 2000, 33(6), 665-677.

Chilcote et al., "ASP-634: An Oral Drug Candidate for Diabetic Macular Edema", ARVO, Mar. 2012, Presentation 2240, Abstract, p. 1.

Clermont et al., "Plasma Kallikrein Mediates Retinal Vascular Dysfunction and Induces Retinal Thickening in Diabetic Rats", Diabetes, May 2011, 60(5), 1590-1598.

Elman et al., "Randomized Trial Evaluating Ranibizumab Plus Prompt or Deferred Laser or Triamcinolone Plus Prompt Laser for Diabetic Macular Edema", Ophthalmology, Jun. 2010, 117(6), e35, 1064-1077.

Evans et al., "Selective Inhibitors of Plasma Kallikrein", Immunopharmacology, May 1996, 32(1-3), 115-116.

Garrett et al. "Peptide Aldehyde Inhibitors of the Kallikreins: an Investigation of Subsite Interactions with Tripeptides Containing Structural Variations at the Amino Terminus", J. Peptide Research, Jul. 1998, 52(1), 60-71.

Griesbacher et al., "Involvement of Tissue Kallikrein But Not Plasma Kallikrein in the Development of Symptoms Mediated by Endogenous Kinins in Acute Pancreatitis in Rats", British Journal of Pharmacology, Nov. 2002, 137, 692-700.

Johansen et al., "Assay of Kallikrein Inhibitors and Levels of Acetone-Activated Kallikrein in Plasma Specimens From Reactors to Dextran or to Contrast Media", Int. J. Tiss. Reac., 1986, 185-192.

Kolte et al., "Biochemical Characterization of a Novel High-Affinity and Specific Kallikrein Inhibitor", British Journal of Pharmacology, Apr. 2011, 162, 1639-1649.

Lehmann, "Ecallantide (DX-88), A Plasma Kallikrein Inhibitor for the Treatment of Hereditary Angioedema and the Prevention of Blood Loss in On-Pump Cardiothoracic Surgery", Expert Opinion on Biological Therapy, Jul. 2008, 8(8), 1187-1199.

Leinweber et al, "Possible Physiological Roles of Carboxylic Ester Hydrolases", Drug Metabolism Reviews, Jan. 1987, 18(4), 379-439.

Liang et al., "Fast Dissolving Intraoral Drug Delivery Systems", Expert Opinion in Therapeutic Patents, Jun. 2001, 11(6), 981-986.

Lieberman et al., "Pharmaceutical Dosage Forms: Tablets", Marcel Dekker, Inc., 1980, 145-157.

Marceau et al., "Bradykinin Receptor Ligands: Therapeutic Perspectives", Nature Reviews Drug Discovery, Oct. 2004, 3, 845-852.

Okada et al.; "Development of Potent and Selective Plasmin and Plasma Kallikrein Inhibitors and Studies on the Structure-Activity Relationship", Chem. Pharm. Bull., Sep. 2000, 48(12), 1964-1972.

Patel, "Combination Therapy for Age-Related Macular Degeneration", Retina, Jun. 2009, 29(6), S45-S48.

Shori et al., "New Specific Assays for Tonin and Tissue Kallikrein Activities in Rat Submandibular Glands", Biochemical Pharmacology, Mar. 1992, 43(6), 1209-1217.

Stahl, "A Handbook of Pharmaceutical Salts: Properties, Selection and Use", Wiley-VCH, Weinheim, Germany, 2002, 24(3), p. 20.

Sturzbecher et al., "Inhibition of Human Mast Cell Tryptase by Benzamidine Derivatives", Biol. Chem. Hoppe-Seyler, Oct. 1992, 373, 1025.

Stürzebecher et al., "Novel Plasma Kallikrein Inhibitors of the Benzamidine Type", Brazilian J Med Biol Res, Aug. 1994, 27(8), 1929-1934.

Teno et al., "Development of Active Center-Directed Plasmin and Plasma Kallikrein Inhibitors and Studies on the Structure-Inhibitory Activity Relationship", Chemical and Pharmaceutical Bulletin, Jun. 1993, 41(6), 1079-1090.

Wermuth, "The Practice of Medicinal Chemistry", 2003, 2nd Ed., pp. 561-585.

Young et al., "Small Molecule Inhibitors of Plasma Kallikrein", Bioorganic & Medicinal Chemistry Letters, Apr. 2006, 16(7), 2034-2036.

Zhang et al., "Discovery of Highly Potent Small Molecule Kallikrein Inhibitors"; Medicinal Chemistry, Nov. 2006, 2(6), 545-553.

Ulven et al.; "6-Acylamino-2-amino-4-methylquinolines as potent melanin-concentrating hormone 1 receptor antagonists: Structure-activity exploration of eastern and western parts"; Bioorganic & Medicinal Chemistry Letters; vol. 16 Issue 4; Feb. 2006; p. 1070-1075.

Lussis et al.; "A single synthetic small molecule that generates force against a load"; Nature Nanotechnology; vol. 6; 2011; p. 553-557.

Lussis et al.; "A single synthetic small molecule that generates force against a load"; Nature Nanotechnology; vol. 6; 2011; p. S1-525 (Supplemental Information).

Bhoola et al.; "Kallikrein-Kinin Cascade"; Encyclopedia of Respiratory Medicine; 2006; p. 483-493.

Collis et al.; "BCX4161, An Oral Kallikrein Inhibitor: Safety and Pharmacokinetic Results of a Phase 1 Study in Healthy Volunteers"; Journal of Allergy and Clinical Immunology; Feb. 2014; vol. 133 Issue 2; p. AB39.

Babu et al.; "A Simple, Sensitive and Selective Fluorogenic Assay to Monitor Plasma Kallikrein Inhibitory Activity of BCX4161 in Activated Plasma"; Journal of Allergy and Clinical Immunology; Feb. 2014; vol. 133 Issue 2; p. AB40.

Remington: Practice of the Science and Pharmacy; 19th Edition; Mack Publishing; 1995; 5 pages.

STN Registry, "5-Pyrimidinecarboxamide, N-[1-(1H-benzimidazol-2-yl)ethyl]-1,6-dihydro-6-oxo-2-(phenoxymethyl)", CAS No. 1434334-41-4, Jun. 5, 2013.

STN Registry, "5-Pyrimidinecarboxamide, 1,6-dihydro-N-[1-(6-methyl-1H-benzimidazol-2-yl)ethyl]-2-oxo-2-(1H-1,2,4-triazol-1-ylmethyl)", CAS No. 1422635-37-7, Mar. 8, 2013.

\* cited by examiner

INHIBITORS OF PLASMA KALLIKREIN

CROSS-REFERENCE TO RELATED APPLICATIONS

This application is the National Stage of International Patent Application No. PCT/GB2014/052510 filed Aug. 14, 2014, which claims the benefit of U.S. Provisional Patent Application No. 61/865,732, filed Aug. 14, 2013 and U.S. Provisional Patent Application No. 61/865,756, filed Aug. 14, 2013, the disclosures of which are incorporated herein by reference in their entireties.

This invention relates to inhibitors of plasma kallikrein and to pharmaceutical compositions containing and the uses of, such derivatives.

BACKGROUND TO THE INVENTION

The inhibitors of the present invention are inhibitors of plasma kallikrein and have a number of therapeutic applications, particularly in the treatment of retinal vascular permeability associated with diabetic retinopathy and diabetic macular edema.

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" *Cardiovascular and haematological agents in medicinal chemistry*, 7, p 234-250, 2009; K. D. Bhoola et al., Pharmacological Rev., 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein. Kinins are potent mediators of inflammation that act through G protein-coupled receptors and antagonists of kinins (such as bradykinin antagonists) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" *Diabetes*, 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular edema.

Other complications of diabetes such as cerebral haemorrhage, nephropathy, cardiomyopathy and neuropathy, all of which have associations with plasma kallikrein may also be considered as targets for a plasma kallikrein inhibitor.

Synthetic and small molecule plasma kallikrein inhibitors have been described previously, for example by Garrett et al. ("Peptide aldehyde . . . ." *J. Peptide Res.* 52, p 62-71 (1998)), T. Griesbacher et al. ("Involvement of tissue kallikrein but not plasma kallikrein in the development of symptoms mediated by endogenous kinins in acute pancreatitis in rats" *British Journal of Pharmacology* 137, p 692-700 (2002)), Evans ("Selective dipeptide inhibitors of kallikrein" WO03/076458), Szelke et al. ("Kininogenase inhibitors" WO92/04371), D. M. Evans et al. (*Immunolpharmacology*, 32, p 115-116 (1996)), Szelke et al. ("Kininogen inhibitors" WO95/07921), Antonsson et al. ("New peptides derivatives" WO94/29335), J. Corte et al. ("Six membered heterocycles useful as serine protease inhibitors" WO2005/123680), J. Stürzbecher et al. (*Brazilian J. Med. Biol. Res* 27, p 1929-34 (1994)), Kettner et al. (U.S. Pat. No. 5,187,157), N. Teno et al. (*Chem. Pharm. Bull.* 41, p 1079-1090 (1993)), W. B. Young et al. ("Small molecule inhibitors of plasma kallikrein" *Bioorg. Med. Chem. Letts.* 16, p 2034-2036 (2006)), Okada et al. ("Development of potent and selective plasmin and plasma kallikrein inhibitors and studies on the structure-activity relationship" *Chem. Pharm. Bull.* 48, p 1964-72 (2000)), Steinmetzer et al. ("Trypsin-like serine protease inhibitors and their preparation and use" WO08/049595), Zhang et al. ("Discovery of highly potent small molecule kallikrein inhibitors" *Medicinal Chemistry* 2, p 545-553 (2006)), Sinha et al. ("Inhibitors of plasma kallikrein" WO08/016883), Shigenaga et al. ("Plasma Kallikrein Inhibitors" WO2011/118672), and Kolte et al. ("Biochemical characterization of a novel high-affinity and specific kallikrein inhibitor", British Journal of Pharmacology (2011), 162(7), 1639-1649). Also, Steinmetzer et al. ("Serine protease inhibitors" WO2012/004678) describes cyclized peptide analogs which are inhibitors of human plasmin and plasma kallikrein.

To date, no small molecule synthetic plasma kallikrein inhibitor has been approved for medical use. The molecules described in the known art suffer from limitations such as poor selectivity over related enzymes such as KLK1, thrombin and other serine proteases, and poor oral availability. The large protein plasma kallikrein inhibitors present risks of anaphylactic reactions, as has been reported for Ecallantide. Thus there remains a need for compounds that selectively inhibit plasma kallikrein, that do not induce anaphylaxis and that are orally available. Furthermore, the vast majority of molecules in the known art feature a highly polar and ionisable guanidine or amidine functionality. It is well known that such functionalities may be limiting to gut permeability and therefore to oral availability. For example, it has been reported by Tamie J. Chilcote and Sukanto Sinha ("ASP-634: An Oral Drug Candidate for Diabetic MacularEdema", ARVO 2012 May 6-May 9, 2012, Fort Lauderdale, Fla., Presentation 2240) that ASP-440, a benzamidine, suffers from poor oral availability. It is further reported that absorption may be improved by creating a prodrug such as ASP-634. However, it is well known that prodrugs can suffer from several drawbacks, for example, poor chemical stability and potential toxicity from the inert carrier or from unexpected metabolites. In another report, indole amides are claimed as compounds that might overcome problems associated with drugs possessing poor or inadequate ADME-tox and physicochemical properties although no inhibition against plasma kallikrein is presented or claimed (Griffioen et al, "Indole amide derivatives and related compounds for use in the treatment of neurodegenerative diseases", WO2010, 142801).

BioCryst Pharmaceuticals Inc. have reported the discovery of the orally available plasma kallikrein inhibitor BCX4161 ("BCX4161, An Oral Kallikrein Inhibitor: Safety and Pharmacokinetic Results Of a Phase 1 Study In Healthy Volunteers", Journal of Allergy and Clinical Immunology, Volume 133, Issue 2, Supplement, February 2014, page AB39 and "A Simple, Sensitive and Selective Fluorogenic Assay to Monitor Plasma Kallikrein Inhibitory Activity of BCX4161 in Activated Plasma", Journal of Allergy and Clinical Immunology, Volume 133, Issue 2, Supplement February 2014, page AB40). However, human doses are relatively large, currently being tested in proof of concept studies at doses of 400 mg three times daily.

There are only few reports of plasma kallikrein inhibitors that do not feature guanidine or amidine functionalities. One example is Brandl et al. ("N-((6-amino-pyridin-3-yl) methyl)-heteroaryl-carboxamides as inhibitors of plasma kallikrein" WO2012/017020), which describes compounds that feature an aminopyridine functionality. Oral efficacy in a rat model is demonstrated at relatively high doses of 30 mg/kg and 100 mg/kg but the pharmacokinetic profile is not reported. Thus it is not yet known whether such compounds will provide sufficient oral availability or efficacy for progression to the clinic. Other examples are Brandl et al. ("Aminopyridine derivatives as plasma kallikrein inhibitors" WO2013/111107) and Flohr et al. ("5-membered heteroarylcarboxamide derivatives as plasma kallikrein inhibitors" WO2013/111108). However, neither of these documents report any in vivo data and therefore it is not yet known whether such compounds will provide sufficient oral availability or efficacy for progression to the clinic.

Therefore there remains a need to develop new plasma kallikrein inhibitors that will have utility to treat a wide range of disorders, in particular to reduce retinal vascular permeability associated with diabetic retinopathy and diabetic macular edema. Preferred compounds will possess a good pharmacokinetic profile and in particular will be suitable as drugs for oral delivery.

SUMMARY OF THE INVENTION

The present invention relates to a series of amides that are inhibitors of plasma kallikrein. These compounds demonstrate good selectivity for plasma kallikrein and are potentially useful in the treatment of impaired visual acuity, diabetic retinopathy, macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery. The invention further relates to pharmaceutical compositions of the inhibitors, to the use of the compositions as therapeutic agents, and to methods of treatment using these compositions.

In an aspect, the present invention provides compounds of formula I

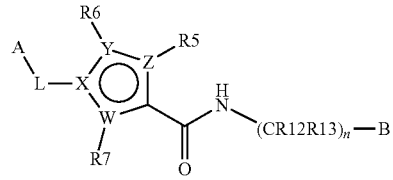

Formula (I)

wherein

B is

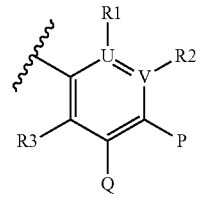

or B is a fused 6,5- or 6,6-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, $CF_3$ and NR8R9;

n is 0, 1 or 2;

W, X, Y and Z are independently selected from C, C(R16)-C, C(R16)=C, C=N, N, O and S, such that the ring containing W, X, Y and Z is a six-membered aromatic heterocycle;

wherein,

R5, R6 and R7 are independently absent or independently selected from H, alkyl, alkoxy, halo, OH, aryl, heteroaryl, —NR8R9, CN, COOR8, CONR8R9, —NR8COR9 and $CF_3$; and R16 is independently selected from H, alkyl, alkoxy, halo, OH, NR8R9, aryl, heteroaryl and $CF_3$;

A is selected from aryl, heteroaryl, and a substituent group selected from formula (A), (B), (C), and (D):

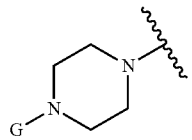

Formula (A)

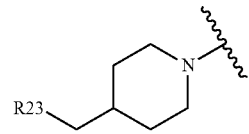

Formula (B)

Formula (C)

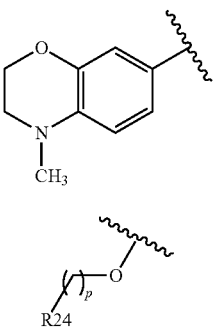

Formula (D)

![Formula D structure]

wherein:
G is selected from H, alkyl, cycloalkyl, CO-aryl, SO$_2$-aryl, (CH$_2$)$_m$-aryl, and (CH$_2$)$_m$-heteroaryl;
m is selected from 0 and 1;
p is selected from 0, 1, 2 and 3;
R23 is selected from aryl and heteroaryl;
R24 is selected from aryl and heteroaryl;
L is a linker selected from a covalent bond, —(CHR17)-, —(CH$_2$)$_{1-10}$—, —O—(CH$_2$)$_{2-10}$—, —(CH$_2$)$_{1-10}$—O—(CH$_2$)$_{1-10}$—, —(CH$_2$)$_{1-10}$—NH—(CH$_2$)$_{1-10}$—, —CONH—(CH$_2$)$_{1-10}$—, —CO—, and —SO$_2$—;
U and V are independently selected from C and N such that the aromatic ring containing U and V is phenyl, pyridine or pyrazine;
R1 is absent when U is N;
R2 is absent when V is N;
or, when present, R1 and R2 are independently selected from H, alkyl, alkoxy, CN, halo and CF$_3$;
R3 is selected from H, alkyl, alkoxy, CN, halo and CF$_3$;
P is H and Q is —C(R18)(R19)NH$_2$, or P is —C(R18)(R19)NH$_2$ and Q is H;
R8 and R9 are independently selected from H and alkyl;
R12 and R13 are independently selected from H and alkyl, or may together form a cycloalkyl ring;
R17 is selected from alkyl and OH;
R18 and R19 are independently selected from H and alkyl, or may together form a cycloalkyl ring or a cyclic ether;
alkyl is a linear saturated hydrocarbon having up to 10 carbon atoms (C$_1$-C$_{10}$) or a branched saturated hydrocarbon of between 3 and 10 carbon atoms (C$_3$-C$_{10}$); alkyl may optionally be substituted with 1 or 2 substituents independently selected from (C$_1$-C$_6$)alkoxy, OH, CN, CF$_3$, COOR10, CONR10R11, fluoro, phenyl and NR10R11;
cycloalkyl is a monocyclic saturated hydrocarbon of between 3 and 7 carbon atoms;
a cyclic ether is a monocyclic saturated hydrocarbon of between 4 and 7 carbon atoms, wherein one of the ring carbons is replaced by an oxygen atom;
alkoxy is a linear O-linked hydrocarbon of between 1 and 6 carbon atoms (C$_1$-C$_6$) or a branched O-linked hydrocarbon of between 3 and 6 carbon atoms (C$_3$-C$_6$); alkoxy may optionally be substituted with 1 or 2 substituents independently selected from OH, OCH$_3$, CN, CF$_3$, COOR10, CONR10R11, fluoro and NR10R11;
aryl is phenyl, biphenyl or naphthyl; aryl may be optionally substituted with 1, 2 or 3 substituents independently selected from alkyl, alkoxy, methylenedioxy, ethylenedioxy, OH, halo, CN, morpholinyl, piperidinyl, heteroaryl, —(CH$_2$)$_{0-3}$—O-heteroaryl, aryl$^b$, —O-aryl$^b$, —(CH$_2$)$_{1-3}$-aryl$^b$, —(CH$_2$)$_{1-3}$-heteroaryl, —COOR10, —CONR10R11, —(CH$_2$)$_{1-3}$—NR14R15, CF$_3$ and —NR10R11;

aryl$^b$ is phenyl, biphenyl or naphthyl, which may be optionally substituted with 1, 2 or 3 substituents independently selected from alkyl, alkoxy, OH, halo, CN, morpholinyl, piperidinyl, —COOR10, —CONR10R11, CF$_3$ and NR10R11;

heteroaryl is a 5, 6, 9 or 10 membered mono- or bi-cyclic aromatic ring, containing, where possible, 1, 2 or 3 ring members independently selected from N, NR8, S and O; heteroaryl may be optionally substituted with 1, 2 or 3 substituents independently selected from alkyl, alkoxy, OH, halo, CN, aryl, morpholinyl, piperidinyl, —(CH$_2$)$_{1-3}$-aryl, heteroaryl$^b$, —COOR10, —CONR10R11, CF$_3$ and —NR10R11;

heteroaryl$^b$ is a 5, 6, 9 or 10 membered mono- or bi-cyclic aromatic ring, containing, where possible, 1, 2 or 3 ring members independently selected from N, NR8, S and O; wherein heteroaryl$^b$ may be optionally substituted with 1, 2 or 3 substituents independently selected from alkyl, alkoxy, OH, halo, CN, morpholinyl, piperidinyl, aryl, —(CH$_2$)$_{1-3}$-aryl, —COOR10, —CONR10R11, CF$_3$ and NR10R11;

R10 and R11 are independently selected from H and alkyl; or R10 and R11 together with the nitrogen to which they are attached form a 4-, 5-, 6- or 7-membered heterocyclic ring which may be saturated or unsaturated with 1 or 2 double bonds and which may be optionally mono- or di-substituted with substituents selected from oxo, alkyl, alkoxy, COOR8, OH, F and CF$_3$;

R14 and R15 are independently selected from alkyl, aryl$^b$ and heteroaryl$^b$; or R14 and R15 together with the nitrogen to which they are attached form a 4-, 5-, 6- or 7-membered heterocylic ring which may be saturated or unsaturated with 1 or 2 double bonds, and optionally may be oxo substituted;

and tautomers, isomers, stereoisomers (including enantiomers, diastereoisomers and racemic and scalemic mixtures thereof), pharmaceutically acceptable salts and solvates thereof.

In another aspect the present invention provides a prodrug of a compound of formula (I) as herein defined, or a pharmaceutically acceptable salt thereof.

In yet another aspect the present invention provides an N-oxide of a compound of formula (I) as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms.

In an aspect, the present invention provides compounds of formula Ia

Formula (Ia)

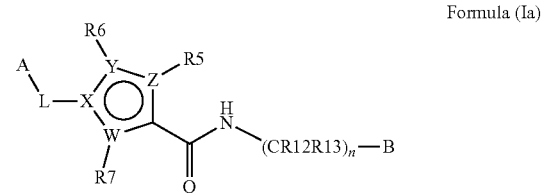

wherein
B is

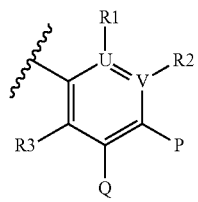

or B is a fused 6,5- or 6,6-heteroaromatic bicyclic ring, containing N and, optionally, one or two additional heteroatoms independently selected from N, O and S which is optionally mono-, di or tri-substituted with a substituent selected from alkyl, alkoxy, OH, halo, CN, COOR8, CONR8R9, CF$_3$ and NR8R9;

n is 0, 1 or 2;

W, X, Y and Z are independently selected from C(R16)-C, C(R16)=C, C, N, O and S, such that the ring containing W, X, Y and Z is a six-membered aromatic heterocycle;

wherein,

R5, R6 and R7 are independently absent or independently selected from H, alkyl, halo, OH, aryl, heteroaryl and CF$_3$; and R16 is independently selected from H, alkyl, alkoxy, halo, OH, aryl, heteroaryl and CF$_3$;

A is selected from aryl, heteroaryl, and a non-aromatic five or six-membered ring containing N or NR10 and optionally containing one or two additional heteroatoms selected from N, O and S, wherein said ring is optionally fused to phenyl;

L is a linker selected from a covalent bond, —(CH$_2$)$_{1-10}$—, —O—(CH$_2$)$_{2-10}$—, —(CH$_2$)$_{1-10}$—O—(CH$_2$)$_{1-10}$—, —(CH$_2$)$_{1-10}$—NH—(CH$_2$)$_{1-10}$—, —CONH—(CH$_2$)$_{1-10}$, —CO—, and —SO$_2$—;

U and V are independently selected from C and N such that the aromatic ring containing U and V is phenyl, pyridine or pyrazine;

R1 is absent when U is N;

R2 is absent when V is N;

or, when present, R1 and R2 are independently selected from H, alkyl, alkoxy, CN, halo and CF$_3$;

R3 is selected from H, alkyl, alkoxy, CN, halo and CF$_3$;

P is H and Q is —C(R18)(R19)NH$_2$, or P is —C(R18)(R19)NH$_2$ and Q is H;

R8 and R9 are independently selected from H and alkyl;

R12 and R13 are independently selected from H and alkyl, or may together form a cycloalkyl ring;

R18 and R19 are independently selected from H and alkyl, or may together form a cycloalkyl ring or a cyclic ether;

alkyl is a linear saturated hydrocarbon having up to 10 carbon atoms (C$_1$-C$_{10}$) or a branched saturated hydrocarbon of between 3 and 10 carbon atoms (C$_3$-C$_{10}$); alkyl may optionally be substituted with 1 or 2 substituents independently selected from (C$_1$-C$_6$)alkoxy, OH, CN, CF$_3$, COOR10, CONR10R11, fluoro and NR10R11;

cycloalkyl is a monocyclic saturated hydrocarbon of between 3 and 7 carbon atoms;

a cyclic ether is a monocyclic saturated hydrocarbon of between 4 and 7 carbon atoms, wherein one of the ring carbons is replaced by an oxygen atom;

alkoxy is a linear O-linked hydrocarbon of between 1 and 6 carbon atoms (C$_1$-C$_6$) or a branched O-linked hydrocarbon of between 3 and 6 carbon atoms (C$_3$-C$_6$); alkoxy may optionally be substituted with 1 or 2 substituents independently selected from OH, CN, CF$_3$, COOR10, CONR10R11, fluoro and NR10R11;

aryl is phenyl, biphenyl or naphthyl; aryl may be optionally substituted with 1, 2 or 3 substituents independently selected from alkyl, alkoxy, methylenedioxy, ethylenedioxy, OH, halo, CN, morpholinyl, piperidinyl, heteroaryl, —(CH$_2$)$_{0-3}$—O-heteroaryl, aryl$^b$, —O-aryl$^b$, —(CH$_2$)$_{1-3}$-aryl$^b$, —(CH$_2$)$_{1-3}$-heteroaryl, —COOR10, —CONR10R11, —(CH$_2$)$_{1-3}$—NR14R15, CF$_3$ and —NR10R11;

aryl$^b$ is phenyl, biphenyl or naphthyl, which may be optionally substituted with 1, 2 or 3 substituents independently selected from alkyl, alkoxy, OH, halo, CN, morpholinyl, piperidinyl, —COOR10, —CONR10R11, CF$_3$ and NR10R11;

heteroaryl is a 5, 6, 9 or 10 membered mono- or bi-cyclic aromatic ring, containing, where possible, 1, 2 or 3 ring members independently selected from N, NR8, S and O; heteroaryl may be optionally substituted with 1, 2 or 3 substituents independently selected from alkyl, alkoxy, OH, halo, CN, aryl, morpholinyl, piperidinyl, —(CH$_2$)$_{1-3}$-aryl, heteroaryl$^b$, —COOR10, —CONR10R11, CF$_3$ and —NR10R11;

heteroaryl$^b$ is a 5, 6, 9 or 10 membered mono- or bi-cyclic aromatic ring, containing, where possible, 1, 2 or 3 ring members independently selected from N, NR8, S and O; wherein heteroaryl$^b$ may be optionally substituted with 1, 2 or 3 substituents independently selected from alkyl, alkoxy, OH, halo, CN, morpholinyl, piperidinyl, aryl, —(CH$_2$)$_{1-3}$-aryl, —COOR10, —CONR10R11, CF$_3$ and NR10R11;

R10 and R11 are independently selected from H and alkyl; or R10 and R11 together with the nitrogen to which they are attached form a 4-, 5-, 6- or 7-membered heterocylic ring which may be saturated or unsaturated with 1 or 2 double bonds;

R14 and R15 are independently selected from alkyl, aryl$^b$ and heteroaryl$^b$; or R14 and R15 together with the nitrogen to which they are attached form a 4-, 5-, 6- or 7-membered heterocylic ring which may be saturated or unsaturated with 1 or 2 double bonds, and optionally may be oxo substituted;

and tautomers, isomers, stereoisomers (including enantiomers, diastereoisomers and racemic and scalemic mixtures thereof), pharmaceutically acceptable salts and solvates thereof.

In an aspect, the invention comprises a subset of the compounds of formula I

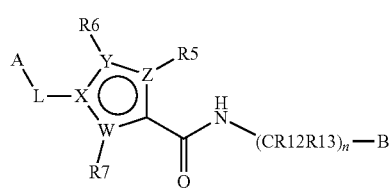

Formula (I)

wherein

L is a linker selected from a covalent bond, —(CHOH)—, and —(CH$_2$)$_{1-6}$—;

B is

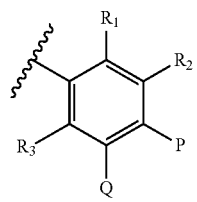

or B is a fused 6,5- or 6,6-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, $CF_3$ and NR8R9;

and wherein A, W, X, Y, Z, R1, R2, R3, R5, R6, R7, R8, R9, R12, R13, R17, alkyl, alkoxy and n are as defined according to formula (I) or formula (Ia) above, and tautomers, isomers, stereoisomers (including enantiomers, diastereoisomers and racemic and scalemic mixtures thereof), pharmaceutically acceptable salts and solvates thereof.

In an aspect, the invention comprises a subset of the compounds of formula (I), as defined by formula (II), Formula (II)

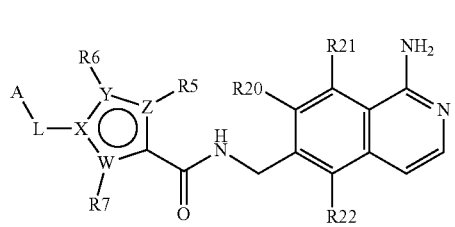

wherein R20, R21 and R22 are independently selected from H, alkyl, COOR8, CONR8R9, OH, alkoxy, NR8R9, F and Cl; and wherein A, L, W, X, Y, Z, R5, R6, R7, alkyl, alkoxy, R8 and R9 are as defined according to formula (I) or formula (Ia) above;

and tautomers, isomers, stereoisomers (including enantiomers, diastereoisomers and racemic and scalemic mixtures thereof), pharmaceutically acceptable salts and solvates thereof.

In an aspect, the invention comprises a subset of the compounds of formula (I), as defined by formula (II), Formula (II)

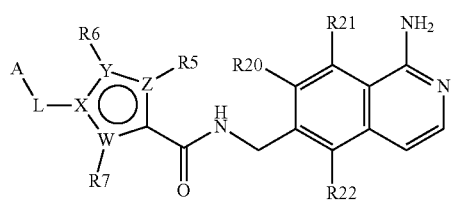

wherein R20, R21 and R22 are independently selected from H, alkyl, COOR8, CONR8R9, OH, alkoxy, NR8R9, F and Cl;

L is a linker selected from —(CHOH)—, and —$(CH_2)_{1-6}$—;

and wherein A, W, X, Y, Z, R5, R6, R7, alkyl, alkoxy, R8 and R9 are as defined according to formula (I) or formula (Ia) above;

and tautomers, isomers, stereoisomers (including enantiomers, diastereoisomers and racemic and scalemic mixtures thereof), pharmaceutically acceptable salts and solvates thereof.

In an aspect, the invention comprises a subset of the compounds of formula (I), as defined by formula (III), Formula (III)

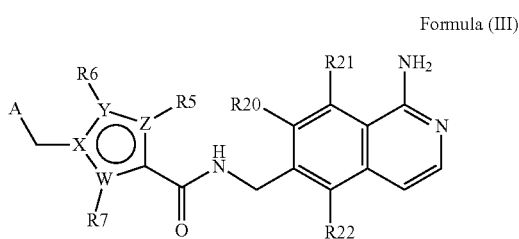

wherein R20, R21 and R22 are independently selected from H, alkyl, COOR8, CONR8R9, OH, alkoxy, NR8R9, F and Cl; and wherein A, W, X, Y, Z, R5, R6, R7, alkyl, alkoxy, R8 and R9 are as defined according to formula (I) or formula (Ia) above;

and tautomers, isomers, stereoisomers (including enantiomers, diastereoisomers and racemic and scalemic mixtures thereof), pharmaceutically acceptable salts and solvates thereof.

In an aspect, the invention comprises a subset of the compounds of formula (I), as defined by formula (IV), Formula (IV)

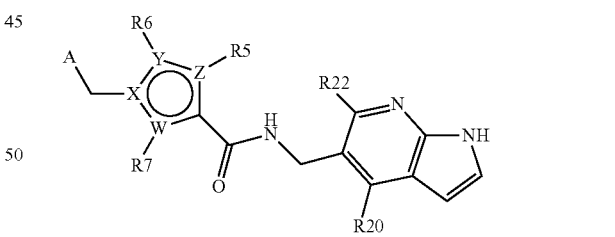

wherein R20 and R22 are independently selected from H, alkyl, COOR8, CONR8R9, OH, alkoxy, NR8R9, F and Cl; and wherein A, W, X, Y, Z, R5, R6, R7, alkyl, alkoxy, R8 and R9 are as defined according to formula (I) or formula (Ia) above;

and tautomers, isomers, stereoisomers (including enantiomers, diastereoisomers and racemic and scalemic mixtures thereof), pharmaceutically acceptable salts and solvates thereof.

In an aspect, the invention comprises a subset of the compounds of formula (I), as defined by formula (V),

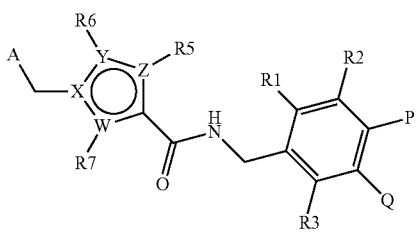

Formula (V)

wherein A, W, X, Y, Z, R1, R2, R3, R5, R6, R7, P and Q are as defined according to formula (I) or formula (Ia) above;

and tautomers, isomers, stereoisomers (including enantiomers, diastereoisomers and racemic and scalemic mixtures thereof), pharmaceutically acceptable salts and solvates thereof.

The present invention also comprises the following aspects and combinations thereof:

Compounds of formula (I) wherein B is a fused 6,5- or 6,6-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, $CF_3$ and NR8R9; wherein R8 and R9 are independently selected from H and alkyl; wherein when B is a fused 6,5-heteroaromatic aza-bicycle, it is linked to —$(CR12R13)_n$- via its 6-membered ring component.

Compounds of formula (I) wherein, B is a fused 6,5 or 6,6-heteroaromatic bicyclic ring, containing one, two or three N atoms, which is optionally mono-substituted with a substituent selected from alkyl, alkoxy, OH, halo, CN, COOR8, CONR8R9, $CF_3$ and NR8R9; wherein R8 and R9 are independently selected from H and alkyl.

Compounds of formula (I) wherein, B is a fused 6,6-heteroaromatic aza-bicycle, which is optionally mono-substituted with a substituent selected from alkyl, alkoxy, OH, halo, CN, COOR8, CONR8R9, $CF_3$ and NR8R9; wherein R8 and R9 are independently selected from H and alkyl.

Compounds of formula (I) wherein, B is a fused 6,5- or 6,6-heteroaromatic bicyclic ring, containing N and, optionally, one or two additional heteroatoms independently selected from N and O, which is optionally mono-substituted with a substituent selected from alkyl, alkoxy, OH, halo, CN, COOR8, CONR8R9, $CF_3$ and NR8R9; wherein R8 and R9 are independently selected from H and alkyl.

Compounds of formula (I) wherein, B is a fused 6,6-heteroaromatic aza-bicycle, which is optionally mono-substituted with a substituent selected from alkyl, alkoxy, OH, and NR8R9; wherein R8 and R9 are independently selected from H and alkyl.

Compounds of formula (I) wherein, B is a fused 6,6-heteroaromatic aza-bicycle, which is optionally mono-substituted with NR8R9; wherein R8 and R9 are independently selected from H and alkyl.

Compounds of formula (I) wherein, B is optionally mono-, di or tri-substituted isoquinolinyl, wherein said optional substituent(s) are selected from alkyl, alkoxy, OH, F, Cl, CN, COOR8, CONR8R9, $CF_3$ and NR8R9; wherein R8 and R9 are independently selected from H and alkyl.

Compounds of formula (I) wherein, B is optionally mono-substituted isoquinolinyl; wherein said optional substituent is selected from alkyl, alkoxy, OH, and NR8R9; wherein R8 and R9 are independently selected from H and alkyl.

Compounds of formula (I) wherein, B is optionally substituted 1H-pyrrolo[2,3-b]pyridine wherein said optional substituent(s) are selected from alkyl, alkoxy, OH, F, Cl, CN, COOR8, CONR8R9, $CF_3$ and NR8R9 and wherein R8 and R9 are independently selected from H and alkyl.

Compounds of formula (I) wherein, B is:

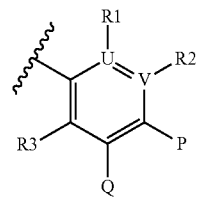

and wherein R1, R2, R3, P, Q, U and V are as defined according to formula (I) or formula (Ia) above.

Compounds of formula (I) wherein, B is:

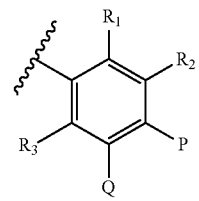

and wherein R1, R2, R3, P and Q are as defined according to formula (I) or formula (Ia) above.

Compounds of formula (I) wherein, B is:

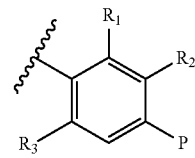

and wherein R1, R2, R3 and P are as defined according to formula (I) or formula (Ia) above.

Preferred are compounds of formula (I) wherein, B is optionally mono-substituted isoquinolinyl, wherein said optional substituent is NR8R9; wherein R8 and R9 are independently selected from H and alkyl.

More preferred are compounds of formula (I) wherein, B is optionally mono-substituted isoquinolinyl, wherein said optional substituent is NR8R9; and wherein R8 and R9 are H.

Compounds of formula (I) wherein, U and V are independently selected from C and N such that the aromatic ring containing U and V is phenyl, pyridine or pyrazine.

Compounds of formula (I) wherein, U and V are independently selected from C and N such that the aromatic ring containing U and V is phenyl or pyridine.

Preferred are compounds of formula (I) wherein, U and V are C such that the aromatic ring containing U and V is phenyl.

Compounds of formula (I), wherein R1 is absent when U is N, R2 is absent when V is N; and wherein, when present, R1 and R2 are independently selected from H, alkyl, alkoxy, CN, halo and $CF_3$.

Compounds of formula (I) or formula (V) wherein, when present, R1 and R2 are independently selected from H, methyl, methoxy, Cl, F and CF$_3$.

Compounds of formula (I) or formula (V) wherein, when present, R1 and R2 are independently selected from H, methyl and F.

Compounds of formula (I) or formula (V) wherein, when present, R1 is selected from H and methyl.

Compounds of formula (I) or formula (V) wherein, when present, R2 is selected from H and F.

Compounds of formula (I) or formula (V) wherein, R3 is selected from H, alkyl, alkoxy, CN, halo and CF$_3$;

Compounds of formula (I) or formula (V) wherein, R3 is selected from H and alkyl.

Preferred are compounds of formula (I) or formula (V) wherein, R3 is selected from H and methyl.

Preferred are compounds of formula (I) or formula (V) wherein, P is —C(R18)(R19)NH$_2$ and Q is H.

Preferred are compounds of formula (I), formula (II), formula (III) or formula (IV) wherein, R20, R21 and R22 are independently selected from H and alkyl.

Preferred are compounds of formula (II) or formula (III) wherein, R20, R21 and R22 are H.

Preferred are compounds of formula (IV) wherein, R20 and R22 are H.

Compounds of formula (I) wherein, R12 and R13 are independently selected from H and alkyl, or may together form a cycloalkyl ring.

Preferred are compounds of formula (I) wherein, R12 and R13 are independently selected from H and methyl.

Most preferred are compounds of formula (I) wherein R12 and R13 are H.

Compounds of formula (I) wherein, n is 0, 1 or 2.

Compounds of formula (I) wherein, n is 1 or 2.

Preferred are compounds of formula (I) wherein, n is 1.

Compounds of formula (I), formula (II), formula (III), formula (IV) or formula (V) wherein, W, X, Y and Z are independently selected from C=N, C(R16)-C, C(R16)=C, C, N, O and S, such that the ring containing W, X, Y and Z is a six-membered aromatic heterocycle.

Compounds of formula (I), formula (II), formula (III), formula (IV) or formula (V) wherein, W, X, Y and Z are independently selected from C=N, C, C(R16)-C, C(R16)=C and N, such that the ring containing W, X, Y and Z is a six-membered aromatic heterocycle; wherein R16 is selected from H, alkyl and OH.

Compounds of formula (I), formula (II), formula (III), formula (IV) or formula (V) wherein, W, X, Y and Z are independently selected from C, C(R16)-C, C(R16)=C and N, such that the ring containing W, X, Y and Z is a six-membered aromatic heterocycle; wherein R16 is selected from H, alkyl and OH.

Preferred are compounds of formula (I), formula (II), formula (III), formula (IV) or formula (V) wherein, W is C or N.

Preferred are compounds of formula (I), formula (II), formula (III), formula (IV) or formula (V) wherein, X is selected from C, C(R16)-C, C(R16)=C or N.

Preferred are compounds of formula (I), formula (II), formula (III), formula (IV) or formula (V) wherein, X is selected from C(R16)-C or C(R16)=C and R16 is H; Y is N; and W and Z are C.

Most preferred are compounds of formula (I), formula (II), formula (III), formula (IV) or formula (V) wherein, W, X, Y and Z form a six-membered aromatic heterocycle selected from:

Compounds of formula (I), formula (II), formula (III), formula (IV) or formula (V) wherein, R5, R6 and R7 are independently absent, or are independently selected from H, alkyl, alkoxy, halo, OH, aryl, heteroaryl, —NR8R9, CN, COOR8, CONR8R9, —NR8COR9 and CF$_3$.

Compounds of formula (I), formula (II), formula (III), formula (IV) or formula (V) wherein, R5, R6 and R7 are independently absent, or are independently selected from H, alkyl, alkoxy, halo, OH, aryl, heteroaryl and CF$_3$.

Compounds of formula (I), formula (II), formula (III), formula (IV) or formula (V) wherein, R5 is selected from H, alkyl and OH; and wherein R6 and R7 are independently absent or H.

Preferred are compounds of formula (I), formula (II), formula (III) or formula (IV) wherein, R5 is selected from H, methyl and OH; R6 is absent; and R7 is H.

Compounds of formula (I), formula (II), formula (III), formula (IV) or formula (V) wherein, R14 and R15 are independently selected from alkyl, aryl$^b$ and heteroaryl$^b$; or R14 and R15 together with the nitrogen to which they are attached form a 4-, 5-, 6- or 7-membered heterocylic ring which may be saturated or unsaturated with 1 or 2 double bonds, and optionally may be oxo substituted.

Compounds of formula (I), formula (II), formula (III), formula (IV) or formula (V) wherein, R14 and R15 are independently selected from alkyl and heteroaryl$^b$; or R14 and R15 together with the nitrogen to which they are attached form a 4-, 5-, 6- or 7-membered heterocylic ring which may be saturated or unsaturated with 1 or 2 double bonds, and optionally may be oxo substituted.

Compounds of formula (I), formula (II), formula (III), formula (IV) or formula (V) wherein, R14 and R15 together with the nitrogen to which they are attached form a 4-, 5-, 6- or 7-membered heterocylic ring which may be saturated or unsaturated with 1 or 2 double bonds, and optionally may be oxo substituted.

Compounds of formula (I), formula (II), formula (III), formula (IV) or formula (V) wherein, R16 is independently selected from H, alkyl, alkoxy, halo, OH, NR8R9, aryl, heteroaryl and CF$_3$.

Compounds of formula (I), formula (II), formula (III), formula (IV) or formula (V) wherein, R16 is independently selected from H and alkoxy and OH.

Preferred are compounds of formula (I), formula (II), formula (III), formula (IV) or formula (V) wherein, R16 is H.

Compounds of formula (I) or formula (II) wherein, L is a linker selected from a covalent bond, —(CHR17)-, —(CH$_2$)$_{1-10}$—, —O—(CH$_2$)$_{2-10}$—, —(CH$_2$)$_{1-10}$—O—(CH$_2$)$_{1-10}$—, —(CH$_2$)$_{1-10}$—NH—(CH$_2$)$_{1-10}$—, —CONH—(CH$_2$)$_{1-10}$—, —CO—, and —SO$_2$—.

Compounds of formula (I) or formula (II) wherein, L is a linker selected from a covalent bond, —(CH$_2$)$_{1-10}$—, —O—(CH$_2$)$_{2-10}$—, —(CH$_2$)$_{1-10}$—O—(CH$_2$)$_{1-10}$—, —(CH$_2$)$_{1-10}$—NH—(CH$_2$)$_{1-10}$—, —CONH—(CH$_2$)$_{1-10}$—, —CO—, and —SO$_2$—.

Compounds of formula (I) or formula (II) wherein, L is —(CH$_2$)$_{1-6}$— or —(CHR17)-.

Preferred are compounds of formula (I) or formula (II) wherein, L is —(CH$_2$)$_{1-6}$— or —(CHOH)—.

Most preferred are compounds of formula (I) or formula (II) wherein L is —CH$_2$—.

Compounds of formula (I), formula (II), formula (III), formula (IV) or formula (V) wherein, A is selected from aryl, heteroaryl, and a substituent group selected from formula (A), (B), (C), and (D):

Formula (A)

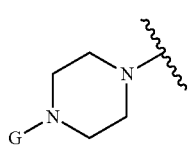

Formula (B)

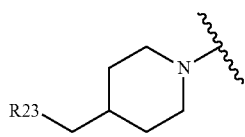

Formula (C)

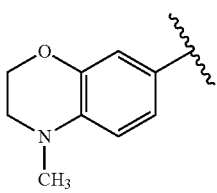

Formula (D)

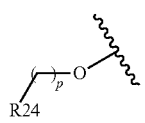

wherein:
G is selected from H, alkyl, cycloalkyl, CO-aryl, SO$_2$-aryl, (CH$_2$)$_m$-aryl, and (CH$_2$)$_m$-heteroaryl;
m is selected from 0 and 1;
p is selected from 0, 1, 2 and 3;
R23 is selected from aryl and heteroaryl;
R24 is selected from aryl and heteroaryl;
wherein alkyl, cycloalkyl, aryl and heteroaryl are as defined according to formula (I) or formula (Ia) above.

Compounds of formula (I), formula (II), formula (III), formula (IV) or formula (V) wherein, A is selected from aryl, heteroaryl, and a substituent selected from formula (C) and (D).

Preferred are compounds of formula (I), formula (II), formula (III), formula (IV) or formula (V) wherein, A is selected from aryl and heteroaryl, each optionally substituted as specified according to formula (I) or formula (Ia) above.

Compounds of formula (I), formula (II), formula (III), formula (IV) or formula (V) wherein, A is heteroaryl optionally substituted with 1, 2 or 3 substituents independently selected from alkyl, alkoxy, OH, halo, CN, aryl, morpholinyl, piperidinyl, —COOR10, —CONR10R11, CF$_3$ and —NR10R11; wherein R10 and R11 are selected from H and alkyl or R10 and R11 together with the nitrogen to which they are attached form a 4-, 5-, 6- or 7-membered heterocylic ring which may be saturated or unsaturated with 1 or 2 double bonds; and wherein alkyl, alkoxy and aryl are as defined according to formula (I) or formula (Ia) above.

Compounds of formula (I), formula (II), formula (III), formula (IV) or formula (V) wherein, A is heteroaryl optionally substituted with a substituent selected from alkyl, alkoxy, OH, halo, CN, aryl, morpholinyl and piperidinyl; and wherein alkyl, alkoxy and aryl are as defined according to formula (I) or formula (Ia) above.

Preferred are compounds of formula (I), formula (II), formula (III), formula (IV) or formula (V) wherein, A is heteroaryl substituted by phenyl.

Preferred are compounds of formula (I), formula (II), formula (III), formula (IV) or formula (V) wherein, A is thiazolyl substituted by phenyl.

Preferred are compounds of formula (I), formula (II), formula (III), formula (IV) or formula (V) wherein, A is phenyl substituted by heteroaryl, —(CH$_2$)$_{1-3}$-heteroaryl and —(CH$_2$)$_{1-3}$—NR14R15; and wherein heteroaryl, R14 and R15 are as defined according to formula (I) or formula (Ia) above.

Preferred are compounds of formula (I), formula (II), formula (III), formula (IV) or formula (V) wherein, A is selected from:

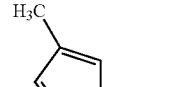

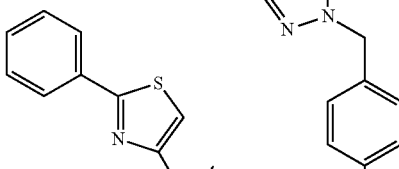

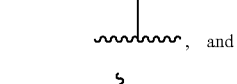
, and

Compounds of formula (I), formula (II), formula (III), formula (IV) or formula (V) wherein, p is selected from 0, 1, 2 and 3.

Preferred are compounds of formula (I), formula (II), formula (III), formula (IV) or formula (V) wherein p is 2.

Compounds of formula (I), formula (II), formula (III), formula (IV) or formula (V) wherein R23 and R24 are independently selected from aryl and heteroaryl; wherein aryl and heteroaryl are as defined according to formula (I) or formula (Ia) above.

Preferred are compounds of formula (I), formula (II), formula (III), formula (IV) or formula (V) wherein R23 and R24 are heteroaryl; wherein heteroaryl is as defined according to formula (I) or formula (Ia) above.

In an aspect, the invention comprises a compound selected from:

N-[(1-Aminoisoquinolin-6-yl)methyl]-5-({4-[(4-methylpyrazol-1-yl)methyl]phenyl}methyl)pyridine-3-carboxamide;
N-[(1-Aminoisoquinolin-6-yl)methyl]-4-({4-[(4-methylpyrazol-1-yl)methyl]phenyl}methyl)pyridine-2-carboxamide;
N-[(1-Aminoisoquinolin-6-yl)methyl]-6-oxo-1-({4-[(2-oxopyridin-1-yl)methyl]phenyl}methyl)pyridine-3-carboxamide;
N-[(1-Aminoisoquinolin-6-yl)methyl]-5-(hydroxy(4-((4-methyl-1H-pyrazol-1-yl)methyl)phenyl)methyl)nicotinamide;
N-[(1-Aminoisoquinolin-6-yl)methyl]-6-({4-[(4-methylpyrazol-1-yl)methyl]phenyl}methyl)pyrimidine-4-carboxamide;
N-[(1-Aminoisoquinolin-6-yl)methyl]-6-({4-[(4-methylpyrazol-1-yl)methyl]phenyl}methyl)pyrazine-2-carboxamide;
N-[(1-Aminoisoquinolin-6-yl)methyl]-6-[(2-methylquinolin-6-yl)methyl]pyrazine-2-carboxamide;
N-[(1-Aminoisoquinolin-6-yl)methyl]-5-({4-[(4-methylpyrazol-1-yl)methyl]phenyl}methyl)pyridazine-3-carboxamide;
N-[(1-Aminoisoquinolin-6-yl)methyl]-1-({4-[(4-methylpyrazol-1-yl)methyl]phenyl}methyl)-6-oxopyridine-3-carboxamide;
N-[(1-Aminoisoquinolin-6-yl)methyl]-1-[(2-methylquinolin-6-yl)methyl]-6-oxopyridine-3-carboxamide;
N-[(1-Aminoisoquinolin-6-yl)methyl]-5-[(2-methylquinolin-6-yl)methyl]pyridine-3-carboxamide;
N-[(1-Aminoisoquinolin-6-yl)methyl]-6-(methylamino)-5-[(2-methylquinolin-6-yl)methyl]pyridine-3-carboxamide;
N-[(1-Aminoisoquinolin-6-yl)methyl]-2-methyl-5-[(2-methylquinolin-6-yl)methyl]pyridine-3-carboxamide;
N-[(1-Aminoisoquinolin-6-yl)methyl]-5-(quinolin-6-ylmethyl)pyridine-3-carboxamide;
N-[(1-Aminoisoquinolin-6-yl)methyl]-5-({3-methoxy-4-[(4-methylpyrazol-1-yl)methyl]phenyl}methyl)pyridine-3-carboxamide;
N-[(1-Aminoisoquinolin-6-yl)methyl]-5-[(4-methyl-2,3-dihydro-1,4-benzoxazin-7-yl)methyl]pyridine-3-carboxamide;
N-[(1-Aminoisoquinolin-6-yl)methyl]-5-{[2-(4-methylpyrazol-1-yl)ethoxy]methyl}pyridine-3-carboxamide;
N-[(1-Aminoisoquinolin-6-yl)methyl]-5-{[6-(2-oxopyrrolidin-1-yl)pyridin-3-yl]methyl}pyridine-3-carboxamide;
N-[(1-Aminoisoquinolin-6-yl)methyl]-5-{[6-(pyrrolidin-1-yl)pyridin-3-yl]methyl}pyridine-3-carboxamide;
N-[(1-Aminoisoquinolin-6-yl)methyl]-5-{[6-(2-methylpyrrolidin-1-yl)pyridin-3-yl]methyl}pyridine-3-carboxamide;
N-[(1-Aminoisoquinolin-6-yl)methyl]-5-{[6-(3-fluoropyrrolidin-1-yl)pyridin-3-yl]methyl}pyridine-3-carboxamide;
N-[(1-Aminoisoquinolin-6-yl)methyl]-5-{[6-(3-methylpyrrolidin-1-yl)pyridin-3-yl]methyl}pyridine-3-carboxamide;
N-[(1-Aminoisoquinolin-6-yl)methyl]-5-{[6-(2,2-dimethylpyrrolidin-1-yl)pyridin-3-yl]methyl}pyridine-3-carboxamide;
N-[(1-Aminoisoquinolin-6-yl)methyl]-5-{[6-(diethylamino)pyridin-3-yl]methyl}pyridine-3-carboxamide;
N-[(1-Aminoisoquinolin-6-yl)methyl]-5-({6-[2-(hydroxymethyl)pyrrolidin-1-yl]pyridin-3-yl}methyl)pyridine-3-carboxamide;
N-[(1-Aminoisoquinolin-6-yl)methyl]-5-({6-[isopropyl(methyl)amino]pyridin-3-yl}methyl)pyridine-3-carboxamide;
N-[(1-Aminoisoquinolin-6-yl)methyl]-5-{[6-(3,3-dimethylpyrrolidin-1-yl)pyridin-3-yl]methyl}pyridine-3-carboxamide;
N-[(1-Aminoisoquinolin-6-yl)methyl]-5-{[2-(pyrrolidin-1-yl)pyridin-4-yl]methyl}pyridine-3-carboxamide;
N-[(1-Aminoisoquinolin-6-yl)methyl]-5-{[2-(piperidin-1-yl)pyridin-4-yl]methyl}pyridine-3-carboxamide;
N-[(1-Aminoisoquinolin-6-yl)methyl]-5-{[2-(2-methylpyrrolidin-1-yl)pyridin-4-yl]methyl}pyridine-3-carboxamide;
N-[(1-Aminoisoquinolin-6-yl)methyl]-5-{[2-(3,3-difluoropyrrolidin-1-yl)pyridin-4-yl]methyl}pyridine-3-carboxamide;
N-[(1-Aminoisoquinolin-6-yl)methyl]-5-{[2-(3-fluoropyrrolidin-1-yl)pyridin-4-yl]methyl}pyridine-3-carboxamide;
N-[(1-Aminoisoquinolin-6-yl)methyl]-5-{[2-(3-methylpyrrolidin-1-yl)pyridin-4-yl]methyl}pyridine-3-carboxamide;
N-[(1-Aminoisoquinolin-6-yl)methyl]-5-({2-[2-(hydroxymethyl)pyrrolidin-1-yl]pyridin-4-yl}methyl)pyridine-3-carboxamide;
N-{[4-(Aminomethyl)-2-methylphenyl]methyl}-5-({4-[(4-methylpyrazol-1-yl)methyl]phenyl}methyl)pyridine-3-carboxamide;
N-{[4-(Aminomethyl)-2,6-dimethylphenyl]methyl}-5-({4-[(4-methylpyrazol-1-yl)methyl]phenyl}methyl)pyridine-3-carboxamide;
N-{[4-(Aminomethyl)-2,6-dimethylphenyl]methyl}-6-({4-[(4-methylpyrazol-1-yl)methyl]phenyl}methyl)pyrazine-2-carboxamide;

and pharmaceutically acceptable salts and solvates thereof.

Therapeutic Applications

As previously mentioned, the compounds of the present invention are potent and selective inhibitors of plasma kallikrein. They are therefore useful in the treatment of disease conditions for which over-activity of plasma kallikrein is a causative factor.

Accordingly, the present invention provides a compound of formula (I) for use in medicine.

The present invention also provides for the use of a compound of formula (I) in the manufacture of a medicament for the treatment or prevention of a disease or condition in which plasma kallikrein activity is implicated.

The present invention also provides a compound of formula (I) for use in the treatment or prevention of a disease or condition in which plasma kallikrein activity is implicated.

The present invention also provides a method of treatment of a disease or condition in which plasma kallikrein activity is implicated comprising administration to a subject in need thereof a therapeutically effective amount of a compound of formula (I).

In one aspect, diseases or conditions in which plasma kallikrein activity is implicated include impaired visual acuity, diabetic retinopathy, diabetic macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery.

In another aspect, the disease or condition in which plasma kallikrein activity is implicated is retinal vascular permeability associated with diabetic retinopathy and diabetic macular edema.

Combination Therapy

The compounds of the present invention may be administered in combination with other therapeutic agents. Suitable combination therapies include a compound of formula (I) combined with one or more agents selected from agents that inhibit platelet-derived growth factor (PDGF), endothelial growth factor (VEGF), integrin alpha5beta1, steroids, other agents that inhibit plasma kallikrein and other inhibitors of inflammation. Specific examples of therapeutic agents that may be combined with the compounds of the present invention include those disclosed in EP2281885A and by S. Patel in *Retina*, 2009 Jun. 29(6 Suppl):S45-8.

When combination therapy is employed, the compounds of the present invention and said combination agents may exist in the same or different pharmaceutical compositions, and may be administered separately, sequentially or simultaneously.

In another aspect, the compounds of the present invention may be administered in combination with laser treatment of the retina. The combination of laser therapy with intravitreal injection of an inhibitor of VEGF for the treatment of diabetic macular edema is known (Elman M, Aiello L, Beck R, et al. "Randomized trial evaluating ranibizumab plus prompt or deferred laser or triamcinolone plus prompt laser for diabetic macular edema". Ophthalmology. 27 Apr. 2010).

Definitions

The term "alkyl" includes saturated hydrocarbon residues including:
linear groups up to 10 carbon atoms ($C_1$-$C_{10}$), or of up to 6 carbon atoms ($C_1$-$C_6$), or of up to 4 carbon atoms ($C_1$-$C_4$). Examples of such alkyl groups include, but are not limited, to $C_1$-methyl, $C_2$-ethyl, $C_3$-propyl and $C_4$-n-butyl.
branched groups of between 3 and 10 carbon atoms ($C_3$-$C_{10}$), or of up to 7 carbon atoms ($C_3$-$C_7$), or of up to 4 carbon atoms ($C_3$-$C_4$). Examples of such alkyl groups include, but are not limited to, $C_3$-isopropyl, $C_4$-sec-butyl, $C_4$-iso-butyl, $C_4$-tert-butyl and $C_5$-neopentyl.
each optionally substituted as stated above.

Cycloalkyl is a monocyclic saturated hydrocarbon of between 3 and 7 carbon atoms; wherein cycloalkyl may be optionally substituted with a substituent selected from alkyl, alkoxy and NR10R11; wherein R10 and R11 are independently selected from H and alkyl or R10 and R11 together with the nitrogen to which they are attached form a 4-, 5-, 6- or 7-membered heterocylic ring which may be saturated or unsaturated with 1 or 2 double bonds. Cycloalkyl groups may contain from 3 to 7 carbon atoms, or from 3 to 6 carbon atoms, or from 3 to 5 carbon atoms, or from 3 to 4 carbon atoms. Examples of suitable monocyclic cycloalkyl groups include cyclopropyl, cyclobutyl, cyclopentyl, cyclohexyl and cycloheptyl.

The term "alkoxy" includes O-linked hydrocarbon residues including:
linear groups of between 1 and 6 carbon atoms ($C_1$-$C_6$), or of between 1 and 4 carbon atoms ($C_1$-$C_4$). Examples of such alkoxy groups include, but are not limited to, $C_1$-methoxy, $C_2$-ethoxy, $C_3$-n-propoxy and $C_4$-n-butoxy.
branched groups of between 3 and 6 carbon atoms ($C_3$-$C_6$) or of between 3 and 4 carbon atoms ($C_3$-$C_4$). Examples of such alkoxy groups include, but are not limited to, $C_3$-iso-propoxy, and $C_4$-sec-butoxy and tert-butoxy.
each optionally substituted as stated above.

Unless otherwise stated, halo is selected from Cl, F, Br and I.

Aryl is as defined above. Typically, aryl will be optionally substituted with 1, 2 or 3 substituents. Optional substituents are selected from those stated above. Examples of suitable aryl groups include phenyl and naphthyl (each optionally substituted as stated above). Preferably aryl is selected from phenyl, substituted phenyl (substituted as stated above) and naphthyl.

Heteroaryl is as defined above. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above). Preferably heteroaryl is selected from pyridyl, benzothiazole, indole, N-methylindole, thiazole, substituted thiazole, thiophenyl, furyl, pyrazine, pyrazole and substituted pyrazole; wherein substituents are as stated above.

The term "N-linked", such as in "N-linked heterocycloalkyl", means that the heterocycloalkyl group is joined to the remainder of the molecule via a ring nitrogen atom.

The term "O-linked", such as in "O-linked hydrocarbon residue", means that the hydrocarbon residue is joined to the remainder of the molecule via an oxygen atom.

In groups such as —COOR*, "—" denotes the point of attachment of the substituent group to the remainder of the molecule.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, succinates, oxalates, phosphates, esylates, tosylates, benzenesulfonates, naphthalenedisulphonates, maleates, adipates, fumarates, hippurates, camphorates, xinafoates, p-acetamidobenzoates, dihydroxybenzoates, hydroxynaphthoates, succinates, ascorbates, oleates, bisulfates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming pro-drugs are described in 'The Practice of Medicinal Chemistry, $2^{nd}$ Ed. pp 561-585 (2003) and in F. J. Leinweber, *Drug Metab. Res.,* 1987, 18, 379.

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods (e.g. asymmetric synthesis).

In the context of the present invention, references herein to "treatment" include references to curative, palliative and prophylactic treatment.

General Methods

The compounds of formula (I) should be assessed for their biopharmaceutical properties, such as solubility and solution stability (across pH), permeability, etc., in order to select the most appropriate dosage form and route of administration for treatment of the proposed indication. They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Compounds of the invention intended for pharmaceutical use may be administered as a solid or liquid, such as a tablet, capsule or solution. Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Accordingly, the present invention provides a pharmaceutical composition comprising a compound of formula (I) and a pharmaceutically acceptable carrier, diluent or excipient.

For the treatment of conditions such as retinal vascular permeability associated with diabetic retinopathy and diabetic macular edema, the compounds of the invention may be administered in a form suitable for injection into the ocular region of a patient, in particular, in a form suitable for intravitreal injection. It is envisaged that formulations suitable for such use will take the form of sterile solutions of a compound of the invention in a suitable aqueous vehicle. The compositions may be administered to the patient under the supervision of the attending physician.

The compounds of the invention may also be administered directly into the blood stream, into subcutaneous tissue, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous or oily solutions. Where the solution is aqueous, excipients such as sugars (including but not restricted to glucose, manitol, sorbitol, etc.), salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Parenteral formulations may include implants derived from degradable polymers such as polyesters (i.e., polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of co-solvents and/or solubility-enhancing agents such as surfactants, micelle structures and cyclodextrins.

In one embodiment, the compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of the invention in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

For administration to human patients, the total daily dose of the compounds of the invention is typically in the range 0.01 mg and 1000 mg, or between 0.1 mg and 250 mg, or between 1 mg and 50 mg depending, of course, on the mode of administration.

The total dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Synthetic Methods

The compounds of the present invention can be prepared according to the procedures exemplified by the specific examples provided herein below. Moreover, by utilising the procedures described herein, one of ordinary skill in the art can readily prepare additional compounds that fall within the scope of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the invention may be isolated in the form of their pharmaceutically acceptable salts, such as those described previously herein above.

It may be necessary to protect reactive functional groups (e.g. hydroxy, amino, thio or carboxy) in intermediates used in the preparation of compounds of the invention to avoid their unwanted participation in a reaction leading to the formation of the compounds. Conventional protecting groups, for example those described by T. W. Greene and P. G. M. Wuts in "Protective groups in organic chemistry" John Wiley and Sons, 4$^{th}$ Edition, 2006, may be used. For example, a common amino protecting group suitable for use herein is tert-butoxy carbonyl (Boc), which is readily removed by treatment with an acid such as trifluoroacetic acid or hydrogen chloride in an organic solvent such as dichloromethane. Alternatively the amino protecting group may be a benzyloxycarbonyl (Z) group which can be removed by hydrogenation with a palladium catalyst under a hydrogen atmosphere or 9-fluorenylmethyloxycarbonyl (Fmoc) group which can be removed by solutions of secondary organic amines such as diethylamine or piperidine in an organic solvents. Carboxyl groups are typically protected as esters such as methyl, ethyl, benzyl or tert-butyl which can all be removed by hydrolysis in the presence of bases such as lithium or sodium hydroxide. Benzyl protecting groups can also be removed by hydrogenation with a palladium catalyst under a hydrogen atmosphere whilst tert-butyl groups can also be removed by trifluoroacetic acid. Alternatively a trichloroethyl ester protecting group is removed with zinc in acetic acid. A common hydroxy protecting group suitable for use herein is a methyl ether, deprotection conditions comprise refluxing in 48% aqueous HBr for 1-24 hours, or by stirring with borane tribromide in dichloromethane for 1-24 hours. Alternatively where a hydroxy group is protected as a benzyl ether, deprotection conditions comprise hydrogenation with a palladium catalyst under a hydrogen atmosphere.

The compounds according to general formula (I) can be prepared using conventional synthetic methods. For example, an amine may be coupled using standard peptide coupling conditions to an activated alpha carboxylic acid. If present, an additional amine functional group may be suitably amino-protected with a standard protecting group such as tert-butyloxycarbonyl (Boc), benzyloxycarbonyl (Z) or 9-fluorenylmethyloxycarbonyl (Fmoc). The activating group may be N-hydroxysuccinimide. The use of such groups is well known in the art. Other standard peptide coupling methods include the reaction of acids with amines in the presence of hydroxybenzotriazole and carbodiimide such as water soluble carbodiimide, or 2-(1H-benzotriazole-1-yl)-1,1,3,3-tetramethylaminium hexafluorophosphate or benzotriazole-1-yl-oxy-tris-pyrrolidino-phosphoium hexafluorophosphate or bromo-trispyrolidino-phosphoium hexafluorophosphate or 2-(3H-[1,2,3]triazolo[4,5-b]pyridin-3-yl)-1,1,3,3-tetramethylisouronium hexafluorophosphate (V) (HATU) in the presence of organic bases such as triethylamine, diisopropylethylamine or N-methylmorpholine. In a typical second step the protecting group, if present, is removed using standard methods as previously described.

An amine may typically be alkylated or acylated. Acylation may be carried out by treatment with an acylating agent such as an acyl chloride, for example acetyl chloride or benzoyl chloride, in the presence of a base, typically a tertiary amine base such as triethylamine or diisopropylethylamine. Alkylation may typically be carried by treatment with an alkyl halide or by reductive alkylation. Typically, in a reductive alkylation procedure the amine is allowed to react with an aldehyde or ketone in the presence of a suitable reducing agent such as sodium cyanoborohydride or sodium acetoxyborohydride in a suitable solvent such as methanol, at room temperature.

A nitrile compound may typically be reduced by hydrogenation. Conversion may be achieved in a single step either by direct reduction of the nitrile by hydrogenation in a suitable solvent such as methanol in the presence of a suitable catalyst such as palladium on charcoal in the presence of an acid such as hydrochloric acid or reduction with a suitable borohydride in the presence of a suitable transition metal such as cobalt or nickel chloride in a suitable solvent such as methanol at room temperature. Alternatively, the tert-butoxycarbonyl (Boc) protected amine may be isolated (using, for example, the method as described in S. Caddick et al., Tetrahedron Lett., 2000, 41, 3513) and subsequently deprotected by standard means described previously to give the amine.

EXAMPLES

The invention is illustrated by the following non-limiting examples in which the following abbreviations and definitions are used:

| | |
|---|---|
| DCM | Dichloromethane |
| DMA | N,N-Dimethylacetamide |
| DMF | N,N-Dimethylformamide |
| EtOAc | Ethyl Acetate |
| HATU | 2-(3H-[1,2,3]Triazolo[4,5-b]pyridin-3-yl)-1,1,3,3-tetramethylisouronium hexafluorophosphate(V) |
| hrs | Hours |
| HOBt | Hydroxybenzotriazole |
| LCMS | Liquid chromatography mass spectrometry |
| Me | Methyl |
| MeCN | Acetonitrile |
| MeOH | Methanol |
| Min | Minutes |
| MS | Mass spectrum |
| NMR | Nuclear magnetic resonance spectrum - NMR spectra were recorded at a frequency of 400 MHz unless otherwise indicated |
| Pet. Ether | Petroleum ether fraction boiling at 60-80° C. |
| Ph | Phenyl |
| rt | room temperature |
| THF | Tetrahydrofuran |
| TFA | Trifluoroacetic acid |

All reactions were carried out under an atmosphere of nitrogen unless specified otherwise.

$^1$H NMR spectra were recorded on a Bruker (400 MHz) spectrometer with reference to deuterium solvent and at rt.

Molecular ions were obtained using LCMS which was carried out using a Chromolith Speedrod RP-18e column, 50×4.6 mm, with a linear gradient 10% to 90% 0.1% $HCO_2H$/MeCN into 0.1% $HCO_2H/H_2O$ over 13 min, flow rate 1.5 mL/min, or using Agilent, X-Select, acidic, 5-95% MeCN/water over 4 min. Data was collected using a Thermofinnigan Surveyor MSQ mass spectrometer with electospray ionisation in conjunction with a Thermofinnigan Surveyor LC system.

Chemical names were generated using the Autonom software provided as part of the ISIS draw package from MDL Information Systems, or in the IUPAC form using Chemaxon software.

Where products were purified by flash chromatography, 'silica' refers to silica gel for chromatography, 0.035 to 0.070 mm (220 to 440 mesh) (e.g. Merck silica gel 60), and an applied pressure of nitrogen up to 10 p.s.i accelerated column elution. Reverse phase preparative HPLC purifications were carried out using a Waters 2525 binary gradient pumping system at flow rates of typically 20 mL/min using a Waters 2996 photodiode array detector.

All solvents and commercial reagents were used as received.

Methods I to V below describe the synthesis of intermediates useful in the preparation of examples.

I. 6-Aminomethyl-isoquinolin-1-ylamine hydrochloride

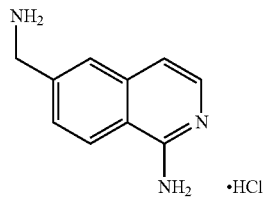 [SMILES: NCc1ccc2c(N)nccc2c1 ; Cl]

A. 2-((E)-2-Dimethylamino-vinyl)-terephthalonitrile ester

Methylterephthalonitrile (1.42 g, 9.99 mmol) and Bredereck's reagent (3.48 g, 19.98 mmol) were dissolved in DMF (15 mL). The reaction mixture was heated at 75° C. under nitrogen for 72 hrs after which time the solvent was removed in vacuo. Trituration with Pet Ether gave a bright yellow solid identified as 2-((E)-2-dimethylamino-vinyl)-terephthalonitrile ester (1.88 g, 0.95 mmol, 95%).

$^1$H NMR (CD$_3$OD) δ: 3.20 (6H, s), 5.34 (1H, d, J=13.4 Hz), 7.21 (1H, dd, J=8.0 Hz, 1.4 Hz), 7.9 (1H, d, 13.4 Hz), 7.61 (1H, d, J=8.0 Hz), 7.94 (1H, d, J=1.2 Hz)

B. 1-Amino-2-(2,4-dimethoxy-benzyl)-1,2-dihydro-isoquinoline-6-carbonitrile 2-((E)-2-Dimethylamino-vinyl)-terephthalonitrile ester (1.85 g, 9.38 mmol) was dissolved in 1,3-dimethyl-3,4,5,6-tetrahydro-2(1H)-pyrimidinone (5 mL) and 2,4-dimethoxy-benzylamine (2.35 g, 14.07 mmol) was added. The reaction mixture was heated at 75° C. under nitrogen. After 3 hrs the reaction mixture was cooled and diethyl ether/Pet Ether (15:85) was added. The yellow solid was filtered off, dried in vacuo, and identified as 1-amino-2-(2,4-dimethoxy-benzyl)-1,2-dihydro-isoquinoline-6-carbonitrile (2.65 g, 8.38 mmol, 89%).

[M+H]+=320.0

$^1$H NMR (CD$_3$OD) δ: 3.85 (3H, s), 3.92 (3H, s), 5.02 (2H, s), 6.39 (1H, d, J=7.4 Hz), 6.57 (1H, dd, J=8.4 Hz, 2.4 Hz), 6.66 (1H, d, 2.4 Hz), 7.18 (1H, d, 8.4 Hz), 7.24 (1H, d, 7.4 Hz), 7.72 (1H, dd, J=8.5 Hz, 1.4 Hz), 7.93 (1H,s), 8.45 (1H, d, J=8.5 Hz)

C. 1-Amino-isoquinoline-6-carbonitrile

1-Amino-2-(2,4-dimethoxy-benzyl)-1,2-dihydro-isoquinoline-6-carbonitrile (1.6 g, 5.0 mmol) was dissolved in anisole (17 mL) and trifluoroacetic acid (20 mL). The reaction mixture was heated at 105° C. under nitrogen for 12 hrs after which time the reaction mixture was cooled, diethyl ether/Pet Ether (3:7) was added, the resultant solid was filtered off, dried in vacuo and identified as 1-amino-isoquinoline-6-carbonitrile (770 mg, 4.54 mmol, 91%).

[M+H]+=170.0

$^1$H NMR (CD$_3$OD) δ: 7.23-7.25 (1H, d, J=6.9 Hz), 7.65 (1H, d, J=6.8 Hz), 8.11 (1H, dd, J=8.7 Hz, 1.6 Hz), 8.33 (1H, s), 8.45 (1H, d, J=8.7 Hz).

D. (1-Amino-isoquinolin-6-ylmethyl)-carbamic Acid tert-butyl ester

1-Amino-isoquinoline-6-carbonitrile (200 mg, 1.18 mmol) was dissolved in methanol (20 mL). This solution was cooled to 0° C. Nickel (II) chloride hexahydrate (28 mg, 0.12 mmol) and di-tertbutyl dicarbonate (516 g, 2.36 mmol) were added followed by sodium borohydride (313 g, 8.22 mmol) portionwise. The reaction mixture was stirred at 0° C. to room temp for 3 days. The MeOH was removed by evaporation. The residue was dissolved in CHCl$_3$ (70 ml), washed with sat NaHCO$_3$ (1×30 mL), water (1×30 mL), brine (1×30 mL), dried (Na$_2$SO$_4$) and evaporated in vacuo to give a yellow oil identified as (1-amino-isoquinolin-6-ylmethyl)-carbamic acid tert-butyl ester (110 mg, 0.4 mmol, 34%).

[M+H]$^+$=274.1.

E. 6-Aminomethyl-isoquinolin-1-ylamine Hydrochloride (1-Amino-isoquinolin-6-ylmethyl)-carbamic acid tert-butyl ester (110 mg, 0.40 mmol) was dissolved in 4M HCl in dioxan (40 mL). After 18 hrs at room temperature the solvent was removed in vacuo to give a pale brown solid identified as 6-aminomethyl-isoquinolin-1-ylamine hydrochloride (67 mg, 0.39 mmol, 96%).

[M+H]+=174.3

II. C-(4,6-Dimethyl-1H-pyrrolo[2,3-b]pyridin-5-yl)-methylamine hydrochloride

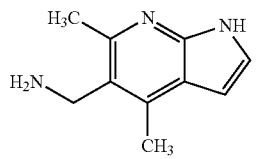

A. 1-tert-Butyl-4,6-dimethyl-1H-pyrrolo[2,3-b]pyridine-3-carbonitrile

A mixture of 5-amino-1-tert-butyl-1H-pyrrole-3-carbonitrile (2.6 g, 15.93 mmol) and pentane-2,4-dione (1.595 g, 15.93 mmol,) were dissolved in ethanol (80 mL) and concentrated HCl (0.2 mL) was added. The reaction mixture was heated at reflux for 18 hrs. The mixture was concentrated in vacuo and the crude purified by flash chromatography (silica) eluting in step gradients 95:5 to 9:1 Pet. Ether/ethyl acetate to give a yellow oil identified as 1-tert-butyl-4,6-dimethyl-1H-pyrrolo[2,3-b]pyridine-3-carbonitrile (3.05 g, 13 mmol, 84% yield).

[M+H]$^+$=228.4
$^1$H NMR: (CDCl$_3$), δ: 1.81 (9H, s), 2.58 (3H, s), 2.70 (3H, s), 6.84 (1H, s), 7.75 (1H, s)

B. 5-Bromo-1-tert-butyl-4,6-dimethyl-1H-pyrrolo[2,3-b]pyridine-3-carbonitrile

A solution of 1-tert-butyl-4,6-dimethyl-1H-pyrrolo[2,3-b]pyridine-3-carbonitrile (2.820 g, 12.4 mmol) in dichloromethane (50 mL) under an atmosphere of N$_2$ was cooled to at least −5° C. (Ice/NaCl, 3:1). 1,3-Dibromo-5,5-dimethylhydantoin (1.774 g, 6.203 mmol) was then added and the reaction was stirred at −5° C. or below. After stirring at −5° C. further 1,3-dibromo-5,5-dimethylhydantoin (88 mg, 0.31 mmol) was added and stirring continued at −5° C. for a further 3 hrs The reaction mixture was quenched with Na$_2$SO$_3$ (aq) before warming the reaction to rt. 1M NaOH was added and the layers separated. The aqueous phase was extracted with dichloromethane (2×10 mL), the combined organic extracts were washed with brine (2×10 mL) and concentrated in vacuo. The crude product was purified by flash column chromatography on silica eluting with Pet. Ether/ethyl acetate 95:5. Fractions containing product were concentrated and the residue recrystalised from ethyl acetate/Pet. Ether to give a white solid identified as 5-bromo-1-tert-butyl-4,6-dimethyl-1H-pyrrolo[2,3-b]pyridine-3-carbonitrile (3.19 g, 10.42 mmol, 84% yield).

[M+H]$^+$=305.7
$^1$H NMR: (CDCl$_3$), δ: 1.81 (9H, s), 2.78 (3H, s), 2.82 (3H, s), 7.78 (1H, s)

C. 5-Bromo-4,6-dimethyl-1H-pyrrolo[2,3-]pyridine-3-carbonitrile

5-Bromo-1-(tert-butyl)-4,6-dimethyl-1H-pyrrolo[2,3-b]pyridine-3-carbonitrile (2.1 g, 6.87 mmol) was added portionwise to a stirring suspension of aluminum trichloride (2.75 g, 20.6 mmol) in chlorobenzene (160 mL). After the addition, the mixture was heated to 100° C. overnight forming a black gummy solution. After 24 hrs, the reaction was allowed to cool then poured into water (300 mL) and dichloromethane (300 mL). The mixture was treated cautiously with conc. HCl (135 mL) and the mixture stirred for 10 min then filtered, washing with water and dichloromethane. The resultant solid was dried under vacuum in the presence of CaCl$_2$ over a weekend to give a pale grey solid identified as 5-bromo-4,6-dimethyl-1H-pyrrolo[2,3-b]pyridine-3-carbonitrile (1.56 mg, 6.16 mmol, 90% yield).

D. 5-Bromo-4,6-dimethyl-1H-pyrrolo[2,3-b]pyridine

A suspension of 5-bromo-4,6-dimethyl-1H-pyrrolo[2,3-b]pyridine-3-carbonitrile (1.56 g, 6.16 mmol) in conc. hydrochloric acid, 37% (235 mL) was heated at reflux overnight. Further conc. HCl (100 mL) was added and the reaction was heated at reflux for a further 20 hrs. The mixture was cooled and poured into ice-water (1 L) and neutralised with 2N NaOH until pH 9, forming a precipitate. This was filtered, washed with water then dried under vacuum in the presence of CaCl$_2$ to give a grey solid identified as 5-bromo-4,6-dimethyl-1H-pyrrolo[2,3-b]pyridine (1.3 g, 5.72 mmol, 92% yield).

[M+H]$^+$=225.1
$^1$H NMR: (CDCl$_3$), δ: 2.66 (3H, s), 2.82 (3H, s), 6.49 (1H, dd, J=3.5, 2.1 Hz), 7.29 (1H, dd, J=3.4, 2.7 Hz), 11.14 (1H, br.s)

E. 4,6-Dimethyl-1H-pyrrolo[2,3-b]pyridine-5-carbonitrile

5-Bromo-4,6-dimethyl-1H-pyrrolo[2,3-b]pyridine (1.3 g, 5.72 mmol) was dissolved in N,N-dimethylacetamide (20 mL). The solution was degassed with N$_2$ before the addition of zinc powder (45 mg, 0.693 mmol), zinc acetate (127 mg, 0.693 mmol), 1,1'-bis(diphenylphosphino)ferrocene (128 mg, 0.23 mmol), Zn(CN)$_2$ (339 mg, 2.888 mmol) and tris(dibenzylideneacetone)dipalladium(0) (106 mg, 0.116 mmol). The reaction was heated at 120° C. for 48 hrs. After cooling to rt the reaction was diluted with ethyl acetate and washed with 2M NH$_4$OH and brine. Organic layer was dried over MgSO4 and filtered. After concentration in vacuo crude product was purified by flash column chromatography on silica eluting with 9:1, 8:2, 7:3, 1:1. (Pet. Ether/Ethyl acetate). Fractions were collected and concentrated in vacuo.

The yellow solid was triturated in diethyl ether to give an off white solid identified as 4,6-dimethyl-1H-pyrrolo[2,3-b]pyridine-5-carbonitrile (660 mg, 3.83 mmol, 67% yield).

[M+H]$^+$=172.1

$^1$H NMR: (CDCl$_3$), δ: 2.76 (3H, s), 2.86 (3H, s), 6.59 (1H, dd, J=3.5, 2.0 Hz), 7.36 (1H, dd, J=3.5, 2.4 Hz), 10.86 (1H, br.s)

F. (4,6-Dimethyl-1H-pyrrolo[2,3-b]pyridine-5-ylmethyl)-carbamic Acid tert-butyl ester 4,6-Dimethyl-1H-pyrrolo[2,3-b]pyridine-5-carbonitrile (610 mg, 3.56 mmol) was dissolved in methanol (75 mL). This solution was cooled to 0° C. Nickel (II) chloride hexahydrate (85 mg, 0.36 mmol) and di-tertbutyl dicarbonate (1.56 g, 7.13 mmol) were added followed by sodium borohydride (943 mg, 24.94 mmol) portionwise. The reaction mixture was stirred at 0° C. to room temp for 18 hrs. The MeOH was removed by evaporation. The residue was dissolved in CHCl$_3$ (70 mL), washed with sat NaHCO$_3$ (1×30 mL), water (1×30 mL) and brine (1×30 mL), dried (Na$_2$SO$_4$) and evaporated in vacuo to give a yellow oil. Purified by flash chromatography, (silica), eluant 40% Pet. Ether, 60% EtOAc to give white solid identified as identified as (4,6-dimethyl-1H-pyrrolo[2,3-b]pyridin-5-ylmethyl)-carbamic acid tert-butyl ester (710 mg, 2.56 mmol, 72% yield).

[M+H]$^+$=276.1

$^1$H NMR: (CDCl$_3$), 1.49 (9H, s), 2.61 (3H, s), 2.71 (3H, s), 4.46 (1H, br.s), 4.51 (2H, d, J=4.4 Hz), 6.50 (1H, dd, J=3.5, 2.0 Hz), 7.25 (1H, dd, J=3.4, 2.5 Hz), 9.64 (1H, br.s).

G. C-(4,6-Dimethyl-1H-pyrrolo[2,3-b]pyridin-5-yl)-methylamine hydrochloride 4,6-Dimethyl-1H-pyrrolo[2,3-b]pyridin-5-ylmethyl)-carbamic acid tert-butyl ester (710 mg, 2.56 mmol) was dissolved in 4M HCl in dioxane (10 mL). After 2 hrs at rt the solvent was removed in vacuo to give a yellow solid identified as C-(4,6-Dimethyl-1H-pyrrolo[2,3-b]pyridin-5-yl)-methylamine hydrochloride (360 mg, 2.00 mmol, 80% yield).

[M+H]$^+$=176.4

$^1$H NMR: (d6-DMSO), 2.53 (3H, s), 2.60 (3H, s), 3.94 (2H, s), 4.76 (2H, br.s), 6.43 (1H, d, J=2.3 Hz), 7.28 (1H, dd, J=3.2, 1.9 Hz), 11.32 (1H, br.s)

III. (4-Aminomethyl-3,5-dimethyl-benzyl)-carbamic Acid tert-butyl ester

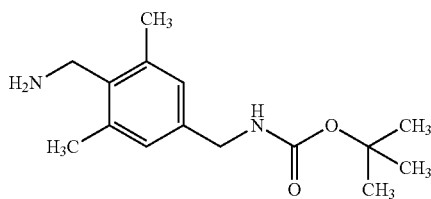 [SMILES: Cc1cc(CNC(=O)OC(C)(C)C)cc(C)c1CN]

A. (4-Bromo-2,6-dimethyl-benzyl)-carbamic Acid tert-butyl ester

4-Bromo-2,6-dimethylbenzonitrile (2.5 g, 11.9 mmol) was dissolved in methanol (150 mls). This solution was cooled to 0° C. Nickel (II) chloride hexahydrate (238 mg, 1.19 mmol) and di-tertbutyl dicarbonate (5.19 g, 23.80 mmol) were added followed by sodium borohydride (3.15 g, 83.30 mmol) portionwise. The reaction mixture was stirred at 0° C. to room temp for 3 days. The MeOH was removed by evaporation. The residue was dissolved in CHCl$_3$ (70 mls), washed with sat NaHCO$_3$ (1×30 mls), water (1×30 mls), brine (1×30 mls), dried (Na$_2$SO$_4$) and evaporated in vacuo to give a colourless oil identified as (4-bromo-2,6-dimethyl-benzyl)-carbamic acid tert-butyl ester (3.0 g, 9.55 mmol, 80%).

B. (4-Cyano-2,6-dimethyl-benzyl)-carbamic Acid tert-butyl ester

To a degassed solution of (4-bromo-2,6-dimethyl-benzyl)-carbamic acid tert-butyl ester (3.0 g, 9.55 mmol) in N,N-dimethylacetamide (30 mls) was added zinc powder (75 mg, 1.15 mmol), zinc acetate (210 mg, 1.15 mmol), 1,1'-bis(diphenylphosphino) ferrocene (635 mg, 1.15 mmol), zinc cyanide (560 mg, 4.77 mmol), and tris(dibenzylideneacetone) dipalladium(0) (524 mg, 0.57 mmol). The reaction was heated at 120° C. for 4 hrs. After which the reaction mixture was cooled to room temperature and extra 1,1'-bis(diphenylphosphino) ferrocene (423 mg, 0.77 mmol) and tris(dibenzylideneacetone) dipalladium(0) (350 mg, 0.38 mmol) were added and the reaction was heated at 120° C. for a further 28 hrs. The reaction mixture was cooled to RT filtered through celite and washed with ethyl acetate (250 mls). The filtrate washed with sat NaHCO$_3$ (1×30 mls), water (1×30 mls), brine (1×30 mls), dried (Na$_2$SO$_4$) and evaporated in vacuo. The residue was purified by flash chromatography, (silica), eluant 80% Pet. Ether (60-80° C.), 20% EtOAc to give an off white solid identified as (4-cyano-2,6-dimethyl-benzyl)-carbamic acid tert-butyl ester (630 mg, 2.42 mmol, 25%).

[M+H]$^+$=261.06.

C. 4-Aminomethyl-3,5-dimethyl-benzonitrile Hydrochloride (4-Cyano-2,6-dimethyl-benzyl)-carbamic acid tert-butyl ester (630 mg, 2.42 mmol) was dissolved in 4M HCl in dioxan (10 mls). After one hour at room temperature the solvent was removed in vacuo to give a pale brown solid identified as 4-aminomethyl-3,5-dimethyl-benzonitrile hydrochloride (470 mg, 2.39 mmol, 99%).

D. (4-Cyano-2,6-dimethyl-benzyl)-carbamic Acid benzyl ester

4-Aminomethyl-3,5-dimethyl-benzonitrile hydrochloride (470 mg, 2.39 mmol) was dissolved in dichloromethane (50 mls) and the solution was cooled to 0° C. N,N-Diisopropylethylamine (679 mg, 5.26 mmol) was added followed by benzyl chloroformate (489 mg, 2.87 mmol) was added. After one hour at 0° C. to room temperature the reaction mixture was diluted with chloroform, this solution was washed with sat NaHCO$_3$ (1×30 mls), water (1×30 mls), brine (1×30 mls), dried (Na$_2$SO$_4$) and evaporated in vacuo to give a brown oil identified as (4-cyano-2,6-dimethyl-benzyl)-carbamic acid benzyl ester (700 mg, 2.38 mmol, 99%).

[M+H]$^+$=295.04

E. [4-(tert-Butoxycarbonylamino-methyl)-2,6-dimethyl-benzyl]-carbamic Acid benzyl ester (4-Cyano-2,6-dimethyl-benzyl)-carbamic acid benzyl ester (700 mg, 2.38 mmol) was dissolved in methanol (75 mls). This solution was cooled to 0° C. Nickel (II) chloride hexahydrate (57 mg, 0.24 mmol) and di-tertbutyl dicarbonate (1.04 g, 4.76 mmol) were added followed by sodium borohydride (630 mg, 16.65 mmol) portionwise. The reaction mixture was stirred at 0° C. to room temp for 3 days. The MeOH was removed by evaporation. The residue was dissolved in $CHCl_3$ (70 ml), washed with sat $NaHCO_3$ (1×30 mls), water (1×30 mls), brine (1×30 mls), dried ($Na_2SO_4$) and evaporated in vacuo. The residue was purified by flash chromatography, (silica), eluant 65% Pet. Ether (60-80° C.), 35% EtOAc to give an off white solid identified as [4-(tert-butoxycarbonylamino-methyl)-2,6-dimethyl-benzyl]-carbamic acid benzyl ester (600 mg, 1.51 mmol, 63%).

m/z=421.05 (M+Na).

F. (4-Aminomethyl-3,5-dimethyl-benzyl)-carbamic Acid tert-butyl ester

[4-(tert-Butoxycarbonylamino-methyl)-2,6-dimethyl-benzyl]-carbamic acid benzyl ester (600 mg, 1.51 mmol) was dissolved in methanol (60 mls). This solution was hydrogenated over 10% Pd/C (100 mg) at atmospheric pressure and room temperature for one hour after which time the catalyst was filtered off and washed with methanol (30 mls), the combined filtrates were evaporated in vacuo to give a white solid identified as (4-aminomethyl-3,5-dimethyl-benzyl)-carbamic acid tert-butyl ester (350 mg, 1.32 mmol, 88%).

m/z=287.07 (M+Na).

IV. 5-((2-Phenylthiazol-4-yl)methyl)nicotinic Acid

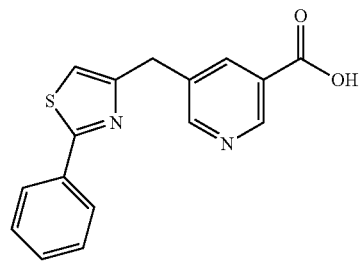 [SMILES: O=C(O)c1cncc(Cc2csc(-c3ccccc3)n2)c1]

A. Methyl 5-((2-phenylthiazol-4-yl)methyl)nicotinate

To a microwave vial was added: (5-(methoxycarbonyl) pyridin-3-yl)boronic acid (540 mg, 2.089 mmol), potassium carbonate (412 mg, 2.98 mmol), 4-(bromomethyl)-2-phenylthiazole (379 mg, 1.492 mmol), THF (3 mL) and water (0.3 mL). The mixture was degassed for 10 mins before $Pd(Ph_3)_4$ catalyst (172 mg, 0.149 mmol) was added. Heated in the CEM Discover microwave at 80° C./300 W for 20 mins. Reaction mixture was diluted with EtOAc (80 mL) and water (50 mL). The organic extracts were combined and washed with saturated brine (50 mL) and then dried over $MgSO_4$, filtered and concentrated in vacuo. The crude product was purified by chromatography (20-60% EtOAc in isohexanes) to afford methyl 5-((2-phenylthiazol-4-yl) methyl)nicotinate (184 mg, 0.545 mmol, 36.6% yield) as a yellow viscous oil.

$[M+H]^+$=311.1

B. 5-((2-Phenylthiazol-4-yl)methyl)nicotinic Acid

To a stirred solution of methyl 5-((2-phenylthiazol-4-yl) methyl)nicotinate (189 mg, 0.609 mmol) in THF (4 mL) and MeOH (2 mL) was added NaOH 2M (913 µl, 1.827 mmol) and left at rt for 1.5 hrs. Reaction mixture was acidified by the addition of acetic acid (3 mL) and solvent removed under vacuum. Azeotroped with toluene (2×30 mL) to remove acetic acid to give 5-((2-phenylthiazol-4-yl)methyl)nicotinic acid (98 mg, 0.298 mmol, 48.9% yield) as an off-white solid.

$[M+H]^+$=297.1

V. 1-(4-(Bromomethyl)benzyl)-4-methyl-1H-pyrazole

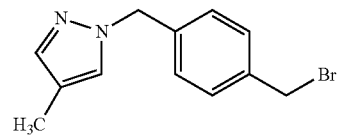

A. (4-((4-Methyl-1H-pyrazol-1-yl)methyl)phenyl) methanol

To a round bottom flask under $N_2$ was added: (4-(chloromethyl)phenyl)methanol (10.04 g, 60.9 mmol), 4-methyl-1H-pyrazole (5.05 ml, 60.9 mmol) and dry MeCN (100 mL). Next, potassium carbonate (9.26 g, 67.0 mmol) was added and the white suspension was heated to 60° C. for 18 h. The volatiles were removed in vacuo. The residue was partitioned between EtOAc (100 mL) and water (150 mL). Aqueous layer was neutralised to pH 7 with 1 N HCl and extracted with EtOAc (2×100 mL). The combined organic layers were washed with water (100 mL), brine (50 mL) then dried ($MgSO_4$), filtered and concentrated in vacuo. The crude product was purified by chromatography (10-80% EtOAc in iso-hexanes) to afford (4-((4-methyl-1H-pyrazol-1-yl)methyl)phenyl)methanol (2.9 g, 14.05 mmol, 23.07% yield) as a free-flowing oil that solidified on standing.

$[M+H]^+$=203.2

B. 1-(4-(Bromomethyl)benzyl)-4-methyl-1H-pyrazole

To a flask under $N_2$ was added: (4-((4-methyl-1H-pyrazol-1-yl)methyl)phenyl)methanol (250 mg, 1.236 mmol), triphenylphosphine (373 mg, 1.421 mmol) and dry DCM (5.0 mL). Cooled in an ice bath before perbromomethane (451 mg, 1.360 mmol) was added. Stirred at rt for 1 h. Concentrated in vacuo and purified by column chromatography (0-20% EtOAc in iso-hexanes) to afford 1-(4-(bromomethyl)benzyl)-4-methyl-1H-pyrazole (0.33 g, 1.182 mmol, 96% yield) as an oil that solidified on standing to a white solid.

$[M+H]^+$=265.1/267.1

Example 1

N-[(1-Aminoisoquinolin-6-yl)methyl]-({4-[(4-methylpyrazol-1-yl)methyl]phenyl}methyl)pyridine-3-carboxamide

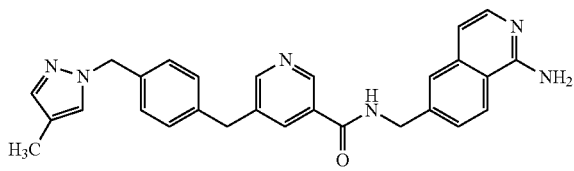 [SMILES: Cc1cnn(Cc2ccc(Cc3cncc(C(=O)NCc4ccc5c(N)nccc5c4)c3)cc2)c1]

A. 5-(4,4,5,5-Tetramethyl-[1,3,2]dioxaborolan-2-yl)-nicotinic Acid methyl ester To a dried flask under N2 was added: 4,4,4',4',5,5,5',5'-octamethyl-2,2'-bi(1,3,2-dioxaborolane) (0.441 g, 1.736 mmol), methyl 5-bromonicotinate (0.25 g, 1.157 mmol), potassium acetate (0.341 g, 3.47 mmol) and dry dioxane (10 mL). The reaction was degassed under nitrogen for 5 minutes before Pd(dppf)Cl$_2$ (0.085 g, 0.116 mmol) was added to give a bright red solution. The reaction was heated to 80° C. for 16 h. The reaction mixture was partitioned between EtOAc (50 mL) and sat. aq. NH$_4$Cl (30 mL). The aqueous layer was extracted with EtOAc (2×30 mL). The combined organic layers were washed with water (30 mL) then brine (20 mL) and dried (MgSO4), filtered and concentrated in vacuo to a brown oil which was used in the next step without further purification.

B. 5-[4-(4-Methyl-pyrazol-1-ylmethyl)-benzyl]-nicotinic Acid methyl ester

To a microwave vial was added: methyl 5-(4,4,5,5-tetramethyl-1,3,2-dioxaborolan-2-yl)nicotinate (0.5 g, 0.760 mmol), potassium carbonate (0.150 g, 1.086 mmol), 1-(4-(bromomethyl)benzyl)-4-methyl-1H-pyrazole (0.144 g, 0.543 mmol), THF (10 mL) and water (1.0 mL). The solvent was degassed for 10 mins before Pd(PPh$_3$)$_4$ (0.063 g, 0.054 mmol) was added. The reaction was heated in a microwave at 80° C. for 20 mins, after which time LC-MS showed complete conversion to product. The reaction mixture was partitioned between EtOAc (50 mL) and water (20 mL). The organic layer was separated and washed with water (20 mL), brine (20 mL) then dried (MgSO4), filtered and concentrated in vacuo. The crude was purified by column chromatography (12 g RediSep, 0-80% EtOAc in iso-hexanes) and the product dried under vacuum (40° C.) for 1 h. 5-[4-(4-Methyl-pyrazol-1-ylmethyl)-benzyl]-nicotinic acid methyl ester was identified as a brown (151 mg, 0.460 mmol, 85% yield).
[M+H]$^+$=322.2

C. 5-[4-4-(4-Methyl-pyrazol-1-ylmethyl)-benzyl]-nicotinic Acid

To a round bottom flask was added: methyl 5-(4-((4-methyl-1H-pyrazol-1-yl)methyl)benzyl)nicotinate (0.19 g, 0.591 mmol), THF (7.0 mL), MeOH (3.0 mL) then lithium hydroxide (0.042 g, 1.774 mmol) in water (3.0 mL). The light brown solution heated to 65° C. for 1 hour. The reaction mixture was partitioned between EtOAc (20 mL) and water (20 mL). The aqueous layer was concentrated in vacuo to a black oil, acidified to pH 3 with 1 N HCl and extracted with EtOAc (4×30 mL). The combined organic layers were washed with water (25 mL), brine (20 mL), dried (Na2SO4), filtered then concentrated in vacuo to a pale yellow solid. The product was dried under vacuum (40° C.) overnight to afford 5-[4-(4-methyl-pyrazol-1-ylmethyl)-benzyl]-nicotinic acid as a pale yellow powder (0.145 g, 0.462 mmol, 78% yield).
[M+H]$^+$=308.2

D. N-(1-Amino-isoquinolin-6-ylmethyl)-5-[4-(4-methyl-pyrazol-1-ylmethyl)-benzyl]-nicotinamide To a vial was added: 5-(4-((4-methyl-1H-pyrazol-1-yl)methyl)benzyl)nicotinic acid (45 mg, 0.146 mmol), 6-(aminomethyl)isoquinolin-1-amine (26.6 mg, 0.154 mmol), HATU (61.2 mg, 0.161 mmol) and DCM (3.0 mL) to give an orange suspension. Next, DIPEA (77 µl, 0.439 mmol) was added to give a pale orange solution. Stirred at room temperature for 2 hrs over which time an orange precipitate formed. LC-MS showed complete conversion to desired product. The reaction mixture was partitioned between DCM (10 mL) and sat. NH$_4$Cl (20 mL). MeOH (1 mL) was added to aid solubility. The aqueous layer was extracted with DCM (10 mL) and the combined organic layers were washed with water (10 mL) and dried (Na2SO4), filtered and concentrated in vacuo. The crude product was purified by chromatography on RediSep (12 g column, 0-10% MeOH (1% NH3) in DCM). The product was dried in a dessicator overnight to afford an off-white solid (57 mg, 0.121 mmol, 82% yield) identified as N-(1-amino-isoquinolin-6-ylmethyl)-5-[4-(4-methyl-pyrazol-1-ylmethyl)-benzyl]-nicotinamide
[M+H]=463.3
$^1$H NMR (d6-DMSO) δ: 1.97 (3H, s), 4.01 (2H, s), 4.60 (2H, d, J=5.9 Hz), 5.18 (2H, s), 6.71 (2H, br.s), 6.86 (1H, d, J=5.6 Hz), 7.13 (2H, d, J=8.2 Hz), 7.21-7.24 (3H, m), 7.40 (1H, dd, J=1.7, 8.6 Hz), 7.50 (1H, t, J=0.8 Hz), 7.56 (1H, br.s), 7.76 (1H, d, J=5.8 Hz), 8.06 (1H, t, J=2.1 Hz), 8.13 (1H, d, J=8.6 Hz), 8.63 (1H, d, J=2.1 Hz), 8.91 (1H, d, J=2.1 Hz), 9.27 (1H, t, J=5.9 Hz).

Example 2

5-({4-[(4-Methylpyrazol-1-yl)methyl]phenyl}methyl)-N-{7H-pyrrolo[2,3-b]pyridin-3-ylmethyl}pyridine-3-carboxamide

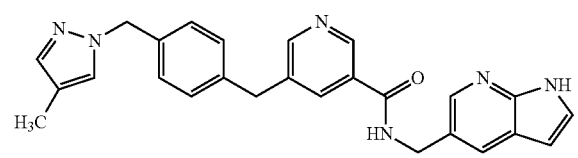 [SMILES: Cc1cnn(Cc2ccc(Cc3cncc(C(=O)NCc4cnc5[nH]ccc5c4)c3)cc2)c1]

To a vial was added: 5-(4-((4-methyl-1H-pyrazol-1-yl)methyl)benzyl)nicotinic acid (48 mg, 0.156 mmol), (1H-pyrrolo[2,3-b]pyridin-5-yl)methanamine hydrochloride (28.7 mg, 0.156 mmol), HATU (65.3 mg, 0.172 mmol) and DCM (3.0 mL) to give a white suspension. Next, DIPEA (82 µl, 0.469 mmol) was added to give a colourless solution. The reaction was stirred at rt for 2 hrs over which time the colour changed to orange. LC-MS showed complete conversion to desired product. The reaction was partitioned between DCM (10 mL) and sat. NH₄Cl (20 mL). MeOH (1 mL) was added to aid solubility. The aqueous layer was extracted with DCM (10 mL) before the combined organic layers were washed with water (10 mL) and dried (Na₂SO₄), filtered and concentrated in vacuo. The crude product was purified by chromatography on RediSep (12 g column, 0-10% MeOH (NH3) in DCM) and dried in a dessicator overnight. The product was isolated as a white solid and identified as 5-[4-(4-methyl-pyrazol-1-ylmethyl)-benzyl]-N-(1H-pyrrolo[2,3-b]pyridin-5-ylmethyl)-nicotinamide (57 mg, 0.128 mmol, 82% yield).

m/z 437.3 (M+H)+(ES+) at 1.49

NMR (d6-DMSO) δ: 1.97 (3H, s), 3.99 (2H, s), 4.55 (2H, d, J=5.8 Hz), 5.17 (2H, s), 6.41 (1H, dd, J=1.9, 3.4 Hz), 7.12 (2H, d, J=8.2 Hz), 7.21-7.23 (3H, m), 7.44 (1H, dd, J=2.7, 3.2 Hz), 7.50 (1H, t, J=0.7 Hz), 7.88 (1H, d, J=1.6 Hz), 8.03 (1H, t, J=2.1 Hz), 8.20 (1H, d, J=2.0 Hz), 8.60 (1H, d, J=2.0 Hz), 8.87 (1H, d, J=2.0 Hz), 9.17 (1H, t, J=5.6 Hz), 11.57 (1H, s).

Example 3

N-[(1-Aminoisoquinolin-6-yl)methyl]-4-({4-[(4-methylpyrazol-1-yl)methyl]phenyl}methyl)pyridine-2-carboxamide

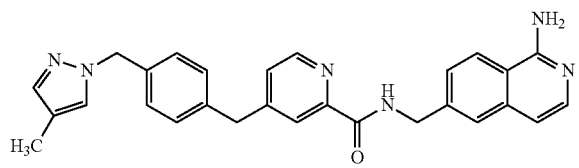 [SMILES: Cc1cnn(Cc2ccc(Cc3ccnc(C(=O)NCc4ccc5c(N)nccc5c4)c3)cc2)c1]

A. 4-(4,4,5,5-Tetramethyl-[1,3,2]dioxaborolan-2-yl-pyridine-2-carboxylic Acid methyl ester To an oven dried flask was added: methyl 4-bromopicolinate (0.5 g, 2.314 mmol), 4,4,4',4',5,5,5',5'-octamethyl-2,2'-bi(1,3,2-dioxaborolane) (0.705 g, 2.78 mmol), potassium acetate (0.681 g, 6.94 mmol) and dry dioxane (20 mL). The solvent was degassed (N₂) for 10 minutes before PdCl₂(dppf) (0.085 g, 0.116 mmol) was added. The dark red solution was heated to 80° C. (base-plate temp.) for 20 h. The reaction mixture was partitioned between EtOAc (100 mL) and sat. aq. NH₄Cl (50 mL). The aqueous layer was extracted with EtOAc (2×30 mL). The combined organic layers were washed with water (3×30 mL) then brine (20 mL), dried (MgSO4) and filtered. Concentration in vacuo afforded a brown oil identified as 4-(4,4,5,5-tetramethyl-[1,3,2]dioxaborolan-2-yl)-pyridine-2-carboxylic acid methyl ester (1.0 g, 2.281 mmol, 99% yield). The product was used in subsequent reaction without further purification

[M+H]⁺=182.1

B. 4-[4-(4-Methyl-pyrazol-1-ylmethyl)-benzyl]-pyridine-2-carboxylic Acid methyl ester To a microwave vial was added: methyl 4-(4,4,5,5-tetramethyl-1,3,2-dioxaborolan-2-yl)picolinate (0.77 g, 1.756 mmol), potassium carbonate (0.347 g, 2.509 mmol), 1-(4-(bromomethyl)benzyl)-4-methyl-1H-pyrazole (0.333 g, 1.254 mmol), THF (10.0 mL) and water (0.5 mL). The solvent was degassed with N₂ for 10 mins before Pd(PPh₃)₄ (0.072 g, 0.063 mmol) was added. The reaction was heated to 80° C. in the microwave for 35 minutes. The reaction mixture was partitioned between EtOAc (50 mL) and water (30 mL). The aqueous layer was extracted with EtOAc (2×30 mL). The combined organic layers were washed with water (3×20 mL) then brine (20 mL) and dried (MgSO4), filtered and concentrated in vacuo. The crude material was purified by column chromatography (40 g RediSep, dry loaded. 10-100% EtOAc in iso-hexanes). The product eluted at 100% EtOAc to afford a brown solid identified as 4-[4-(4-(4-methyl-pyrazol-1-ylmethyl)-benzyl]-pyridine-2-carboxylic acid methyl ester (0.111 g, 0.321 mmol, 25.6% yield)

[M+H]⁺=322.2

C. 4-[4-(4-Methyl-pyrazol-1-ylmethyl)-benzyl]-pyridine-2-carboxylic Acid

To a round bottom flask was added: methyl 4-(4-((4-methyl-1H-pyrazol-1-yl)methyl)benzyl)picolinate (0.19 g, 0.503 mmol), THF (6.0 mL), MeOH (2.0 mL) and lithium hydroxide (0.036 g, 1.508 mmol) as a solution in water (2.0 mL). The resulting brown solution was heated to 65° C. for 1 hour. LC-MS showed complete conversion to desired acid. The reaction mixture was concentrated in vacuo then partitioned between EtOAc (20 mL) and water (20 mL). The aqueous was acidified to pH 4-5 with 1 N HCl and the layer was extracted with EtOAc (3×30 mL). The product was sparingly soluble. The combined organic layers were washed with water (25 mL) then concentrated in vacuo to afford a white solid. The solid was azeotroped with toluene (2×20 mL) to remove water. The product was dried in a vacuum oven (40° C.) over the weekend to afford an off white solid identified as 4-[4-(4-methyl-pyrazol-1-ylmethyl)-benzyl]-pyridine-2-carboxylic acid (0.3 g, 0.436 mmol, 87% yield).

[M+H]⁺=308.2

D. 4-[4-(4-(4-Methyl-pyrazol-1-ylmethyl)-benzyl]-pyridine-2-carboxylic Acid (1-amino-isoquinolin-6-ylmethyl)-amide To a vial was added: 4-(4-((4-methyl-1H-pyrazol-1-yl)methyl)benzyl)picolinic acid (50 mg, 0.065 mmol), 6-(aminomethyl)isoquinolin-1-amine (11.27 mg, 0.065 mmol), HATU (27.2 mg, 0.072 mmol) and dry DCM (2.5 mL). Next, DIPEA (114 µl, 0.651 mmol) was added and the reaction was stirred at room temperature. LC-MS after 1 hour showed complete conversion to the desired product. The reaction mixture was partitioned between DCM (20 mL) and sat. aq. NH₄Cl (20 mL). The aqueous layer was extracted with DCM (2×20 mL). The combined organic layers were washed with water (20 mL), then brine (20 mL) and dried (Na₂SO₄), filtered then concentrated in vacuo. The crude was purified by column chromatography (4 g RediSep, dry loaded, 0-10% MeOH (1% NH₃) in DCM). The pure product was dried in a vacuum oven overnight to afford a colourless glass identified as 4-[4-(4-(4-methyl-pyrazol-1-ylmethyl)-benzyl]-pyridine-2-carboxylic acid (1-amino-isoquinolin-6-ylmethyl)-amide (7.7 mg, 0.013 mmol, 20.47% yield).

[M+H]⁺=463.2

NMR (d6-DMSO) δ: 1.98 (3H, s), 4.05 (2H, s), 4.60 (2H, d, J=6.4 Hz), 5.19 (2H, s), 5.75 (2H, s), 6.90 (1H, d, J=6.0 Hz), 7.13-7.15 (2H, m), 7.22-7.25 (2H, m), 7.47 (1H, dd, J=1.7, 5.0 Hz), 7.50-7.51 (1H, m), 7.57 (1H, br.s), 7.71 (1H, d, J=6.0 Hz), 7.87-7.88 (1H, m), 8.17 (1H, d, J=8.6 Hz), 8.54 (1H, dd, J=0.6, 4.9 Hz), 9.43 (1H, t, J=6.6 Hz)

Example 4

4-({4-[(4-Methylpyrazol-1-yl)methyl] phenyl}methyl)-N-{7H-pyrrolo[2,3-b]pyridine-3-ylmethyl}pyridine-2-carboxamide

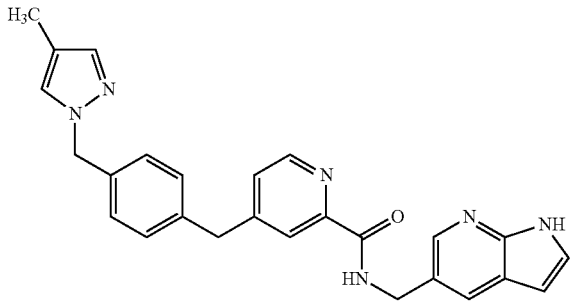 [SMILES: Cc1cnn(Cc2ccc(Cc3ccnc(C(=O)NCc4cnc5[nH]ccc5c4)c3)cc2)c1]

To a vial was added: 4-(4-((4-methyl-1H-pyrazol-1-yl) methyl)benzyl)picolinic acid, HCl (100 mg, 0.145 mmol), (1H-pyrrolo[2,3-b]pyridin-5-yl)methanamine hydrochloride (28.0 mg, 0.153 mmol), HATU (60.8 mg, 0.160 mmol) and dry DCM (2.5 mL). Next, DIPEA (254 µl, 1.454 mmol) was added and the reaction mixture was stirred at room temperature overnight. LC-MS showed conversion to desired compound, so the reaction mixture was partitioned between DCM (10 mL) and sat. NH4Cl (10 mL). The aqueous layer was extracted with DCM (3×10 mL). The combined organic layers were washed with water (20 mL), brine (10 mL) then dried (Na2SO4), filtered and concentrated in vacuo to an oil. The crude was purified by column chromatography (4 g RediSep, Dry loaded, 0-10% MeOH (1% NH3) in DCM). The product was dried overnight under vacuum (40° C.) to afford a glassy solid identified as 4-[4-(4-methyl-pyrazol-1-ylmethyl)-benzyl]-pyridine-2-carboxylic acid (1H-pyrrolo [2,3-b]pyridin-5-ylmethyl)-amide (11 mg, 0.020 mmol, 13.86% yield).

[M+H]+=437.20

NMR (d6-DMSO) δ: 1.98 (3H, s), 4.03 (2H, s), 4.54 (2H, d, J=6.4 Hz), 5.19 (2H, s), 6.39 (1H, dd, J=1.9, 3.4 Hz), 7.12-7.14 (2H, m), 7.21-7.23 (3H, m), 7.41-7.44 (2H, m), 7.51-7.52 (1H, m), 7.86-7.88 (2H, m), 8.20 (1H, d, J=2.0 Hz), 8.50 (1H, dd, J=0.6, 4.9 Hz), 9.30 (1H, t, J=6.4 Hz), 11.54 (1H, br.s)

Example 5

N-[(1-Aminoisoquinolin-6-yl)methyl]-6-oxo-1-({4-[(2-oxopyridin-1-yl)methyl]phenyl}methyl)pyridine-3-carboxamide

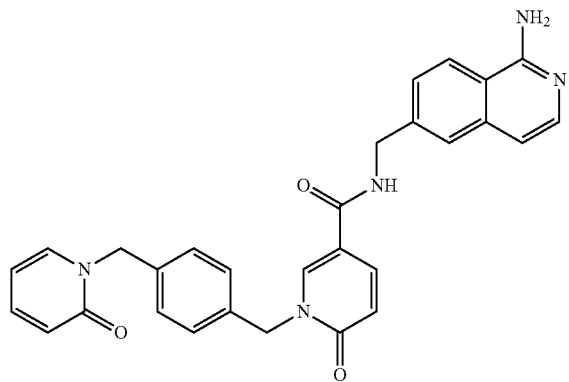 [SMILES: Nc1nccc2cc(CNC(=O)c3ccc(=O)n(Cc4ccc(Cn5ccccc5=O)cc4)c3)ccc12]

A. 6-Oxo-1-[4-(2-oxo-2H-pyridin-1-ylmethyl)-benzyl]-1,6-dihydro-pyridine-3-carboxylic Acid methyl ester To a round bottom flask under an atmosphere of nitrogen was added: methyl 1-(4-(chloromethyl)benzyl)-6-oxo-1,6-dihydropyridine-3-carboxylate (0.45 g, 1.234 mmol), pyridin-2-ol (0.129 g, 1.357 mmol), potassium carbonate (0.341 g, 2.468 mmol) and dry MeCN (8 mL) to give a golden orange coloured reaction mixture. The reaction was heated to 88° C. (base plate temp.) overnight. Upon completion, the reaction mixture was partitioned between EtOAc (50 mL) and water (30 mL). The aqueous layer was extracted with EtOAc (2×20 mL). The combined organic layers were washed with water (20 mL), brine (20 mL), dried (Na2SO4), filtered and concentrated in vacuo. The crude product was purified by chromatography on RediSep (12 g column, 0-10% EtOH in EtOAc), to afford a powdery white solid identified as 6-oxo-1-[4-(2-oxo-2H-pyridin-1-ylmethyl)-benzyl]-1,6-dihydro-pyridine-3-carboxylic acid methyl ester (0.37 g, 1.035 mmol, 84% yield).

[M+H]+=351.2 (M+H)+

B. 6-Oxo-1-[4-(2-oxo-2H-pyridin-1-ylmethyl)-benzyl]-1,6-dihydro-pyridine-3-carboxylic Acid To a round bottom flask was added: methyl 6-oxo-1-(4-((2-oxopyridin-1(2H)-yl)methyl)benzyl)-1,6-dihydropyridine-3-carboxylate (0.37 g, 1.035 mmol), THF (1.0 mL), MeOH (1.0 mL) and lithium hydroxide (0.124 g, 5.17 mmol) as a solution in water (2.0 mL). The reaction was heated to 65° C. for 16 hrs after which time LC-MS showed complete conversion to desired compound. The volatiles were removed in vacuo and the residue was partitioned between water (20 mL) and EtOAc (20 mL). The aqueous layer was concentrated in vacuo to dryness. The residue was redissolved in water (3.0 mL) and acidified to pH 3-4 with 1 N HCl to precipitate the product. The suspension was stirred at room temperature for 30 minutes before the solid was collected by filtration, washing with water (2×3.0 mL) and dried by suction for 15 minutes then in a vacuum oven (40° C.) over the weekend. The product was isolated as a white solid identified as 6-oxo-1-[4-(2-oxo-2H-pyridin-1-ylmethyl)-benzyl]-1,6-dihydro-pyridine-3-carboxylic acid (0.28 g, 0.816 mmol, 79% yield).

[M+H]+=337.1 (M+H)+

C. 6-Oxo-1-[4-(2-oxo-2H-pyridin-1-ylmethyl)-benzyl]-1,6-dihydro-pyridine-3-carboxylic Acid (1-amino-isoquinolin-6-ylmethyl)-amide To a vial was added: 6-oxo-1-(4-((2-oxopyridin-1(2H)-yl)methyl)benzyl)-1,6-dihydropyridine-3-carboxylic acid (50 mg, 0.149 mmol), 6-(aminomethyl)isoquinolin-1-amine dihydrochloride (40.2 mg, 0.164 mmol), 2-(3H-[1,2,3]triazolo[4,5-b]pyridin-3-yl)-1,1,3,3-tetramethylisouronium hexafluorophosphate(V) (65.0 mg, 0.171 mmol) and dry DCM (2.5 mL) to give a white suspension. Next, N-ethyl-N-isopropylpropan-2-amine (104 µl, 0.595 mmol) was added and the resulting suspension was stirred at room temperature for 2 hrs. LC-MS showed conversion to product. The reaction mixture was partitioned between DCM (30 mL) and sat. aq. NH4Cl (20 mL). Extracted with DCM/IPA (20:1, 2×20 mL). The combined organic layers were washed with water (20 mL) and brine (20 mL) then dried (Na2SO4), filtered and concentrated in vacuo. The crude was purified by column chromatography (12 g RediSep, dry loaded, 0-10% MeOH (1% NH3) in DCM). The product was dried under vacuum (40° C.) for 6 hrs to afford a pale yellow solid identified as 6-oxo-1-[4-(2-oxo-2H-pyridin-1-ylmethyl)-benzyl]-1,6-dihydro-pyridine-3-carboxylic acid (1-amino-isoquinolin-6-ylmethyl)-amide (32 mg, 0.062 mmol, 42.0% yield).

[M+H]=492.3

NMR (d6-DMSO) δ: 4.56 (2H, d, J=5.8 Hz), 5.06 (2H, s), 5.13 (2H, s), 6.21 (1H, dt, 1.3, 6.7 Hz), 6.38 (1H, br d, J=9.1 Hz), 6.46 (1H, d, J=9.5 Hz), 6.87-6.89 (3H, m), 7.24-7.29 (4H, m), 7.38-7.42 (2H, m), 7.55 (1 h, br s), 7.74-7.76 (2H, m), 7.93 (1H, dd, J=2.6, 9.5 Hz), 8.15 (1H, d, J=8.6 Hz), 8.48 (1H, d, J=2.5 Hz), 8.89 (1H, t, J=5.8 Hz)

Example 6

6-Oxo-1-({4-[(2-oxopyridin-1-yl)methyl]phenyl}methyl)-N-{7H-pyrrolo[2,3-b]pyridin-3-ylmethyl}pyridine-3-carboxamide

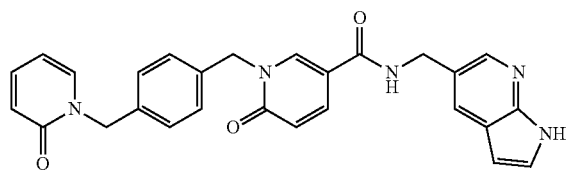 [SMILES: O=C(NCc1cnc2[nH]ccc2c1)c1ccc(=O)n(Cc2ccc(Cn3ccccc3=O)cc2)c1]

To a vial was added: 6-oxo-1-(4-((2-oxopyridin-1(2H)-yl)methyl)benzyl)-1,6-dihydropyridine-3-carboxylic acid (75 mg, 0.223 mmol), (1H-pyrrolo[2,3-b]pyridin-5-yl)methanamine (36.1 mg, 0.245 mmol), 2-(3H-[1,2,3]triazolo[4,5-b]pyridin-3-yl)-1,1,3,3-tetramethylisouronium hexafluorophosphate(V) (98 mg, 0.256 mmol) and dry DCM (3.0 mL) to give a white suspension. Next, N-ethyl-N-isopropylpropan-2-amine (97 µl, 0.557 mmol) was added to give a pale yellow opaque solution. The reaction was stirred at room temperature for 2 hrs. Further (1H-pyrrolo[2,3-b]pyridin-5-yl)methanamine (9.85 mg, 0.067 mmol) was added and stirring continued for 1 h and a tan coloured suspension formed. The reaction mixture was diluted with MeOH (5.0 mL) and isolated by SCX capture and release. The crude material was then purified by column chromatography RediSep (12 g silica, dry loaded, 0-10% MeOH (1% NH$_3$) in DCM). The product was dried in a vacuum oven (40° C.) over the weekend to afford a pale yellow solid identified as 6-oxo-1-[4-(2-oxo-2H-pyridin-1-ylmethyl)-benzyl]-1,6-dihydro-pyridine-3-carboxylic acid (1H-pyrrolo[2,3-b]pyridin-5-ylmethyl)-amide (80 mg, 0.167 mmol, 74.8% yield).

[M+H]$^+$=466.2

NMR (d6-DMSO) δ: 4.50 (2H, d, J=5.6 Hz), 5.05 (2H, s), 5.11 (2H, s), 6.21 (1H, dt, J=1.4, 6.7 Hz), 6.37-6.41 (2H, m), 6.43 (1H, d, 9.5 Hz), 7.23-7.27 (4H, m), 7.40 (1H, dq, J=2.1, 9.2 Hz), 7.44 (1H, t, J=2.8 Hz), 7.74 (1H, dd, J=1.6, 6.8 Hz), 7.87 (1H, d, J=1.6 Hz), 7.90 (1H, dd, J=2.6, 9.5 Hz), 8.19 (1H, d, J=2.0 Hz), 8.44 (1H, d, J=2.5 Hz), 8.76 (1H, t, J=5.6 Hz), 11.58 (1H, s).

Example 7

N-((1-Aminoisoquinolin-6-yl)methyl)-5-(hydroxy(4-((4-methyl-1H-pyrazol-1-yl)methyl)phenyl)methyl)nicotinamide

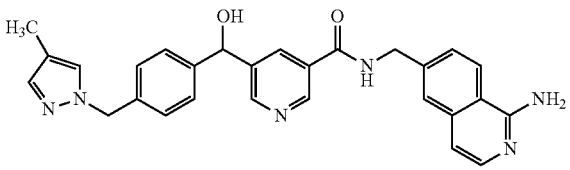 [SMILES: Cc1cnn(Cc2ccc(C(O)c3cncc(C(=O)NCc4ccc5c(N)nccc5c4)c3)cc2)c1]

A.
4-((4-Methyl-1H-pyrazol-1-yl)methyl)benzaldehyde

A solution of (4-((4-methyl-1H-pyrazol-1-yl)methyl)phenyl)methanol (2.54 g, 12.56 mmol) in DCM (85 mL) was treated with manganese(IV) oxide, activated (21.84 g, 251 mmol) and the mixture allowed to stir at ambient temperature overnight. The mixture was filtered through a pad of Celite, washing with DCM (200 mL), then concentrated under vacuum to afford 4-((4-methyl-1H-pyrazol-1-yl)methyl)benzaldehyde (2.04 g, 9.68 mmol, 77% yield) as a clear oil.

[M+H]$^+$=201.2 (M+H)$^+$

B. (5-Bromopyridin-3-yl)(4-((4-methyl-1H-pyrazol-1-yl)methyl)phenyl)methanol

Butyllithium, 2.5M in hexanes (4.08 ml, 10.19 mmol) was added dropwise to a cooled solution (−78° C.) of 3,5-dibromopyridine (2.390 g, 10.09 mmol) in dry ether (50 mL), keeping the temperature below −70° C. The mixture was stirred for 15 minutes and a solution of 4-((4-methyl-1H-pyrazol-1-yl)methyl)benzaldehyde (2.04 g, 10.19 mmol) in dry ether (5 mL) added dropwise, keeping the temperature below −70° C. The mixture was stirred for 15 minutes, and then allowed to warm to ambient temperature over 1 hour. The mixture was allowed to stir at ambient temperature overnight. The mixture was cooled in an ice-bath and quenched by the addition of saturated aqueous NH$_4$Cl solution (50 mL). The layers were separated and the aqueous phase extracted with EtOAc (3×50 mL). The combined organics were dried (MgSO$_4$), filtered and concentrated. The crude material was purified by flash chromatography loading in DCM, eluting with a gradient of 0 to 100% EtOAc/Iso-Hexanes to afford (5-bromopyridin-3-yl)(4-((4-methyl-1H-pyrazol-1-yl)methyl)phenyl)methanol (1.30 g, 3.27 mmol, 32.4% yield) as a sticky yellow gum on drying.

[M+H]$^+$=358.1/360.1 (M+H)$^+$

C. (5-Bromopyridin-3-yl)(4-((4-methyl-1H-pyrazol-1-yl)methyl)phenyl)methanone

A solution of (5-bromopyridin-3-yl)(4-((4-methyl-1H-pyrazol-1-yl)methyl)phenyl)methanol (1.08 g, 2.261 mmol) in chloroform (35 mL) was treated with manganese(IV) oxide, activated (3.93 g, 45.2 mmol) and the mixture allowed to stir at ambient temperature overnight. The mixture was filtered through Celite and concentrated under vacuum. The crude residue was purified by flash chromatography loading in DCM, eluting with a gradient of 0 to 70% EtOAc/Iso-Hexanes to afford the title compound.
[M+H]+=356.1/358.1 (M+H)+

D. 5-(4-((4-Methyl-1H-pyrazol-1-yl)methyl)benzoyl)nicotinonitrile

A stirred solution of (5-bromopyridin-3-yl)(4-((4-methyl-1H-pyrazol-1-yl)methyl)phenyl)methanone (0.500 g, 1.404 mmol) in anhydrous DMA (9 mL) was treated with dicyanozinc (0.379 g, 3.23 mmol) and de-gassed by bubbling through with $N_2$. $Pd(PPh_3)_4$ (0.081 g, 0.070 mmol) was charged and the mixture further de-gassed with $N_2$, then heated to 110° C. (Drysyn bath temperature) for 5 hrs then at ambient temperature overnight. The mixture was degassed with $N_2$ for 10 minutes, then further $Pd(PPh_3)_4$ (0.081 g, 0.070 mmol) added and the reaction heated at 110° C. for 2 hrs. The mixture was cooled and treated with further dicyanozinc (0.379 g, 3.23 mmol) and $Pd(PPh_3)_4$ (0.081 g, 0.070 mmol), then stirred and heated at 110° C. for 3 hrs and to 120° C. for 2 hrs, then at ambient temperature over a weekend. The mixture was diluted with DCM (50 mL) and filtered through Celite, washing with DCM (100 mL). Solvents were removed under vacuum and the residue purified by flash chromatography loading in DCM, eluting with a gradient of 0 to 50% EtOAc/DCM to afford the title compound (353 mg).
[M+H]+=303.2 (M+H)+

E. 5-(4((4-1H-Methyl-1H-pyrazol-1-yl)methyl)benzoyl)nicotinic Acid

A solution of 5-(4-((4-methyl-1H-pyrazol-1-yl)methyl) benzoyl)nicotinonitrile (248 mg, 0.574 mmol) in THF (3 mL) and water (1 mL) was treated with lithium hydroxide (68.8 mg, 2.87 mmol) and the mixture heated to 80° C. for 21 hrs. Organic solvents were removed under vacuum and the residue partitioned between EtOAc (15 mL) and water (10 mL, at pH 10). The aqueous was extracted with further EtOAc (10 mL) and the aqueous layer adjusted to pH 3 with 1M HCl. The aqueous was re-extracted with EtOAc (3×15 mL) and the combined organics dried (MgSO4), filtered and concentrated to afford 5-(4-((4-methyl-1H-pyrazol-1-yl) methyl)benzoyl)nicotinic acid (138 mg, 0.408 mmol, 71.1% yield) as a yellow foam.
[M+H]+=322.1 (M+H)+

F. N-((1-Aminoisoquinolin-6-yl)methyl)-5-(4-((4-methyl-1H-pyrazol-1-yl)methyl)benzoyl)nicotinamide A scintillation vial was charged with 5-(4-((4-methyl-1H-pyrazol-1-yl)methyl)benzoyl)nicotinic acid (134 mg, 0.417 mmol), 6-(aminomethyl)isoquinolin-1-amine dihydrochloride (113 mg, 0.459 mmol), 2-(3H-[1,2,3]triazolo[4,5-b] pyridin-3-yl)-1,1,3,3-tetramethylisouronium hexafluorophosphate(V) (174 mg, 0.459 mmol), dry DCM (3 mL) and DMF (0.3 ml). Next, N,N-diisopropylethylamine (291 µl, 1.668 mmol) was added and the mixture allowed to stir at ambient temperature overnight. The reaction mixture was concentrated under vacuum and purified by SCX (~3.5 g), washing with MeOH, eluting with 1% NH3/MeOH. The crude residue was purified by flash chromatography, loading in DCM (trace MeOH), eluting with a gradient of 0 to 7% MeOH/DCM (containing 0.3% NH3). Product containing fractions were combined and re-purified by flash chromatography loading in DCM, eluting with a gradient of 0 to 30% EtOH/EtOAc. The cleanest fractions were combined to afford N-((1-aminoisoquinolin-6-yl)methyl)-5-(4-((4-methyl-1H-pyrazol-1-yl)methyl)benzoyl)nicotinamide (34 mg, 0.070 mmol, 16.77% yield) as a pale yellow powder.
[M+H]+=477.3 (M+H)+

G. N-((1-Aminoisoquinolin-6-yl)methyl)-5-(hydroxy(4-((4-methyl-1H-pyrazol-1-yl)methyl)phenyl) methyl)nicotinamide A solution of N-((1-aminoisoquinolin-6-yl)methyl)-5-(4-((4-methyl-1H-pyrazol-1-yl)methyl)benzoyl)nicotinamide (50 mg, 0.105 mmol) in anhydrous MeOH (1.5 mL) was treated with sodium borohydride (11.91 mg, 0.315 mmol) and the mixture allowed to stir at ambient temperature for 2.5 hrs. LCMS indicated clean conversion to the desired compound. Solvents were removed under vacuum and the residue partitioned between EtOAc (30 mL) and water (20 mL). The aqueous layer was extracted with EtOAc (30 mL) and the combined organics washed with brine (20 mL), dried (MgSO4), filtered and concentrated. The crude product was purified by flash chromatography loading in DCM (trace MeOH), eluting with a gradient of 0 to 10% MeOH/DCM (containing 0.3% NH3) to afford N-((1-aminoisoquinolin-6-yl)methyl)-5-(hydroxy(4-((4-methyl-1H-pyrazol-1-yl) methyl)phenyl)methyl)nicotinamide (34 mg, 0.070 mmol, 67.0% yield) as a clear glass.
[M+H]+=479.3
NMR (d6-DMSO) δ: 1.97 (3H, s), 4.61 (2H, d, J=5.8 Hz), 5.19 (2H, s), 5.83 (1H, d, J=3.9 Hz), 6.19 (1H, d, J=3.9 Hz), 6.72 (2H, s), 6.86 (1H, d, J=5.8 Hz), 7.13-7.19 (2H, m), 7.21 (1H, s), 7.33-7.44 (3H, m), 7.51 (1H, s), 7.56 (1H, s), 7.76 (1H, d, J=5.8 Hz), 8.14 (1H, d, J=8.6 Hz), 8.20 (1H, t, J=2.1 Hz), 8.70 (1H, d, J=2.1 Hz), 8.93 (1H, d, J=2.1 Hz), 9.32 (1H, t, J=5.9 Hz).

Example 44

N-[(1-Aminoisoquinolin-6-yl)methyl]-5-({4-[(2-fluorophenyl)methyl]piperazin-1-yl}methyl)pyridine-3-carboxamide

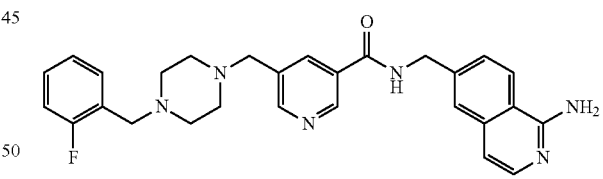

A. tert-Butyl 4-((5-(methoxycarbonyl)pyridin-3-yl) methyl)piperazine-1-carboxylate Methyl 5-bromonicotinate (2.95 g, 13.67 mmol), diacetoxypalladium (0.153 g, 0.683 mmol), potassium (4-boc-piperazin-1-yl)methyltrifluoroborate (5.022 g, 16.40 mmol), caesium carbonate (11.13 g, 34.2 mmol), and X-Phos (0.652 g, 1.367 mmol) dissolved in THF (40 mL) and water (10 mL) added. The resulting mixture was purged with $N_2$ for 10 minutes, stirred and heated at 70° C. o/n. The mixture was diluted with water (10 mL) and extracted with EtOAc (3×30 mL). The combined organics were dried (MgSO4), filtered and concentrated. The crude was purified by flash chromatography (EtOAc in i-Hex 0-100%, containing 1% Et3N) to afford tert-butyl 4-((5-(methoxycarbonyl)pyridin-3-yl)methyl)piperazine-1-carboxylate (4.81 g, 13.62 mmol, 100% yield) as a light brown solid.

[M+H]⁺=336.1

B. Methyl 5-(piperazin-1-ylmethyl)nicotinate

To a stirred solution of tert-butyl 4-((5-(methoxycarbonyl)pyridin-3-yl)methyl)piperazine-1-carboxylate (4.81 g, 14.34 mmol) in DCM (10 mL) at rt was added trifluoroacetic acid (10 mL, 130 mmol). The resulting solution was stirred at rt for 5 h. Reaction mixture was diluted with toluene (20 mL) and loaded on SCX (28 g), washing with MeOH and eluting with 1% NH₃ in MeOH. Solvent evaporated under reduced pressure to give methyl 5-(piperazin-1-ylmethyl)nicotinate (3.55 g, 14.34 mmol, 100% yield) as a pale yellow solid.

[M+H]⁺=236.0 (M+H)⁺

C. Methyl 5-((4-(2-fluorobenzyl)piperazin-1-yl)methyl)nicotinate

To a stirred solution of 2-fluorobenzaldehyde (79 mg, 0.638 mmol) and methyl 5-(piperazin-1-ylmethyl)nicotinate (150 mg, 0.638 mmol) in DCM (4 mL) was added a drop of acetic acid and left at RT for 1 hour. To this was added methyl 5-(piperazin-1-ylmethyl)nicotinate (150 mg, 0.638 mmol) and left at rt overnight. Reaction mixture was diluted with DCM (5 mL) and NaHCO₃(aq) (5 mL) added. Layers separated and aqueous extracted with DCM (2×5 mL); combined organics dried (Na₂SO₄), filtered and evaporated under reduced pressure to give methyl 5-((4-(2-fluorobenzyl)piperazin-1-yl)methyl)nicotinate (160 mg, 0.410 mmol, 64.3% yield) as a pale yellow thick oil.

[M+H]⁺=344.1

D. 5-((4-(2-Fluorobenzyl)piperazin-1-yl)methyl)nicotinic Acid

To a stirred solution of methyl 5-((4-(2-fluorobenzyl)piperazin-1-yl)methyl)nicotinate (147 mg, 0.428 mmol) in THF (2 mL) and water (1 mL) at rt was added lithium hydroxide (51.3 mg, 2.140 mmol). The resulting solution was stirred at rt overnight. Reaction mixture was loaded on SCX (2 g), washing with MeOH and eluting with 1% NH3 in MeOH. Solvent evaporated under reduced pressure to give 5-((4-(2-fluorobenzyl)piperazin-1-yl)methyl)nicotinic acid (130 mg, 0.395 mmol, 92% yield) as a colourless sticky oil.

[M+H]+=330.0

E. N-[(1-Aminoisoquinolin-6-yl)methyl]-5-({4-[(2-fluorophenyl)methyl]piperazin-1-yl}methyl)pyridine-3-carboxamide To a stirred solution of 5-((4-(2-fluorobenzyl)piperazin-1-yl)methyl)nicotinic acid (118 mg, 0.358 mmol), 6-(aminomethyl)isoquinolin-1-amine dihydrochloride (97 mg, 0.394 mmol), HATU (163 mg, 0.430 mmol) in DCM (2 mL) was added diisopropylethylamine (250 µl, 1.433 mmol). The resulting mixture was stirred at rt overnight. Reaction mixture was diluted with EtOAc (20 mL) and washed with 1M NaOH(aq) (2×10 mL). Organics dried (Na2SO4), filtered and evaporated under reduced pressure to give crude compound which was purified by flash chromatography (EtOH in EtOAc 0-50%), twice to afford N-((1-aminoisoquinolin-6-yl)methyl)-5-((4-(2-fluorobenzyl)piperazin-1-yl)methyl)nicotinamide (39.3 mg, 0.079 mmol, 22.07% yield) as a pale yellow solid.

m/z 485.1 (M+H)⁺

NMR (d6-DMSO) δ: 2.20-2.47 (8H, m), 3.51 (2H, s), 3.55 (2H, s), 4.63 (2H, d, J=5.8 Hz), 6.72 (2H, s), 6.87 (1H, d, J=5.6 Hz), 7.10-7.19 (2H, m), 7.26-7.34 (1H, m), 7.35-7.45 (2H, m), 7.58 (1H, s), 7.76 (1H, d, J=5.8 Hz), 8.12-8.17 (2H, m), 8.61 (1H, d, J=2.0 Hz), 8.97 (1H, d, J=2.1 Hz), 9.32 (1H, t, J=5.9 Hz).

Example 77

N-[(1-Aminoisoquinolin-6-yl)methyl]-5-{[2-(pyrrolidin-1-yl)pyridin-4-yl]methyl}pyridine-3-carboxamide

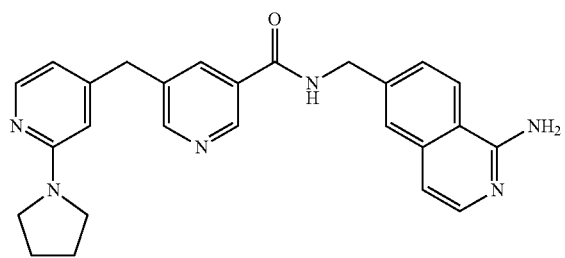 [SMILES: Nc1nccc2cc(CNC(=O)c3cncc(Cc4ccnc(N5CCCC5)c4)c3)ccc12]

A. 4-(Chloromethyl)-2-fluoropyridine

A 500 ml flask was charged with 2-fluoro-4-methylpyridine (25 g, 225 mmol), N-chlorosuccinimide (45.1 g, 337 mmol), benzoyl peroxide, Luperox (1.453 g, 4.50 mmol), acetic acid (1 mL, 17.47 mmol) and acetonitrile (132 mL, 2527 mmol). The reaction mixture was heated to gentle reflux giving a pale yellow solution which was left to reflux for 5 hours then at ambient temperature overnight. The mixture was partitioned between water (20 mL) and EtOAc (30 mL). Brine (30 mL) was added to form two layers. These were separated and the aqueous re-extracted with further EtOAc (2×30 mL). The combined organics were washed with brine (30 mL), dried (MgSO₄), filtered and concentrated. On cooling a precipitate was filtered, washing with DCM (40 mL) then concentrated under vacuum again. The residue was re-purified by flash chromatography loading in a minimum quantity of DCM, eluting with a gradient of 0 to 15% EtOAc/Iso-Hexanes (holding at 6% to elute product) to afford 4-(chloromethyl)-2-fluoropyridine (11.8 g, 78 mmol, 34.6% yield) as a clear oil.

B. Methyl 5-((2-fluoropyridin-4-yl)methyl)nicotinate

A solution of 4-(chloromethyl)-2-fluoropyridine (2.012 g, 13.82 mmol) and methyl 5-(4,4,5,5-tetramethyl-1,3,2-dioxaborolan-2-yl)nicotinate (4.00 g, 15.20 mmol) in THF (40 mL) and water (1 mL) was treated with potassium carbonate (3.82 g, 27.6 mmol) and the mixture degassed with N₂ for 5 minutes. Pd(Ph₃)₄ catalyst (1.597 g, 1.382 mmol) was added and the mixture briefly degassed again before heating to 90° C. (Drysyn bath temperature) for 2 hours. The reaction was partitioned between EtOAc (150 mL) and water (75 mL). The aqueous layer was extracted with further EtOAc (2×70 mL) and the combined organics washed with brine (75 mL), dried (MgSO₄), filtered and concentrated. The crude material was purified by flash chromatography loading in DCM, eluting with a gradient of 10 to 70% EtOAc/Iso-Hexanes (holding at 55% to elute product) to afford methyl 5-((2-fluoropyridin-4-yl)methyl)nicotinate (1.99 g, 8.00 mmol, 57.9% yield) as a yellow gum m/z=247.1 (M+H)⁺

C. Ammonium 5-((2-fluoropyridin-4-yl)methyl)nicotinate

A solution of methyl 5-((2-fluoropyridin-4-yl)methyl)nicotinate (2.45 g, 9.95 mmol) in MeOH (25 mL) and THF (60 mL) was treated with water (20 mL) and lithium hydroxide (0.286 g, 11.94 mmol), then stirred at ambient temperature overnight. Further lithium hydroxide (0.286 g, 11.94 mmol) was added and the mixture stirred at ambient temperature overnight. The majority of the organic solvents were removed under vacuum and water (25 mL) added. The pH was adjusted to ~5 and the mixture purified directly by SCX (45 g), washing with MeOH, eluting with 1% NH₃/MeOH. The isolated product was triturated with DCM (30 mL) and filtered to afford ammonium 5-((2-fluoropyridin-4-yl)methyl)nicotinate (1.85 g, 7.35 mmol, 73.9% yield) as a white powder.

m/z=233.1 (M+H)⁺

D. N-((1-Aminoisoquinolin-6-yl)methyl)-5-((2-fluoropyridin-4-yl)methyl)nicotinamide A mixture of ammonium 5-((2-fluoropyridin-4-yl)methyl)nicotinate (1.40 g, 5.62 mmol), 6-(aminomethyl)isoquinolin-1-amine dihydrochloride (1.521 g, 6.18 mmol) and 2-(3H-[1,2,3]triazolo[4,5-b]pyridin-3-yl)-1,1,3,3-tetramethylisouronium hexafluorophosphate(V) (2.349 g, 6.18 mmol) in a mixture of anhydrous DCM (20 mL) and anhydrous DMF (2 mL) was treated with N,N-diisopropylethylamine (5.28 ml, 30.3 mmol) and the resultant suspension sonicated briefly before stirring at ambient temperature overnight. The solvents were removed under vacuum. The residue was partitioned between EtOAc (50 mL, trace MeOH for solubility) and saturated aqueous NH₄Cl (50 mL). The aqueous layer was extracted with further EtOAc (6×50 mL) and the combined organics dried (MgSO₄), filtered and concentrated. The crude material was purified by flash chromatography loading in DCM (trace MeOH), eluting with a gradient of 0 to 30% EtOH/EtOAc to afford N-((1-aminoisoquinolin-6-yl)methyl)-5-((2-fluoropyridin-4-yl)methyl)nicotinamide as a pale yellow powder.

m/z=388.2 (M+H)⁺

E. N-[(1-Aminoisoquinolin-6-yl)methyl]-5-{[2-(pyrrolidin-1-yl)-pyridin-4-yl]methyl}pyridine-3-carboxamide A mixture of N-((1-aminoisoquinolin-6-yl)methyl)-5-((2-fluoropyridin-4-yl)methyl)nicotinamide (100 mg, 0.258 mmol) and pyrrolidine (424 µl, 5.16 mmol) in anhydrous dioxanes (200 µL) were heated together at 90° C. for 5 hours. Solvents were removed under vacuum and the residue purified by flash chromatography loading in DCM, eluting with a gradient of 0 to 7.5% MeOH/DCM (containing 0.3% NH₃). The compound was dissolved in a minimum quantity of DCM and Et₂O added to precipitate. This mixture was sonicated and stirred for ~30 minutes, then filtered to afford N-((1-aminoisoquinolin-6-yl)methyl)-5-((2-(pyrrolidin-1-yl)pyridin-4-yl)methyl)nicotinamide (73 mg, 0.165 mmol, 63.8% yield) as a white powder.

(M+H)⁺=439.1

NMR (d6-DMSO) δ: 1.90 (4H, m), 3.33 (4H, m), 3.93 (2H, s), 4.61 (2H, d, J=5.9 Hz), 6.37 (1H, s), 6.41 (1H, dd, J=5.1, 1.4 Hz), 6.74 (2H, s), 6.86 (1H, d, J=5.9 Hz), 7.40 (1H, dd, J=8.6, 1.7 Hz), 7.56 (1H, s), 7.76 (1H, d, J=5.8 Hz), 7.94 (1H, d, J=5.1 Hz), 8.10 (1H, t, J=2.2 Hz), 8.13 (1H, d, J=8.6 Hz), 8.67 (1H, d, J=2.1 Hz), 8.94 (1H, d, J=2.1 Hz), 9.32 (1H, t, J=5.9 Hz).

The compounds in the following tables were synthesised as described for Examples 1-7 and 44 and 77.

TABLE 1

| Example Number | G | Free Base MW | [M + H]⁺ |
|---|---|---|---|
| 8 | (4-methylpyrazol-1-ylmethyl-phenyl-methyl-pyrimidinyl) | 463.5 | 464.3 |
| 9 | (4-methylpyrazol-1-ylmethyl-phenyl-methyl-pyrazinyl) | 463.5 | 464.3 |

TABLE 1-continued
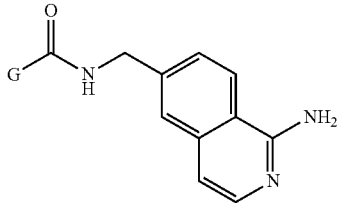
| Example Number | G | Free Base MW | [M + H]+ |
|---|---|---|---|
| 10 | 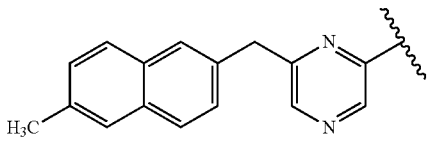 [SMILES: *c1cncc(Cc2ccc3cc(C)ccc3c2)n1] | 434.5 | 435.1 |
| 11 | 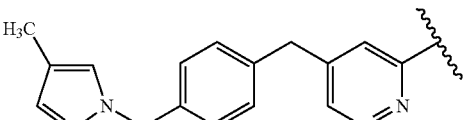 | 463.5 | 464.3 |
TABLE 2
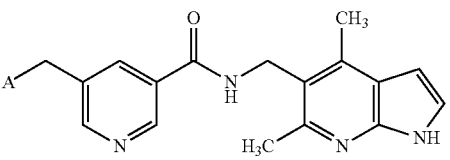
| Example Number | A | Free Base MW | [M + H]+ |
|---|---|---|---|
| 12 | 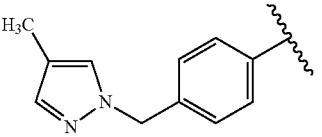 [SMILES: *c1ccc(Cn2cc(C)cn2)cc1] | 464.6 | 465.3 |
| 13 | 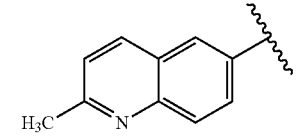 | 435.5 | 436 |
TABLE 3
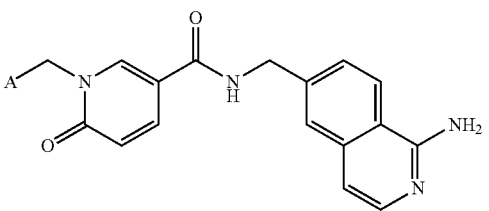
| Example Number | A | Free Base MW | [M + H]+ |
|---|---|---|---|
| 14 | 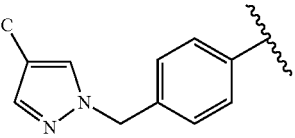 | 467.5 | 468.2 |
| 15 | 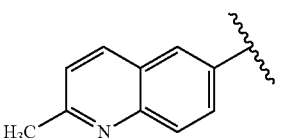 | 478.6 | 479.3 |
| 16 | 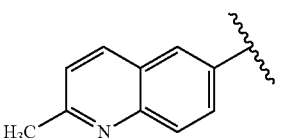 | 449.5 | 449.6 |

TABLE 4
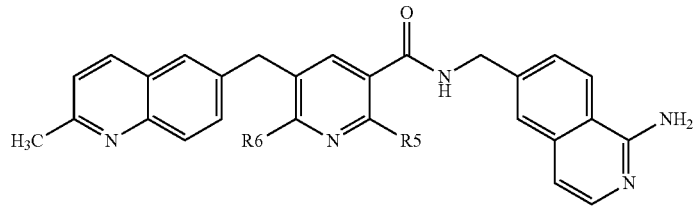
| Example Number | R6 | R5 | Free Base MW | [M + H]+ |
| --- | --- | --- | --- | --- |
| 17 | H | H | 433.5 | 434.2 |
| 18 | OCH3 | H | 463.5 | 463.7 |
| 19 | H | OCH3 | 463.5 | 464.2 |
| 20 | H | OH | 449.5 | 450.3 |
| 21 | NHCH3 | H | 462.55 | 463.1 |
| 22 | H | CH3 | 447.5 | 448.1 |
TABLE 5
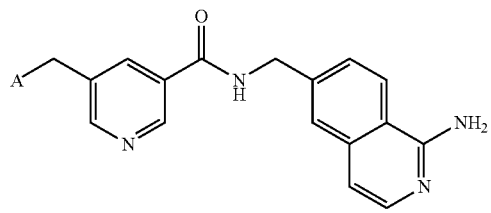
| Example Number | A | Free Base MW | [M + H]+ |
| --- | --- | --- | --- |
| 23 | phenyl | 368.4 | 369.2 |
| 24 | 2-phenylthiazol-4-yl | 451.5 | 452.2 |
| 25 | 3-methoxyphenyl | 398.5 | 398.8 |
| 26 | 4-methoxyphenyl | 398.5 | 398.7 |

TABLE 5-continued

| Example Number | A | Free Base MW | [M + H]+ |
|---|---|---|---|
| 27 | 4-(1H-pyrazol-1-yl)phenyl | 434.5 | 434.8 |
| 28 | isoquinolin-7-yl | 419.5 | 419.6 |
| 29 | 2-methoxyphenyl | 398.5 | 398.8 |
| 30 | 3-(1H-pyrazol-1-yl)phenyl | 434.5 | 435.3 |
| 31 | quinolin-6-yl | 419.5 | 420.2 |
| 32 | 3-((1H-pyrazol-1-yl)methyl)phenyl | 448.5 | 449.1 |

TABLE 5-continued
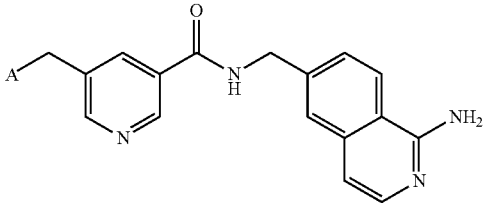
| Example Number | A | Free Base MW | [M + H]⁺ |
|---|---|---|---|
| 33 | 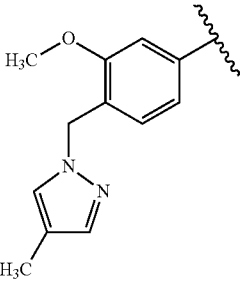 [SMILES: *c1ccc(Cn2cc(C)cn2)c(OC)c1] | 492.6 | 493.1 |
| 34 | 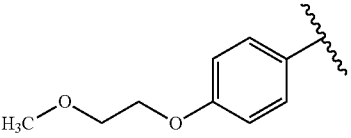 [SMILES: *c1ccc(OCCOC)cc1] | 442.5 | 443.1 |
| 35 | 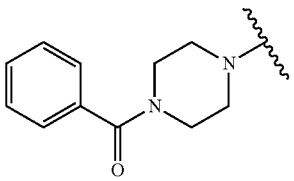 [SMILES: *N1CCN(C(=O)c2ccccc2)CC1] | 516.6 | 517.2 |
| 36 | 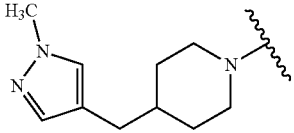 [SMILES: *N1CCC(Cc2cnn(C)c2)CC1] | 480.6 | 481.3 |
| 37 | 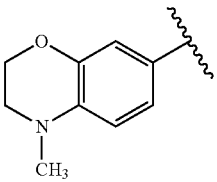 [SMILES: *c1ccc2c(c1)OCCN2C] | 469.6 | 470.3 |
| 38 |  | 439.51 | 440 |

TABLE 5-continued
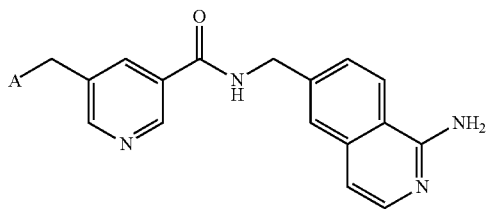
| Example Number | A | Free Base MW | [M + H]+ |
|---|---|---|---|
| 39 | 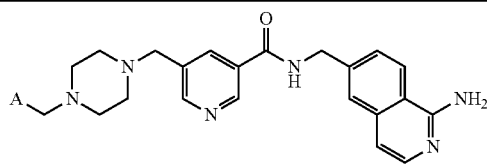 | 452.6 | 453.1 |
| 40 |  | 416.5 | 417.1 |
TABLE 6
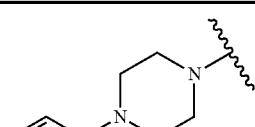
| Example Number | A | Free Base MW | [M + H]+ |
|---|---|---|---|
| 41 | 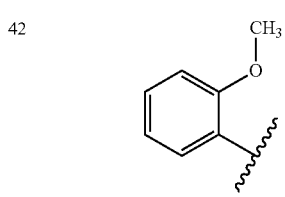 | 466.6 | 467.3 |
| 42 | 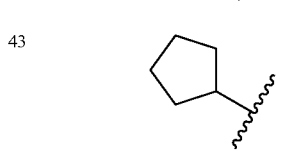 | 496.6 | 497.2 |
| 43 | 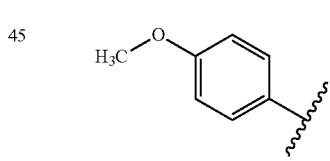 | 458.6 | 459.1 |
| 45 | H₃C-O-⌬-⌇ | 496.6 | 497.1 |
TABLE 6-continued
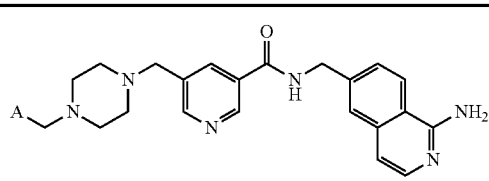
| Example Number | A | Free Base MW | [M + H]+ |
|---|---|---|---|
| 46 | 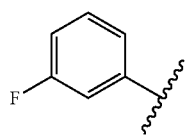 | 484.6 | 485.1 |
| 47 | 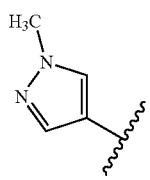 | 470.6 | 469.2 |
| 48 | 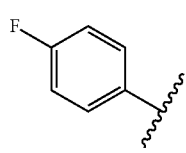 [SMILES: *c1ccc(F)cc1] | 484.6 | 485.3 |

TABLE 6-continued

[Structure: A-N(piperazine)-CH2-pyridine-C(O)NH-CH2-(1-aminoisoquinoline)]

| Example Number | A | Free Base MW | [M + H]⁺ |
|---|---|---|---|
| 49 | 3-methoxyphenyl | 496.6 | 495.1 |
| 50 | phenylethyl | 494.6 | 495.3 |
| 51 | benzyl | 480.6 | 481.1 |
| 52 | HOOC-CH< | 434.5 | 435.1 |

TABLE 7

[Structure: A-pyridine-CH2-pyridine-C(O)NH-CH2-(1-aminoisoquinoline)]

| Example Number | A | Free Base MW | [M + H]⁺ |
|---|---|---|---|
| 53 | 2-oxopyrrolidin-1-yl | 452.5 | 452.6 |
| 54 | F | 387.4 | 388.2 |
| 55 | pyrrolidin-1-yl | 438.5 | 438.8 |
| 56 | piperidin-1-yl | 452.6 | 453.3 |
| 57 | 3,3-difluoropyrrolidin-1-yl | 474.5 | 475 |

TABLE 7-continued

| Example Number | A | Free Base MW | [M + H]+ |
|---|---|---|---|
| 58 | 2-methylpyrrolidin-1-yl | 452.6 | 453.1 |
| 59 | 3-hydroxypyrrolidin-1-yl | 454.5 | 455 |
| 60 | 3-fluoropyrrolidin-1-yl | 456.5 | 457.1 |
| 61 | 3-methylpyrrolidin-1-yl | 452.6 | 453.1 |
| 62 | 3-methoxypyrrolidin-1-yl | 468.6 | 469.1 |
| 63 | morpholin-4-yl | 454.5 | 455.1 |
| 64 | 4-methylpiperazin-1-yl | 467.6 | 468.1 |

TABLE 7-continued

| Example Number | A | Free Base MW | [M + H]⁺ |
|---|---|---|---|
| 65 | 2,2-dimethylpyrrolidin-1-yl | 466.6 | 467.1 |
| 66 | diethylamino | 440.5 | 441.1 |
| 67 | 2-(hydroxymethyl)pyrrolidin-1-yl | 468.6 | 469.1 |
| 68 | (3S)-3-(dimethylamino)pyrrolidin-1-yl | 481.6 | 482.2 |
| 69 | (3R)-3-(dimethylamino)pyrrolidin-1-yl | 481.6 | 482.2 |
| 70 | isopropoxy | 427.5 | 428.1 |
| 71 | 3-(hydroxymethyl)pyrrolidin-1-yl | 468.6 | 469.1 |
| 72 | 3-(ethoxycarbonyl)pyrrolidin-1-yl | 510.6 | 511.1 |
| 73 | isopropyl(methyl)amino | 440.5 | 441.2 |

TABLE 7-continued
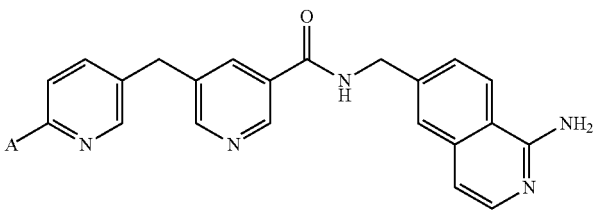
| Example Number | A | Free Base MW | [M + H]+ |
|---|---|---|---|
| 74 | 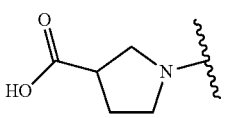 | 466.6 | 467.1 |
| 75 | 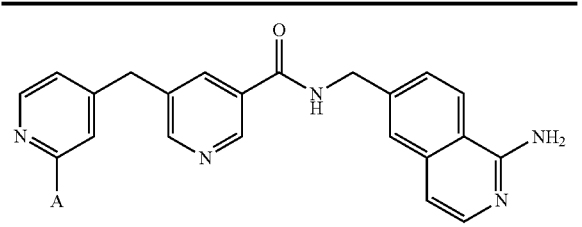 | 482.5 | 483.1 |
TABLE 8
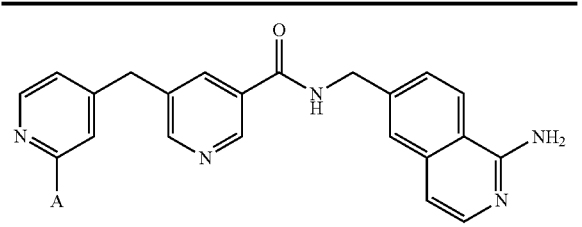
| Example Number | A | Free Base MW | [M + H]+ |
|---|---|---|---|
| 76 | 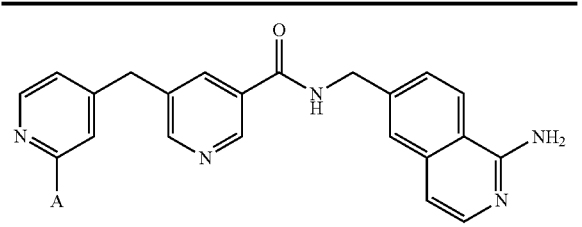 | 452.5 | 453.3 |
| 78 | 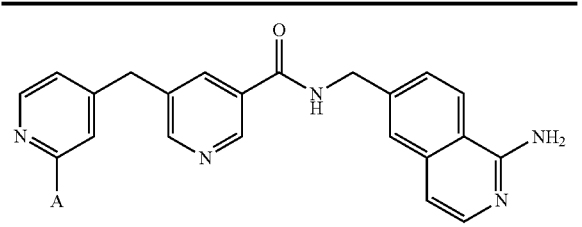 | 452.6 | 453.3 |
| 79 | 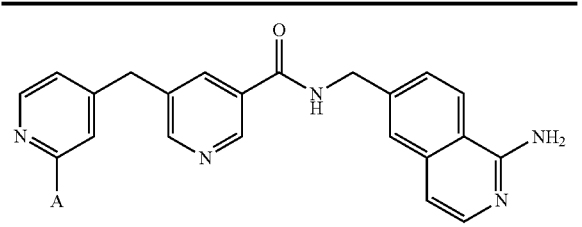 | 452.6 | 453.1 |
| 80 | 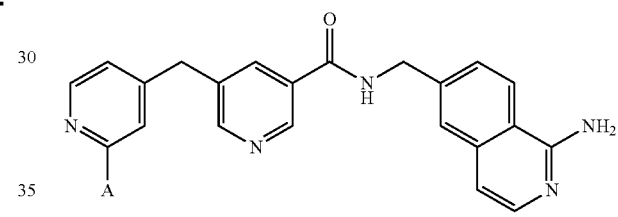 | 474.5 | 475.1 |
TABLE 8-continued
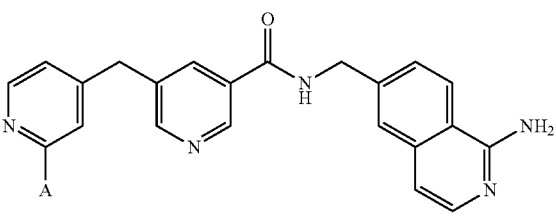
| Example Number | A | Free Base MW | [M + H]+ |
|---|---|---|---|
| 81 | 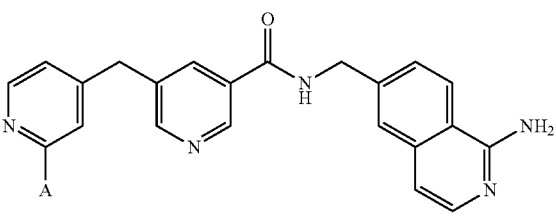 | 454.5 | 455.1 |
| 82 | 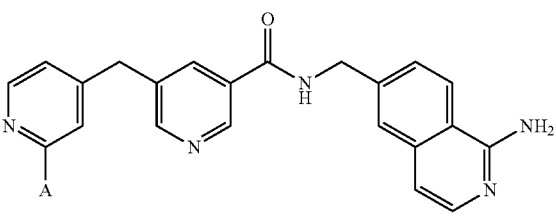 | 456.5 | 457.1 |
| 83 | 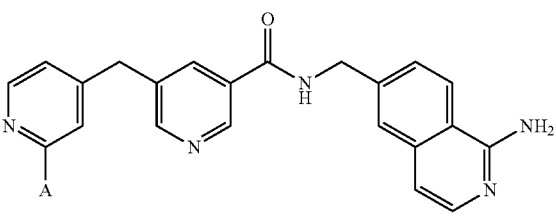 | 452.6 | 453.1 |
| 84 | 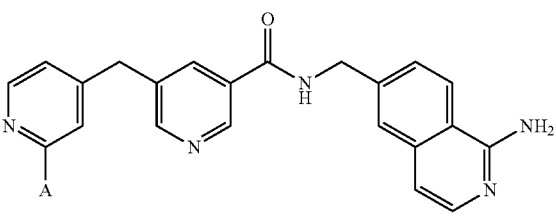 | 466.6 | 467.2 |

TABLE 8-continued
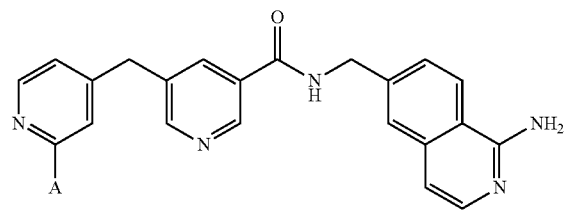
| Example Number | A | Free Base MW | [M + H]+ |
|---|---|---|---|
| 85 | 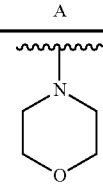 | 454.5 | 455.1 |
| 86 | 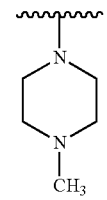 | 467.6 | 468.1 |
| 87 | 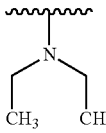 | 440.5 | 441.2 |
| 88 | 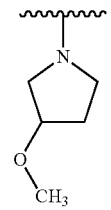 | 468.6 | 469.2 |
TABLE 8-continued
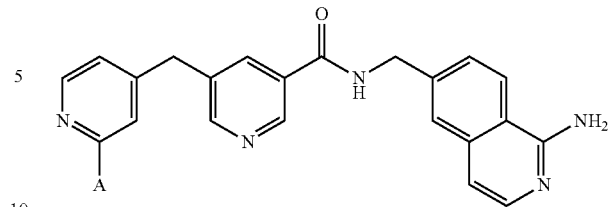
| Example Number | A | Free Base MW | [M + H]+ |
|---|---|---|---|
| 89 | 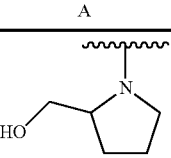 | 468.6 | 469.1 |
| 90 | 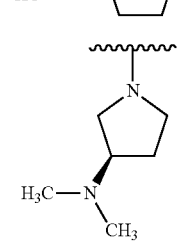 | 481.6 | 482.2 |
| 91 | 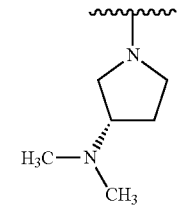 | 481.6 | 482.2 |
| 92 | 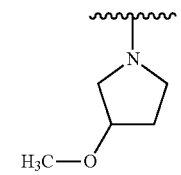 | 468.6 | 469.1 |
TABLE 9
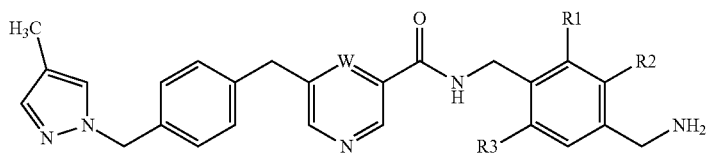
| Example Number | R1 | R2 | R3 | W | Free Base MW | [M + H]+ |
|---|---|---|---|---|---|---|
| 93 | H | H | CH₃ | CH | 439.6 | 440.0 |
| 94 | CH₃ | H | CH₃ | CH | 453.6 | 454.1 |
| 95 | CH₃ | H | CH₃ | N | 454.6 | 455.1 |
| 96 | H | F | H | CH | 443.5 | 444.1 |
TABLE 10
| Example No | Name |
|---|---|
| 8 | N-[(1-Aminoisoquinolin-6-yl)methyl]-6-({4-[(4-methylpyrazol-1-yl)methyl]phenyl}methyl)pyrimidine-4-carboxamide |

TABLE 10-continued

| Example No | Name |
|---|---|
| 9 | N-[(1-Aminoisoquinolin-6-yl)methyl]-6-({4-[(4-methylpyrazol-1-yl)methyl]phenyl}methyl)pyrazine-2-carboxamide |
| 10 | N-[(1-Aminoisoquinolin-6-yl)methyl]-6-[(2-methylquinolin-6-yl)methyl]pyrazine-2-carboxamide |
| 11 | N-[(1-Aminoisoquinolin-6-yl)methyl]-5-({4-[(4-methylpyrazol-1-yl)methyl]phenyl}methyl)pyridazine-3-carboxamide |
| 12 | N-({2,4-Dimethyl-7H-pyrrolo[2,3-b]pyridin-3-yl}methyl)-5-({4-[(4-methylpyrazol-1-yl)methyl]phenyl}methyl)pyridine-3-carboxamide |
| 13 | N-({2,4-Dimethyl-7H-pyrrolo[2,3-b]pyridin-3-yl}methyl)-5-[(2-methylquinolin-6-yl)methyl]pyridine-3-carboxamide |
| 14 | N-[(1-Aminoisoquinolin-6-yl)methyl]-6-oxo-1-[(2-phenyl-1,3-thiazol-4-yl)methyl]pyridine-3-carboxamide |
| 15 | N-[(1-Aminoisoquinolin-6-yl)methyl]-1-({4-[(4-methylpyrazol-1-yl)methyl]phenyl}methyl)-6-oxopyridine-3-carboxamide |
| 16 | N-[(1-Aminoisoquinolin-6-yl)methyl]-1-[(2-methylquinolin-6-yl)methyl]-6-oxopyridine-3-carboxamide |
| 17 | N-[(1-Aminoisoquinolin-6-yl)methyl]-5-[(2-methylquinolin-6-yl)methyl]pyridine-3-carboxamide |
| 18 | N-[(1-Aminoisoquinolin-6-yl)methyl]-6-methoxy-5-[(2-methylquinolin-6-yl)methyl]pyridine-3-carboxamide |
| 19 | N-[(1-Aminoisoquinolin-6-yl)methyl]-2-methoxy-5-[(2-methylquinolin-6-yl)methyl]pyridine-3-carboxamide |
| 20 | N-[(1-Aminoisoquinolin-6-yl)methyl]-5-[(2-methylquinolin-6-yl)methyl]-2-oxo-1H-pyridine-3-carboxamide |
| 21 | N-[(1-Aminoisoquinolin-6-yl)methyl]-6-(methylamino)-5-[(2-methylquinolin-6-yl)methyl]pyridine-3-carboxamide |
| 22 | N-[(1-Aminoisoquinolin-6-yl)methyl]-2-methyl-5-[(2-methylquinolin-6-yl)methyl]pyridine-3-carboxamide |
| 23 | N-[(1-Aminoisoquinolin-6-yl)methyl]-5-benzylpyridine-3-carboxamide |
| 24 | N-[(1-Aminoisoquinolin-6-yl)methyl]-5-[(2-phenyl-1,3-thiazol-4-yl)methyl]pyridine-3-carboxamide |
| 25 | N-[(1-Aminoisoquinolin-6-yl)methyl]-5-[(3-methoxyphenyl)methyl]pyridine-3-carboxamide |
| 26 | N-[(1-Aminoisoquinolin-6-yl)methyl]-5-[(4-methoxyphenyl)methyl]pyridine-3-carboxamide |
| 27 | N-[(1-Aminoisoquinolin-6-yl)methyl]-5-{[4-(pyrazol-1-yl)phenyl]methyl}pyridine-3-carboxamide |
| 28 | N-[(1-Aminoisoquinolin-6-yl)methyl]-5-(isoquinolin-7-ylmethyl)pyridine-3-carboxamide |
| 29 | N-[(1-Aminoisoquinolin-6-yl)methyl]-5-[(2-methoxyphenyl)methyl]pyridine-3-carboxamide |
| 30 | N-[(1-Aminoisoquinolin-6-yl)methyl]-5-{[3-(pyrazol-1-yl)phenyl]methyl}pyridine-3-carboxamide |
| 31 | N-[(1-Aminoisoquinolin-6-yl)methyl]-5-(quinolin-6-ylmethyl)pyridine-3-carboxamide |
| 32 | N-[(1-Aminoisoquinolin-6-yl)methyl]-5-{[3-(pyrazol-1-ylmethyl)phenyl]methyl}pyridine-3-carboxamide |
| 33 | N-[(1-Aminoisoquinolin-6-yl)methyl]-5-({3-methoxy-4-[(4-methylpyrazol-1-yl)methyl]phenyl}methyl)pyridine-3-carboxamide |
| 34 | N-[(1-Aminoisoquinolin-6-yl)methyl]-5-{[4-(2-methoxyethoxy)phenyl]methyl}pyridine-3-carboxamide |
| 35 | N-[(1-Aminoisoquinolin-6-yl)methyl]-5-{[4-(benzenesulfonyl)piperazin-1-yl]methyl}pyridine-3-carboxamide |
| 36 | N-[(1-Aminoisoquinolin-6-yl)methyl]-5-[(4-benzoylpiperazin-1-yl)methyl]pyridine-3-carboxamide |
| 37 | N-[(1-Aminoisoquinolin-6-yl)methyl]-5-({4-[(4-methylpyrazol-1-yl)methyl]piperidin-1-yl}methyl)pyridine-3-carboxamide |
| 38 | N-[(1-Aminoisoquinolin-6-yl)methyl]-5-[(4-methyl-2,3-dihydro-1,4-benzoxazin-7-yl)methyl]pyridine-3-carboxamide |
| 39 | N-[(1-Aminoisoquinolin-6-yl)methyl]-5-[(4-phenylpiperazin-1-yl)methyl]pyridine-3-carboxamide |
| 40 | N-[(1-Aminoisoquinolin-6-yl)methyl]-5-{[2-(4-methylpyrazol-1-yl)ethoxy]methyl}pyridine-3-carboxamide |
| 41 | N-[(1-Aminoisoquinolin-6-yl)methyl]-5-[(4-benzylpiperazin-1-yl)methyl]pyridine-3-carboxamide |
| 42 | N-[(1-Aminoisoquinolin-6-yl)methyl]-5-({4-[(2-methoxyphenyl)methyl]piperazin-1-yl}methyl)pyridine-3-carboxamide |
| 43 | N-[(1-Aminoisoquinolin-6-yl)methyl]-5-{[4-(cyclopentylmethyl)piperazin-1-yl]methyl}pyridine-3-carboxamide |
| 45 | N-[(1-Aminoisoquinolin-6-yl)methyl]-5-({4-[(4-methoxyphenyl)methyl]piperazin-1-yl}methyl)pyridine-3-carboxamide |
| 46 | N-[(1-Aminoisoquinolin-6-yl)methyl]-5-({4-[(3-fluorophenyl)methl]piperazin-1-yl}methyl)pyridine-3-carboxamide |
| 47 | N-[(1-Aminoisoquinolin-6-yl)methyl]-5-({4-[(1-methylpyrazol-4-yl)methyl]piperazin-1-yl}methyl)pyridine-3-carboxamide |
| 48 | N-[(1-Aminoisoquinolin-6-yl)methyl]-5-({4-[(4-fluorophenyl)methyl]piperazin-1-yl}methyl)pyridine-3-carboxamide |

TABLE 10-continued

| Example No | Name |
|---|---|
| 49 | N-[(1-Aminoisoquinolin-6-yl)methyl]-5-({4-[(3-methoxyphenyl)methyl]piperazin-1-yl}methyl)pyridine-3-carboxamide |
| 50 | N-[(1-Aminoisoquinolin-6-yl)methyl]-5-{[4-(3-phenylpropyl)piperazin-1-yl]methyl}pyridine-3-carboxamide |
| 51 | N-[(1-Aminoisoquinolin-6-yl)methyl]-5-{[4-(2-phenylethyl)piperazin-1-yl]methyl}pyridine-3-carboxamide |
| 52 | {4-[(5-{[(1-Aminoisoquinolin-6-yl)methyl]carbamoyl}pyridin-3-yl)methyl]piperazin-1-yl}acetic acid |
| 53 | N-[(1-Aminoisoquinolin-6-yl)methyl]-5-{[6-(2-oxopyrrolidin-1-yl)pyridin-3-yl]methyl}pyridine-3-carboxamide |
| 54 | N-[(1-Aminoisoquinolin-6-yl)methyl]-5-[(6-fluoropyridin-3-yl)methyl]pyridine-3-carboxamide |
| 55 | N-[(1-Aminoisoquinolin-6-yl)methyl]-5-{[6-(pyrrolidin-1-yl)pyridin-3-yl]methyl}pyridine-3-carboxamide |
| 56 | N-[(1-Aminoisoquinolin-6-yl)methyl]-5-{[6-(piperidin-1-yl)pyridin-3-yl]methyl}pyridine-3-carboxamide |
| 57 | N-[(1-Aminoisoquinolin-6-yl)methyl]-5-{[6-(3,3-difluoropyrrolidin-1-yl)pyridin-3-yl]methyl}pyridine-3-carboxamide |
| 58 | N-[(1-Aminoisoquinolin-6-yl)methyl]-5-{[6-(2-methylpyrrolidin-1-yl)pyridin-3-yl]methyl}pyridine-3-carboxamide |
| 59 | N-[(1-Aminoisoquinolin-6-yl)methyl]-5-{[6-(3-hydroxypyrrolidin-1-yl)pyridin-3-yl]methyl}pyridine-3-carboxamide |
| 60 | N-[(1-Aminoisoquinolin-6-yl)methyl]-5-{[6-(3-fluoropyrrolidin-1-yl)pyridin-3-yl]methyl}pyridine-3-carboxamide |
| 61 | N-[(1-Aminoisoquinolin-6-yl)methyl]-5-{[6-(3-methylpyrrolidin-1-yl)pyridin-3-yl]methyl}pyridine-3-carboxamide |
| 62 | N-[(1-Aminoisoquinolin-6-yl)methyl]-5-{[6-(3-methoxypyrrolidin-1-yl)pyridin-3-yl]methyl}pyridine-3-carboxamide |
| 63 | N-[(1-Aminoisoquinolin-6-yl)methyl]-5-{[6-(morpholin-4-yl)pyridin-3-yl]methyl}pyridine-3-carboxamide |
| 64 | N-[(1-Aminoisoquinolin-6-yl)methyl]-5-{[6-(4-methylpiperazin-1-yl)pyridin-3-yl]methyl}pyridine-3-carboxamide |
| 65 | N-[(1-Aminoisoquinolin-6-yl)methyl]-5-{[6-(2,2-dimethylpyrrolidin-1-yl)pyridin-3-yl]methyl}pyridine-3-carboxamide |
| 66 | N-[(1-Aminoisoquinolin-6-yl)methyl]-5-{[6-(diethylamino)pyridin-3-yl]methyl}pyridine-3-carboxamide |
| 67 | N-[(1-Aminoisoquinolin-6-yl)methyl]-5-({6-[2-(hydroxymethyl)pyrrolidin-1-yl]pyridin-3-yl}methyl)pyridine-3-carboxamide |
| 68 | N-[(1-Aminoisoquinolin-6-yl)methyl]-5-({6-[3-(dimethylamino)pyrrolidin-1-yl]pyridin-3-yl}methyl)pyridine-3-carboxamide |
| 69 | N-[(1-Aminoisoquinolin-6-yl)methyl]-5-({6-[3-(dimethylamino)pyrrolidin-1-yl]pyridin-3-yl}methyl)pyridine-3-carboxamide |
| 70 | N-[(1-Aminoisoquinolin-6-yl)methyl]-5-[(6-isopropoxypyridin-3-yl)methyl]pyridine-3-carboxamide |
| 71 | N-[(1-Aminoisoquinolin-6-yl)methyl]-5-({6-[3-(hydroxymethyl)pyrrolidin-1-yl]pyridin-3-yl}methyl)pyridine-3-carboxamide |
| 72 | Ethyl 1-{5-[(5-{[(1-aminoisoquinolin-6-yl)methyl]carbamoyl}pyridin-3-yl)methyl]pyridin-2-yl}pyrrolidine-3-carboxylate |
| 73 | N-[(1-Aminoisoquinolin-6-yl)methyl]-5-({6-[isopropyl(methyl)amino]pyridin-3-yl}methyl)pyridine-3-carboxamide |
| 74 | N-[(1-Aminoisoquinolin-6-yl)methyl]-5-{[6-(3,3-dimethylpyrrolidin-1-yl)pyridin-3-yl]methyl}pyridine-3-carboxamide |
| 75 | 1-{5-[(5-{[(1-Aminoisoquinolin-6-yl)methyl]carbamoyl}pyridin-3-yl)methyl]pyridin-2-yl}pyrrolidine-3-carboxylic acid |
| 76 | N-[(1-Aminoisoquinolin-6-yl)methyl]-5-{[2-(2-oxopyrrolidin-1-yl)pyridin-4-yl]methyl}pyridine-3-carboxamide |
| 78 | N-[(1-Aminoisoquinolin-6-yl)methyl]-5-{[2-(piperidin-1-yl)pyridin-4-yl]methyl}pyridine-3-carboxamide |
| 79 | N-[(1-Aminoisoquinolin-6-yl)methyl]-5-{[2-(2-methylpyrrolidin-1-yl)pyridin-4-yl]methyl}pyridine-3-carboxamide |
| 80 | N-[(1-Aminoisoquinolin-6-yl)methyl]-5-{[2-(3,3-difluoropyrrolidin-1-yl)pyridin-4-yl]methyl}pyridine-3-carboxamide |
| 81 | N-[(1-Aminoisoquinolin-6-yl)methyl]-5-{[2-(3-hydroxypyrrolidin-1-yl)pyridin-4-yl]methyl}pyridine-3-carboxamide |
| 82 | N-[(1-Aminoisoquinolin-6-yl)methyl]-5-{[2-(3-fluoropyrrolidin-1-yl)pyridin-4-yl]methyl}pyridine-3-carboxamide |
| 83 | N-[(1-Aminoisoquinolin-6-yl)methyl]-5-{[2-(3-methylpyrrolidin-1-yl)pyridin-4-yl]methyl}pyridine-3-carboxamide |
| 84 | N-[(1-Aminoisoquinolin-6-yl)methyl]-5-{[2-(2,2-dimethylpyrrolidin-1-yl)pyridin-4-yl]methyl}pyridine-3-carboxamide |
| 85 | N-[(1-Aminoisoquinolin-6-yl)methyl]-5-{[2-(morpholin-4-yl)pyridin-4-yl]methyl}pyridine-3-carboxamide |
| 86 | N-[(1-Aminoisoquinolin-6-yl)methyl]-5-{[2-(4-methylpiperazin-1-yl)pyridin-4-yl]methyl}pyridine-3-carboxamide |
| 87 | N-[(1-Aminoisoquinolin-6-yl)methyl]-5-{[2-(diethylamino)pyridin-4-yl]methyl}pyridine-3-carboxamide |

TABLE 10-continued

| Example No | Name |
|---|---|
| 88 | N-[(1-Aminoisoquinolin-6-yl)methyl]-5-{[2-(3-methoxypyrrolidin-1-yl)pyridin-4-yl]methyl}pyridine-3-carboxamide |
| 89 | N-[(1-Aminoisoquinolin-6-yl)methyl]-5-({2-[2-(hydroxymethyl)pyrrolidin-1-yl]pyridin-4-yl}methyl)pyridine-3-carboxamide |
| 90 | N-[(1-Aminoisoquinolin-6-yl)methyl]-5-({2-[3-(dimethylamino)pyrrolidin-1-yl]pyridin-4-yl}methyl)pyridine-3-carboxamide |
| 91 | N-[(1-Aminoisoquinolin-6-yl)methyl]-5-({2-[3-(dimethylamino)pyrrolidin-1-yl]pyridin-4-yl}methyl)pyridine-3-carboxamide |
| 92 | N-[(1-Aminoisoquinolin-6-yl)methyl]-5-({2-[3-(hydroxymethyl)pyrrolidin-1-yl]pyridin-4-yl}methyl)pyridine-3-carboxamide |
| 93 | N-{[4-(Aminomethyl)-2-methylphenyl]methyl}-5-({4-[(4-methylpyrazol-1-yl)methyl]phenyl}methyl)pyridine-3-carboxamide |
| 94 | N-{[4-(Aminomethyl)-2,6-dimethylphenyl]methyl}-5-({4-[(4-methylpyrazol-1-yl)methyl]phenyl}methyl)pyridine-3-carboxamide |
| 95 | N-{[4-(Aminomethyl)-2,6-dimethylphenyl]methyl}-6-({4-[(4-methylpyrazol-1-yl)methyl]phenyl}methyl)pyrazine-2-carboxamide |
| 96 | N-{[4-(Aminomethyl)-3-fluorophenyl]methyl}-5-({4-[(4-methylpyrazol-1-yl)methyl]phenyl}methyl)pyridine-3-carboxamide |

TABLE 11

$^1$H NMR data of examples (solvent d6-DMSO)

| Example No | Chemical Shift (ppm) |
|---|---|
| 8 | 4.22 (2H, s), 4.60 (2H, d, J = 6.3 Hz), 6.72 (2H, s), 6.83 (1H, dd, J = 5.9, 0.8 Hz), 7.22-7.28 (1H, m), 7.31-7.34 (4H, m), 7.40 (1H, dd, J = 8.6, 1.7 Hz), 7.50-7.55 (1H, m), 7.74 (1H, d, J = 5.8 Hz), 7.92 (1H, d, J = 1.3 Hz), 8.11 (1H, d, J = 8.6 Hz), 9.24 (1H, d, J = 1.3 Hz), 9.68 (1H, t, J = 6.4 Hz). |
| 9 | 1.96 (3H, s), 4.21 (2H, s), 4.65 (2H, d, J = 6.3 Hz), 5.18 (2H, s), 6.78 (2H, s), 6.85 (1H, d, J = 5.9 Hz), 7.14 (2H, d, J = 8.1 Hz), 7.21 (1H, s), 7.35 (2H, d, J = 8.1 Hz), 7.43 (1H, dd, J = 8.7, 1.7 Hz), 7.51 (1H, s), 7.56 (1H, s), 7.76 (1H, d, J = 5.8 Hz), 8.14 (1H, d, J = 8.6 Hz), 8.80 (1H, s), 9.04 (1H, s), 9.46 (1H, t, J = 6.3 Hz) |
| 10 | 2.63 (3H, s), 4.44 (2H, s), 4.66 (2H, d, J = 6.3 Hz), 6.71 (2H, s), 6.81 (1H, d, J = 5.9 Hz), 7.37 (1H, d, J = 8.4 Hz), 7.44 (1H, dd,J = 1.7, 8.6 Hz), 7.56 (1H, s), 7.72-7.80 (2H, m), 7.83-7.90 (2H, m), 8.14 (2H, overlapping d, J = 7.4, 8.6 Hz), 8.88 (1H, s), 9.07 (1H, s), 9.47 (1H, t, J = 6.3 Hz). |
| 11 | 1.98 (3H, s), 4.10 (2H, s), 4.64 (2H, d, J = 6.3 Hz), 5.20 (2H, s), 6.70 (2H, s), 6.84 (1H, d, J = 5.2 Hz), 7.15 (2H, d, J = 8.1 Hz), 7.22 (1H, s), 7.28 (2H, d, J = 8.1 Hz), 7.42 (1H, dd, J = 8.7, 1.7 Hz), 7.49-7.55 (2H, m), 7.74 (1H, d, J = 5.8 Hz), 8.00 (1H, d, J = 2.1 Hz), 8.12 (1H, d, J = 8.6 Hz), 9.36 (1H, d, J = 2.2 Hz), 9.90 (1H, t, J = 6.3 Hz). |
| 12 | 1.97 (3H, s), 2.52 (3H, s), 2.57 (3H, s), 3.97 (2H, s), 4.59 (2H, d), 5.17 (2H, s), 6.44 (1H, dd, J = 3.5, 1.9 Hz), 7.09-7.15 (2H, m), 7.17-7.24 (3H, m), 7.29 (1H, dd, J = 3.5, 2.4 Hz), 7.47-7.53 (1H, m), 8.00 (1H, t, J = 2.2 Hz), 8.56 (1H, d, J = 2.1 Hz), 8.61 (1H, t, J = 4.7 Hz), 8.81 (1H, d, J = 2.1 Hz), 11.33 (1H, s). |
| 13 | 2.51 (3H, s), 2.56 (3H, s), 2.62 (3H, s), 4.19 (2H, s), 4.58 (2H, d, J = 4.6 Hz), 6.43 (1H, dd, J = 1.9, 3.5 Hz), 7.29 (1H, dd, J = 2.4, 3.5 Hz), 7.38 (1H, d, J = 8.4 Hz), 7.59 (1H, dd, J = 2.0, 8.7 Hz), 7.75 (1H, d, J = 2.0 Hz), 7.84 (1H, d, J = 8.6 Hz), 8.09 (1H, t, J = 2.1 Hz), 8.17 (1H, d, J = 8.4 Hz), 8.63-8.69 (2H, m), 8.84 (1H, d, J = 2.1 Hz), 11.35 (1H, s). |
| 14 | 4.58 (2H, d, J = 5.7 Hz), 5.31 (2H, s), 6.50 (1H, d, J = 9.6 Hz), 6.74 (2H, s), 6.85 (1H, d, J = 5.6 Hz), 7.40 (1H, d, J = 8.6 Hz), 7.45-7.52 (3H, m), 7.55 (2H, d, J = 4.6 Hz), 7.76 (1H, d, J = 5.8 Hz), 7.82-7.95 (2H, m), 7.99 (1H, dd, J = 2.6 & 9.6 Hz), 8.14 (1H, d, J = 8.6 Hz), 8.59 (1H, d, J = 2.5 Hz), 8.89-9.02 (1H, m). |
| 15 | 1.98 (3H, s), 4.56 (2H, d, J = 5.8 Hz), 5.14 (2H, s), 5.20 (2H, s), 6.47 (1H, d, J = 9.5 Hz), 6.73 (2H, s), 6.86 (1H, d, J = 5.7 Hz), 7.18 (2H, d, J = 8.3 Hz), 7.23 (1H, s), 7.28 (2H, d, J = 8.2 Hz), 7.38 (1H, dd, J = 1.6 & 8.6 Hz), 7.53 (2H, d, J = 6.1 Hz) 7.77 (1H, d, J = 5.8 Hz), 7.94 (1H, dd, J = 2.6 & 9.5 Hz), 8.13 (1H, d, J = 8.6 Hz), 8.49 (1H, d, J = 2.5 Hz), 8.90 (1H, t, J = 5.9 Hz). |
| 16 | 2.64 (3H, s), 4.56 (2H, d, J = 5.8 Hz), 5.34 (2H, s), 6.51 (1H, d, J = 9.5 Hz), 6.73 (2H, s), 6.84 (1H, dd, J = 0.8, 6.0 Hz), 7.35-7.44 (2H, m), 7.54 (1H, d, J = 1.7 Hz), 7.67 (1H, dd, J = 2.0, 8.7 Hz), 7.75 (1H, d, J = 5.8 Hz), 7.78 (1H, d, J = 2.0 Hz), 7.90 (1H, d, J = 8.7 Hz), 7.98 (1H, dd, J = 2.6, 9.5 Hz), 8.12 (1H, d, J = 8.6 Hz), 8.20-8.26 (1H, m), 8.52-8.63 (1H, m), 8.93 (1H, t, J = 5.9 Hz). |
| 17 | 2.63 (3H, s); 4.24 (2H, s); 4.61 (2H, d, J = 5.8 Hz); 6.72 (2H, s), 6.85 (1H, d, J = 5.8 Hz); 7.37-7.43 (2H, m); 7.56 (1H, s); 7.63 (1H, dd, J = 2.0 & 8.6 Hz); 7.76 (1H, d, J = 5.8 Hz); 7.79 (1H, d, J = 1.9 Hz); 7.86 (1H, d, J = 8.6 Hz); 8.10-8.17 (2H, m); 8.19 (1H, d, J = 8.4 Hz); 8.74 (1H, d, J = 2.1 Hz); 8.95 (1H, d, J = 2.1 Hz); 9.30 (1H, t, J = 5.9 Hz). |

TABLE 11-continued

¹H NMR data of examples (solvent d6-DMSO)

| Example No | Chemical Shift (ppm) |
|---|---|
| 18 | 2.62 (3H, s), 3.94 (3H, s), 4.10 (2H, d, J = 1.3 Hz), 4.58 (2H, d, J = 5.8 Hz), 6.73 (2H, s), 6.82-6.88 (1H, m), 7.33-7.43 (2H, m), 7.54 (1H, d, J = 1.7 Hz), 7.59 (1H, dd, J = 2.0, 8.7 Hz), 7.70 (1H, d, J = 1.9 Hz), 7.75 (1H, d, J = 5.8 Hz), 7.84 (1H, d, J = 8.6 Hz), 8.04 (1H, d, J = 2.3 Hz), 8.08-8.20 (2H, m), 8.65 (1H, d, J = 2.3 Hz), 9.12 (1H, t, J = 5.9 Hz). |
| 19 | 2.62 (3H, s), 3.98 (3H, s), 4.14 (2H, s), 4.60 (2H, d, J = 6.1 Hz), 6.69 (2H, s), 6.82 (1H, dd, J = 0.8, 5.9 Hz), 7.36-7.42 (2H, m), 7.54 (1H, d, J = 1.7 Hz), 7.59 (1H, dd, J = 2.0, 8.6 Hz), 7.72-7.78 (2H, m), 7.84 (1H, d, J = 8.6 Hz), 8.03 (1H, d, J = 2.5 Hz), 8.11 (1H, d, J = 8.6 Hz), 8.15-8.20 (1H, m), 8.32 (1H, d, J = 2.5 Hz), 8.87 (1H, t, J = 6.1 Hz). |
| 20 | 2.63 (3H, s), 4.00 (2H, s), 4.64 (2H, d, J = 5.9 Hz), 6.93 (1H, d, J = 6.1 Hz), 7.30 (2H, s), 7.42 (2H, dd, J = 8.7, 22.5 Hz), 7.55-7.63 (2H, m), 7.68-7.78 (3H, m), 7.85 (1H, d, J = 8.6 Hz), 8.15-8.27 (3H, m), 10.32 (1H, t, J = 6.0 Hz), 12.50 (1H, d, J = 6.4 Hz). |
| 21 | 2.63 (3H, s), 2.89 (3H, d, J = 4.5 Hz), 3.98 (2H, s), 4.53 (2H, d, J = 5.9 Hz), 6.69 (3H, d, J = 3.4 Hz), 6.82 (1H, dd, J = 0.8, 6.0 Hz), 7.34-7.40 (2H, m), 7.50 (1H, d, J = 1.7 Hz), 7.57 (1H, dd, J = 2.0, 8.7 Hz), 7.61 (1H, d, J = 2.3 Hz), 7.70 (1H, d, J = 1.9 Hz), 7.74 (1H, d, J = 5.8 Hz), 7.86 (1H, d, J = 8.6 Hz), 8.11 (1H, d, J = 8.6 Hz), 8.16 (1H, d, J = 8.4 Hz), 8.58 (1H, d, J = 2.3 Hz), 8.80 (1H, t, J = 6.0 Hz). |
| 22 | 2.48 (3H, s), 2.63 (3H, s), 4.16 (2H, s), 4.55 (2H, d, J = 5.9 Hz), 6.71 (2H, s), 6.80 (1H, dd, J = 0.8, 5.9 Hz), 7.36-7.43 (2H, m), 7.51-7.57 (1H, m), 7.62 (1H, dd, J = 2.0, 8.6 Hz), 7.69 (1H, d, J = 2.2 Hz), 7.74-7.80 (2H, m), 7.85 (1H, d, J = 8.6 Hz), 8.16 (2H, dd, J = 8.5, 13.6 Hz), 8.50 (1H, d, J = 2.2 Hz), 9.03 (1H, t, J = 6.0 Hz) |
| 23 | 4.05 (2H, s); 4.62 (2H, d, J = 5.8 Hz); 6.72 (2H, s); 6.84-6.89 (1H, m); 7.14-7.26 (1H, m); 7.26-7.35 (4H, m); 7.38-7.45 (1H, m); 7.57 (1H, s); 7.77 (1H, d, J = 5.8 Hz); 8.10 (1H, t, J = 2.2 Hz); 8.14 (1H, d, J = 8.6 Hz); 8.67 (1H, d, J = 2.1 Hz); 8.94 (1H, d, J = 2.1 Hz); 9.30 (1H, t, J = 6.0 Hz). |
| 24 | 4.25 (2H, s); 4.63 (2H, d, J = 5.9 Hz); 6.71 (2H, s); 6.85 (1H, d, J = 5.6 Hz); 7.42 (1H, dd, J = 1.7 & 8.6 Hz); 7.44-7.52 (4H, m); 7.57 (1H, s); 7.76 (1H, d, J = 5.8 Hz); 7.88-7.94 (2H, m); 8.14 (1H, d, J = 8.6 Hz); 8.21 (1H, t, J = 2.1 Hz); 8.74 (1H, d, J = 2.1 Hz); 8.97 (1H, d, J = 2.1 Hz); 9.32 (1H, t, J = 5.9 Hz). |
| 25 | 9.29 (t, J = 5.9 Hz, 1H), 8.93 (d, J = 2.1 Hz, 1H), 8.66 (d, J = 2.1 Hz, 1H), 8.14 (d, J = 8.6 Hz, 1H), 8.09 (t, J = 2.1 Hz, 1H), 7.76 (d, J = 5.8 Hz, 1H), 7.56 (s, 1H), 7.41 (dd, J = 8.6, 1.7 Hz, 1H), 7.25-7.19 (m, 1H), 6.89-6.81 (m, 2H), 6.78 (ddd, J = 8.2, 2.6, 0.8 Hz, 1H), 6.72 (s, 2H), 4.61 (d, J = 5.9 Hz, 2H), 4.01 (s, 2H), 3.72 (s, 3H). |
| 26 | 3.71 (3H, s), 3.97 (2H, s), 4.61 (2H, d, J = 5.9 Hz), 6.71 (2H, s), 6.81-6.92 (3H, m), 7.14-7.23 (2H, m), 7.40 (1H, dd, J = 1.7 & 8.6 Hz), 7.54-7.60 (1H, m), 7.76 (1H, d, J = 5.8 Hz), 8.05 (1H, t, J = 2.2 Hz), 8.14 (1H, d, J = 8.6 Hz), 8.63 (1H, d, J = 2.1 Hz), 8.91 (1H, d, J = 2.1 Hz), 9.28 (1H, t, J = 5.9 Hz). |
| 27 | 2.50 (4H, s), 4.09 (2H, s), 4.61 (2H, d, J = 5.9 Hz), 6.52 (1H, d of ds, J = 1.8 & 2.4 Hz), 6.78 (2H, s), 6.86 (1H, d, J = 5.8 Hz), 7.37-7.45 (4H, m), 7.57 (1H, s), 7.69-7.81 (4H, m), 8.09-8.18 (2H, m), 8.42-8.48 (1H, m), 8.69 (1H, d, J = 2.1 Hz), 8.94 (1H, d, J = 2.1 Hz), 9.31 (1H, t, J = 5.9 Hz). |
| 28 | 4.28 (2H, s), 4.60 (2H, d, J = 5.9 Hz), 6.70 (2H, s), 6.84 (1H, d, J = 5.9 Hz), 7.40 (1H, dd, J = 8.6, 1.8 Hz), 7.55 (1H, s), 7.71 (1H, dd, J = 8.4, 1.8 Hz), 7.75 (1H, d, J = 5.8 Hz), 7.78 (1H, d, J = 5.7 Hz), 7.92 (1H, d, J = 8.5 Hz), 8.00 (1H, s), 8.09-8.19 (2H, m), 8.46 (1H, d, J = 5.7 Hz), 8.74 (1H, d, J = 2.1 Hz), 8.95 (1H, d, J = 2.1 Hz), 9.23-9.32 (2H, m). |
| 29 | 3.77 (3H, s), 3.97 (2H, s), 4.60 (2H, d, J = 5.8 Hz), 6.77 (2H, s), 6.83-6.93 (2H, m), 6.98 (1H, d, J = 7.7 Hz), 7.17-7.27 (2H, m), 7.40 (1H, dd, J = 8.6, 1.6 Hz), 7.56 (1H, s), 7.75 (1H, d, J = 5.8 Hz), 8.03 (1H, t, J = 2.1 Hz), 8.14 (1H, d, J = 8.6 Hz), 8.59 (1H, d, J = 2.1 Hz), 8.90 (1H, d, J = 2.1 Hz), 9.30 (1H, t, J = 5.9 Hz). |
| 30 | 4.13 (2H, s), 4.61 (2H, d, J = 5.8 Hz), 6.51-6.55 (1H, m), 6.77 (2H, s), 6.86 (1H, d, J = 5.8 Hz), 7.22 (1H, d, J = 7.6 Hz), 7.38-7.46 (2H, m), 7.57 (1H, s), 7.66-7.71 (1H, m), 7.72 (1H, d, J = 1.5 Hz), 7.75 (1H, d, J = 5.8 Hz), 7.81 (1H, s), 8.14 (2H, m), 8.47 (1H, d, J = 2.4 Hz), 8.72 (1H, d, J = 2.0 Hz), 8.95 (1H, d, J = 2.0 Hz), 9.30 (1H, t, J = 5.9 Hz). |
| 31 | 4.27 (2H, s), 4.60 (2H, d, J = 5.9 Hz), 6.79 (2H, s), 6.85 (1H, d, J = 5.8 Hz), 7.41 (1H, dd, J = 8.6, 1.7 Hz), 7.51 (1H, dd, J = 8.3, 4.2 Hz), 7.56 (1H, s), 7.69 (1H, dd, J = 8.7, 2.0 Hz), 7.74 (1H, d, J = 5.8 Hz), 7.85 (1H, d, J = 1.7 Hz), 7.97 (1H, d, J = 8.6 Hz), 8.11-8.16 (2H, m), 8.31 (1H, dd, J = 8.4, 1.0 Hz), 8.74 (1H, d, J = 2.1 Hz), 8.85 (1H, dd, J = 4.2, 1.7 Hz), 8.95 (1H, d, J = 2.1 Hz), 9.29 (1H, t, J = 5.9 Hz). |
| 32 | 4.02 (2H, s), 4.61 (2H, d, J = 5.9 Hz), 5.29 (2H, s), 6.23 (1H, t, J = 2.1 Hz), 6.72 (2H, s), 6.86 (1H, d, J = 5.6 Hz), 7.01 (1H, d, J = 7.6 Hz), 7.15 (1H, s), 7.19 (1H, d, J = 7.8 Hz), 7.27 (1H, t, J = 7.6 Hz), 7.39-7.44 (2H, m), 7.57 (1H, d, J = 1.7 Hz), 7.76 (1H, d, 5.8 Hz), 7.78 (1H, dd, J = 2.3, 0.6 Hz), 8.07 (1H, t, J = 2.1 Hz), 8.14 (1H, d, J = 8.6 Hz), 8.62 (1H, d, J = 2.1 Hz), 8.93 (1H, d, J = 2.1 Hz), 9.28 (1H, t, J = 5.9 Hz). |
| 33 | 1.97 (3H, d, J = 0.8 Hz), 3.80 (3H, s), 4.01 (2H, s), 4.61 (2H, d, J = 5.8 Hz), 5.13 (2H, s), 6.72-6.82 (4H, m), 6.86 (1H, d, J = 8.6 Hz), 6.99 (1H, s), 7.20 (1H, s), 7.37-7.44 (2H, m), 7.56 (1H, d, J = 1.6 Hz), 7.76 (1H, d, J = 5.8 Hz), 8.09 (1H, t, J = 2.1 Hz), 8.14 (1H, d, J = 8.6 Hz), 8.66 (1H, d, J = 2.1 Hz), 8.92 (1H, d, J = 2.1 Hz), 9.27 (1H, t, J = 5.9 Hz). |
| 34 | 3.28 (3H, s); 3.59-3.65 (2H, m); 3.97 (2H, s); 4.00-4.08 (2H, m); 4.61 (2H, d, J = 5.8 Hz); 6.71 (2H, s); 6.83-6.91 (3H, m); 7.14-7.22 (2H, m); 7.40 (1H, dd, J = 1.6 & 8.7 Hz); 7.56 (1H, s); 7.76 (1H, d, J = 5.8 Hz); 8.06 (1H, t, J = 2.1 Hz); |

TABLE 11-continued $^1$H NMR data of examples (solvent d6-DMSO)

| Example No | Chemical Shift (ppm) |
|---|---|
| | 8.13 (1H, d, J = 8.5 Hz); 8.63 (1H, d, J = 2.1 Hz); 8.91 (1H, d, J = 2.1 Hz); 9.28 (1H, t, J = 5.9 Hz). |
| 35 | 2.42-2.50 (4H, m), 2.77-3.08 (4H, m), 3.57 (2H, s), 4.61 (2H, d, J = 5.8 Hz), 6.74 (2H, s), 6.86 (1H, dd, J = 0.8, 6.0 Hz), 7.41 (1H, dd, J = 1.7, 8.7 Hz), 7.54-7.60 (1H, m), 7.60-7.70 (2H, m), 7.69-7.84 (4H, m), 8.09 (1H, t, J = 2.2 Hz), 8.14 (1H, d, J = 8.6 Hz), 8.58 (1H, d, J = 2.0 Hz), 8.96 (1H, d, J = 2.2 Hz), 9.29 (1H, t, J = 5.9 Hz). |
| 36 | 2.35-2.50 (4H, m), 3.62 (4H, br s), 4.65 (2H, d, J = 5.8 Hz), 6.92 (1H, d, J = 6.0 Hz), 7.00 (2H, s), 7.33 7.52 (6H, m), 7.63 (1H, d, J = 1.6 Hz), 7.76 (1H, d, J = 5.9 Hz), 8.09 8.23 (2H, m), 8.66 (1H, d, J = 2.0 Hz), 9.00 (1H, d, J = 2.1 Hz); 9.35 (1H, t, J = 5.9 Hz). |
| 37 | 1.13-1.27 (2H, m), 1.37-1.48 (2H, m), 1.67-1.81 (1H, m), 1.86-1.96 (2H, m), 1.98 (3H, s), 2.77 (2H, d, J = 11.4 Hz), 3.53 (2H, s), 3.90 (2H, d, J = 7.1 Hz), 4.64 (2H, d, J = 5.8 Hz), 6.73 (2H, s), 6.88 (1H, d, J = 5.6 Hz); 7.20 (1H, s), 7.40-7.45 (2H, m), 7.59 (1H, s), 7.77 (1H, d, J = 5.8 Hz), 8.11-8.18 (2H, m), 8.61 (1H, d, J = 2.0 Hz), 8.97 (1H, d, J = 2.1 Hz), 9.33 (1H, t, J = 6.0 Hz). |
| 38 | 2.77 (3H, s), 3.133.19 (2H, m), 3.84 (2H, s), 4.16-4.21 (2H, m), 4.61 (2H, d, J = 5.8 Hz), 6.57 (1H, d, J = 2.0 Hz), 6.61 (1H, d, J = 8.2 Hz), 6.67 (1H, dd, J = 2.0, 8.2 Hz), 6.72 (2H, s), 6.86 (1H, dd, J = 0.8, 5.9 Hz), 7.41 (1H, dd, J = 1.8, 8.6 Hz), 7.52-7.59 (1H, m), 7.76 (1H, d, J = 5.8 Hz), 8.04 (1H, t, J = 2.2 Hz), 8.14 (1H, d, J = 8.6 Hz), 8.61 (1H, d, J = 2.1 Hz), 8.90 (1H, d, J = 2.1 Hz), 9.28 (1H, t, J = 5.9 Hz) |
| 39 | 2.51-2.57 (4H, m), 3.09-3.17 (4H, m), 3.63 (2H, s), 4.64 (2H, d, J = 5.8 Hz), 6.71 (2H, s), 6.76 (1H, t, J = 7.3 Hz), 6.87 (1H, d, J = 5.7 Hz), 6.91 (2H, d, J = 7.9 Hz), 7.19 (2H, dd, J = 7.3 & 8.7 Hz), 7.43 (1H, dd, J = 1.7 & 8.6 Hz), 7.59 (1H, s), 7.76 (1H, d, J = 5.8 Hz), 8.15 (1H, d, J = 8.6 Hz), 8.21 (1H, t, J = 2.1 Hz), 8.67 (1H, d, J = 2.0 Hz), 9.00 (1H, d, J = 2.1 Hz), 9.34 (1H, t, J = 5.9 Hz). |
| 40 | 1.99 (3H, s); 2.11 (3H, s); 4.43 (2H, t, J = 5.3 Hz); 4.61 (4H, d of ts, J = 4.4 & 5.7 Hz); 6.81 (2H, s); 6.85-6.93 (1H, m); 7.23 (1H, s); 7.41 (1H, dd, J = 1.8 & 8.7 Hz); 7.50 (1H, t, J = 0.9 Hz); 7.56 (1H, d, J = 1.7 Hz); 7.75 (1H, d, J = 5.8 Hz); 8.03 (1H, dd, J = 1.0 & 2.4 Hz); 8.15 (1H, d, J = 8.6 Hz); 8.53-8.58 (1H, m); 9.08 (1H, t, J = 6.0 Hz). |
| 41 | 2.40 (8H, s), 3.46 (2H, s), 3.56 (2H, s), 4.64 (2H, d, J = 5.9 Hz), 6.72 (2H, s), 6.88 (1H, d, J = 5.6 Hz), 7.20-7.35 (5H, m), 7.43 (1H, dd, J = 1.7 & 8.6 Hz), 7.59 (1H, s), 7.77 (1H, d, J = 5.8 Hz), 8.12-8.18 (2H, m), 8.62 (1H, d, J = 2.0 Hz), 8.98 (1H, d, J = 2.1 Hz), 9.33 (1H, t, J = 5.9 Hz). |
| 42 | 2.45 (8H, s), 3.55 (4H, d, J = 19.0 Hz), 3.76 (3H, s), 4.64 (2H, d, J = 5.8 Hz), 6.88 6.99 (5H, m), 7.18 7.26 (1H, m), 7.29 (1H, dd, J = 1.8 & 7.4 Hz), 7.45 (1H, dd, J = 1.8, 8.6 Hz), 7.61 (1H, d, J = 1.6 Hz), 7.75 (1H, d, J = 5.9 Hz), 8.13-8.21 (2H, m), 8.62 (1H, d, J = 2.0 Hz), 8.98 (1H, d, J = 2.1 Hz), 9.34 (1H, t, J = 5.9 Hz). |
| 43 | 1.08-1.19 (2H, m), 1.39-1.57 (4H, s), 1.59-1.69 (2H, s), 2.02 (1H, quintet, J = 7.4 Hz), 2.16 (2H, t, J = 7.5 Hz), 2.22-2.47 (8H, m), 3.55 (2H, s), 4.63 (2H, d, J = 5.8 Hz), 6.73 (2H, s), 6.87 (1H, d, J = 5.7 Hz), 7.42 (1H, dd, J = 1.7 & 8.6 Hz), 7.56-7.60 (1H, m), 7.76 (1H, d, J = 5.8 Hz), 8.15 (2H, dd, J = 3.2 & 5.3 Hz), 8.62 (1H, d, J = 2.0 Hz), 8.98 (1H, d, J = 2.1 Hz), 9.33 (1H, t, J = 6.0 Hz). |
| 45 | 2.18-2.46 (8H, m), 3.38 (2H, s), 3.55 (2H, s), 3.72 (3H, s), 4.63 (2H, d, J = 5.8 Hz), 6.75 (2H, s), 6.86 (3H, dd, J = 3.2 & 9.9 Hz), 7.18 (2H, d, J = 8.7 Hz), 7.43 (1H, dd, J = 1.7 & 8.6 Hz), 7.58 (1H, s), 7.76 (1H, d, J = 5.8 Hz), 8.15 (2H, dd, J = 2.9 & 5.0 Hz), 8.61 (1H, d, J = 2.0 Hz), 8.97 (1H, d, J = 2.1 Hz), 9.32 (1H, t, J = 5.9 Hz). |
| 46 | 2.23-2.47 (8H, m), 3.47 (2H, s), 3.56 (2H, s), 4.63 (2H, d, J = 5.8 Hz), 6.73 (2H, s), 6.87 (1H, d, J = 5.7 Hz), 7.02-7.15 (3H, m), 7.34 (1H, td, J = 6.4 & 8.0 Hz), 7.42 (1H, dd, J = 1.7 & 8.6 Hz), 7.58 (1H, s), 7.76 (1H, d, J = 5.8 Hz), 8.12-8.20 (2H, m), 8.62 (1H, d, J = 2.0 Hz), 8.97 (1H, d, J = 2.1 Hz), 9.32 (1H, t, J = 5.9 Hz). |
| 47 | 2.16-2.47 (8H, m), 3.31 (2H, s), 3.54 (2H, s), 3.77 (3H, s), 4.63 (2H, d, J = 5.9 Hz), 6.74 (2H, s), 6.87 (1H, d, J = 5.6 Hz), 7.26 (1H, s), 7.42 (1H, dd, J = 1.6 & 8.7 Hz), 7.52 (1H, s), 7.58 (1H, s), 7.76 (1H, d, J = 5.9 Hz), 8.09-8.19 (2H, m), 8.61 (1H, d, J = 1.9 Hz), 8.97 (1H, d, J = 2.1 Hz), 9.32 (1H, t, J = 6.0 Hz). |
| 48 | 2.39 (8H, s), 3.44 (2H, s), 3.56 (2H, s), 4.64 (2H, d, J = 5.8 Hz), 6.73 (2H, s), 6.88 (1H, dd, J = 0.8, 5.9 Hz), 7.07-7.18 (2H, m), 7.26-7.36 (2H, m), 7.43 (1H, dd, J = 1.7, 8.6 Hz), 7.59 (1H, d, J = 1.7 Hz), 7.77 (1H, d, J = 5.8 Hz), 8.15 (2H, dd, J = 3.1, 5.2 Hz), 8.62 (1H, d, J = 2.0 Hz), 8.98 (1H, d, J = 2.1 Hz), 9.33 (1H, t, J = 5.9 Hz). |
| 49 | 2.25-2.47 (8H, m), 3.44 (2H, s), 3.56 (2H, s), 3.72 (3H, s), 4.63 (2H, d, J = 5.8 Hz), 6.76-6.90 (6H, m), 7.21 (1H, t, J = 8.0 Hz), 7.43 (1H, dd, J = 1.7 & 8.6 Hz), 7.59 (1H, s), 7.76 (1H, d, J = 5.8 Hz), 8.15 (2H, dd, J = 2.9 & 5.0 Hz), 8.62 (1H, d, J = 2.0 Hz), 8.97 (1H, d, J = 2.1 Hz), 9.33 (1H, t, J = 5.9 Hz). |
| 50 | 1.67-1.75 (2H, m), 2.29-2.35 (2H, m), 2.36-2.47 (8H, m), 2.54-2.60 (2H, m), 3.56 (2H, s), 4.63 (2H, d, J = 5.9 Hz), 6.78 (2H, s), 6.88 (1H, d, J = 5.8 Hz), 7.17 (3H, dd, J = 7.0 & 15.3 Hz), 7.23-7.29 (2H, m), 7.43 (1H, dd, J = 1.6 & 8.6 Hz), 7.59 (1H, s), 7.76 (1H, d, J = 5.8 Hz), 8.15 (2H, dd, J = 2.7 & 4.7 Hz), 8.62 (1H, d, J = 2.0 Hz), 8.98 (1H, d, J = 2.1 Hz), 9.33 (1H, t, J = 5.8 Hz). |
| 51 | 2.30-2.47 (8H, d), 2.51-2.54 (2H, m), 2.69-2.76 (2H, m), 3.57 (2H, s), 4.64 (2H, d, J = 5.8 Hz), 6.77 (2H, s), 6.89 (1H, d, J = 5.8 Hz), 7.15-7.24 (3H, m), 7.24-7.30 (2H, m), 7.44 (1H, dd, J = 1.6 & 8.6 Hz), 7.60 (1H, s,) 7.77 (1H, d, J = 5.8 Hz), 8.16 (2H, d, J = 8.4 Hz), 8.64 (1H, d, J = 2.0 Hz), 8.99 (1H, d, J = 2.1 Hz), 9.35 (1H, t, J = 5.9 Hz). |

TABLE 11-continued

¹H NMR data of examples (solvent d6-DMSO)

| Example No | Chemical Shift (ppm) |
|---|---|
| 52 | 2.38-2.48 (4H, s), 2.57-2.69 (4H, d, J = 48.2 Hz), 3.13 (2H, s), 3.57 (2H, s), 4.63 (2H, d, J = 5.8 Hz), 6.77 (2H, s), 6.88 (1H, d, J = 5.8 Hz), 7.43 (1H, dd, J = 1.6 & 8.6 Hz), 7.59 (1H, s), 7.76 (1H, d, J = 5.8 Hz), 8.13-8.18 (2H, m), 8.63 (1H, d, J = 2.0 Hz), 8.98 (1H, d, J = 2.1 Hz), 9.33 (1H, t, J = 5.9 Hz). |
| 53 | 1.98-2.05 (2H, m), 2.53-2.59 (2H, m), 3.92-3.99 (2H, m), 4.05 (2H, s), 4.62 (2H, d, J = 5.8 Hz), 6.71 (2H, s), 6.87 (1H, d, J = 5.6 Hz), 7.41 (1H, dd, J = 1.7 & 8.6 Hz), 7.57 (1H, s), 7.72 (1H, dd, J = 2.4 & 8.6 Hz), 7.76 (1H, d, J = 5.8 Hz), 8.09 (1H, t, J = 2.1 Hz), 8.14 (1H, d, J = 8.6 Hz), 8.21-8.27 (1H, m), 8.37 (1H, d, J = 1.8 Hz), 8.68 (1H, d, J = 2.1 Hz), 8.94 (1H, d, J = 2.1 Hz), 9.29 (1H, t, J = 5.9 Hz). |
| 54 | 4.09 (2H, s), 4.62 (2H, d, J = 5.8 Hz), 6.71 (2H, s), 6.86 (1H, d, J = 5.9 Hz), 7.13 (1H, dd, J = 8.5, 2.9 Hz), 7.41 (1H, dd, J = 8.6, 1.7 Hz), 7.57 (1H, s), 7.76 (1H, d, J = 5.8 Hz), 7.90 (1H, td, J = 8.2, 2.6 Hz), 8.09-8.18 (2H, m), 8.24 (1H, s), 8.70 (1H, d, J = 2.1 Hz), 8.94 (1H, d, J = 2.1 Hz), 9.29 (1H, t, J = 5.9 Hz). |
| 55 | 1.86-1.94 (4H, m), 3.29-3.34 (4H, m), 3.87 (2H, s), 4.61 (2H, d, J = 5.8 Hz), 6.37 (1H, d, J = 8.6 Hz), 6.74 (2H, s), 6.86 (1H, d, J = 6.2 Hz), 7.36 (1H, dd, J = 8.6, 2.5 Hz), 7.40 (1H, dd, J = 8.6, 1.8 Hz), 7.56 (1H, s), 7.75 (1H, d, J = 5.8 Hz), 8.00-8.07 (2H, m), 8.13 (1H, d, J = 8.6 Hz), 8.63 (1H, d, J = 2.1 Hz), 8.91 (1H, d, J = 2.1 Hz), 9.31 (1H, t, J = 5.9 Hz). |
| 56 | 1.44-1.63 (6H, m), 3.40-3.49 (4H, m), 3.88 (2H, s), 4.61 (2H, d, J = 5.9 Hz), 6.66-6.78 (3H, m), 6.86 (1H, d, J = 6.0 Hz), 7.36-7.43 (2H, m), 7.56 (1H, s), 7.76 (1H, d, J = 5.8 Hz), 8.03-8.09 (2H, m), 8.14 (1H, d, J = 8.6 Hz), 8.64 (1H, d, J = 2.1 Hz), 8.91 (1H, d, J = 2.1 Hz), 9.28 (1H, t, J = 5.9 Hz). |
| 57 | 2.46 (1H, d, J = 7.4 Hz), 2.522.56 (1H, m), 3.57 (2H, t, J = 7.3 Hz), 3.78 (2H, t, J = 13.4 Hz), 3.92 (2H, s), 4.61 (2H, d, J = 5.9 Hz), 6.51 (1H, dd, J = 0.9, 8.7 Hz), 6.76 (2H, s), 6.87 (1H, dd, J = 0.8, 5.9 Hz), 7.41 (1H, dd, J = 1.8, 8.6 Hz), 7.46 (1H, dd, J = 2.4, 8.6 Hz), 7.56 (1H, d, J = 1.9 Hz), 7.75 (1H, d, J = 5.8 Hz), 8.05 (1H, t, J = 2.1 Hz), 8.09 (1H, dd, J = 0.8, 2.5 Hz), 8.14 (1H, d, J = 8.6 Hz), 8.64 (1H, d, J = 2.1 Hz), 8.91 (1H, d, J = 2.1 Hz), 9.29 (1H, t, J = 5.9 Hz) |
| 58 | 1.11 (3H, d, J = 6.2 Hz), 1.59-1.69 (1H, m), 1.872.05 (3H, m), 3.17-3.24 (1H, m), 3.37-3.46 (1H, m), 3.87 (2H, s), 4.02-4.10 (1H, m), 4.61 (2H, d, J = 5.8 Hz), 6.38 (1H, dd, J = 0.8, 8.6 Hz), 6.72 (2H, s), 6.86 (1H, dd, J = 0.8, 6.0 Hz), 7.35 (1H, dd, J = 2.5, 8.6 Hz), 7.40 (1H, dd, J = 1.7, 8.6 Hz), 7.56 (1H, d, J = 1.7 Hz), 7.76 (1H, d, J = 5.8 Hz), 7.99-8.08 (2H, m), 8.13 (1H, d, J = 8.6 Hz), 8.63 (1H, d, J = 2.1 Hz), 8.91 (1H, d, J = 2.1 Hz), 9.29 (1H, t, J = 5.9 Hz). |
| 59 | 1.87 (1H, m), 1.98 (1H, m), 3.25 (1H, m), 3.37-3.46 (3H, m), 4.35 (1H, m), 4.61 (2H, doublet, J = 5.8 Hz), 4.90 (1H, d, J = 3.7 Hz), 6.37 (1H, dd, J = 0.8, 8.6 Hz), 6.75 (2H, s), 6.84-6.89 (1H, m), 7.36 (1H, dd, J = 2.4, 8.6 Hz), 7.41 (1H, dd, J = 1.8, 8.6 Hz), 7.50-7.61 (1H, m), 7.75 (1H, d, J = 5.8 Hz), 7.98-8.07 (2H, m), 8.14 (1H, d, J = 8.6 Hz), 8.63 (1H, d, J = 2.1 Hz), 8.91 (1H, d, J = 2.1 Hz), 9.29 (1H, t, J = 5.9 Hz) |
| 60 | 2.03-2.31 (2H, m), 3.34-3.43 (1H, m), 3.47-3.71 (3H, m), 3.90 (2H, s), 4.61 (2H, d, J = 5.8 Hz), 5.31-5.52 (1H, m), 6.44 (1H, dd, J = 0.8, 8.6 Hz), 6.71 (2H, s), 6.86 (1H, dd, J = 0.8, 5.9 Hz), 7.41 (2H, dt, J = 2.3, 8.7 Hz), 7.52-7.61 (1H, m), 7.76 (1H, d, J = 5.8 Hz), 8.00-8.09 (2H, m), 8.13 (1H, d, J = 8.6 Hz), 8.64 (1H, d, J = 2.1 Hz), 8.91 (1H, d, J = 2.1 Hz), 9.28 (1H, t, J = 5.9 Hz) |
| 61 | 1.05 (3H, d, J = 6.6 Hz), 1.53 (1H, m), 2.05 (1H, m), 2.25-2.35 (1H, m), 2.86 (1H, dd, J = 7.6, 10.1 Hz), 3.25-3.30 (1H, m), 3.45 (1H, m), 3.53 (1H, dd, J = 7.2, 10.0 Hz), 3.87 (2H, s), 4.61 (2H, d, J = 5.9 Hz), 6.35 (1H, dd, J = 0.8, 8.7 Hz), 6.76 (2H, s), 6.87 (1H, dd, J = 0.8, 6.0 Hz), 7.35 (1H, dd, J = 2.5, 8.6 Hz), 7.41 (1H, dd, J = 1.8, 8.7 Hz), 7.56 (1H, d, J = 1.7 Hz), 7.75 (1H, d, J = 5.8 Hz), 8.00-8.06 (2H, m), 8.14 (1H, d, J = 8.6 Hz), 8.63 (1H, d, J = 2.1 Hz), 8.91 (1H, d, J = 2.1 Hz), 9.29 (1H, t, J = 5.9 Hz) |
| 62 | 2.02 (2H, m), 3.24 (3H, s), 3.30 (1H, d, J = 1.9 Hz), 3.39-3.45 (3H, m), 3.88 (2H, s), 4.04 (1H, m), 4.61 (2H, d, J = 5.9 Hz), 6.39 (1H, d, J = 8.6 Hz), 6.90 (1H, d, J = 6.0 Hz), 6.92 (2H, s), 7.37 (1H, dd, J = 2.4, 8.6 Hz), 7.43 (1H, dd, J = 1.8, 8.6 Hz), 7.59 (1H, d, J = 1.8 Hz), 7.74 (1H, d, J = 5.8 Hz), 7.97-8.08 (2H, m), 8.17 (1H, d, J = 8.6 Hz), 8.63 (1H, d, J = 2.1 Hz), 8.91 (1H, d, J = 2.1 Hz), 9.30 (1H, t, J = 5.9 Hz) |
| 63 | 3.37 (4H, dd, J = 4.1, 5.7 Hz), 3.64-3.69 (4H, m), 3.92 (2H, s), 4.61 (2H, d, J = 5.9 Hz), 6.76 (2H, s), 6.78 (1H, d, J = 8.8 Hz), 6.87 (1H, d, J = 5.8 Hz), 7.41 (1H, dd, J = 1.7, 8.7 Hz), 7.46 (1H, dd, J = 2.5, 8.7 Hz), 7.57 (1H, d, J = 1.7 Hz), 7.76 (1H, d, J = 5.8 Hz), 8.06 (1H, t, J = 2.1 Hz), 8.11 (1H, d, J = 2.5 Hz), 8.14 (1H, d, J = 8.6 Hz), 8.65 (1H, d, J = 2.1 Hz), 8.92 (1H, d, J = 2.1 Hz), 9.29 (1H, t, J = 5.9 Hz) |
| 64 | 2.28 (3H, s), 2.45-2.49 (4H, m), 3.40-3.51 (4H, m), 3.91 (2H, s), 4.61 (2H, d, J = 5.9 Hz), 6.79 (1H, d, J = 8.8 Hz), 6.83 (2H, s), 6.88 (1H, d, J = 5.9 Hz), 7.43 (2H, m), 7.57 (1H, d, J = 1.7 Hz), 7.75 (1H, d, J = 5.8 Hz), 8.06 (1H, t, J = 2.2 Hz), 8.09 (1H, d, J = 2.4 Hz), 8.15 (1H, d, J = 8.6 Hz), 8.65 (1H, d, J = 2.1 Hz), 8.92 (1H, d, J = 2.1 Hz), 9.30 (1H, t, J = 5.9 Hz) |
| 65 | 1.44 (6H, s), 1.78-1.90 (4H, m), 3.31 (2H, m), 3.86 (2H, s), 4.61 (2H, d, J = 5.8 Hz), 6.36 (1H, d, J = 8.7 Hz), 6.70 (2H, s), 6.86 (1H, d, J = 5.8 Hz), 7.32 (1H, dd, J = 2.5, 8.7 Hz), 7.41 (1H, dd, J = 1.7, 8.6 Hz), 7.56 (1H, d, J = 1.7 Hz), 7.76 (1H, d, J = 5.8 Hz), 8.01 (1H, d, J = 2.5 Hz), 8.07 (1H, t, J = 2.2 Hz), 8.13 (1H, d, J = 8.6 Hz), 8.64 (1H, d, J = 2.1 Hz), 8.91 (1H, d, J = 2.1 Hz), 9.29 (1H, t, J = 5.9 Hz) |
| 66 | 1.06 (6H, t, J = 7.0 Hz), 3.44 (4H, q, J = 7.0 Hz), 3.86 (2H, s), 4.61 (2H, d, J = 5.8 Hz), 6.51 (1H, d, J = 8.7 Hz), 6.73 (2H, s), 6.87 (1H, d, J = 5.8 Hz), 7.34 (1H, dd, |

TABLE 11-continued

<sup>1</sup>H NMR data of examples (solvent d6-DMSO)

| Example No | Chemical Shift (ppm) |
|---|---|
| | J = 2.5, 8.7 Hz), 7.41 (1H, d, J = 8.6 Hz), 7.57 (1H, s), 7.76 (1H, d, J = 5.8 Hz), 8.01 (1H, d, J = 2.5 Hz), 8.07 (1H, s), 8.14 (1H, d, J = 8.6 Hz), 8.64 (1H, d, J = 2.0 Hz), 8.91 (1H, d, J = 2.1 Hz), 9.29 (1H, t, J = 5.8 Hz) |
| 67 | 1.80-1.99 (4H, m), 3.13-3.27 (2H, m), 3.36-3.43 (1H, m), 3.54 (1H, dt, J = 4.6, 9.7 Hz), 3.88 (2H, s), 3.96 (1H, m), 4.61 (2H, d, J = 5.8 Hz), 4.87 (1H, dd, J = 5.0, 6.1 Hz), 6.44 (1H, d, J = 8.6 Hz), 6.70 (2H, s), 6.82-6.89 (1H, m), 7.39 (2H, ddd, J = 2.1, 8.6, 11.2 Hz), 7.53-7.60 (1H, m), 7.76 (1H, d, J = 5.8 Hz), 8.01-8.03 (1H, m), 8.05 (1H, t, J = 2.1 Hz), 8.13 (1H, d, J = 8.6 Hz), 8.64 (1H, d, J = 2.1 Hz), 8.91 (1H, d, J = 2.1 Hz), 9.28 (1H, t, J = 5.9 Hz) |
| 68 | 1.76 (1H, dq, J = 9.5, 11.9 Hz), 2.08-2.14 (1H, m), 2.18 (6H, s), 2.66-2.77 (1H, m), 3.05 (1H, dd, J = 8.1, 10.0 Hz), 3.22-3.29 (1H, m), 3.51 (1H, ddd, J = 2.2, 8.8, 10.6 Hz), 3.61 (1H, dd, J = 7.1, 10.0 Hz), 3.88 (2H, s), 4.61 (2H, d, J = 5.9 Hz), 6.40 (1H, d, J = 8.6 Hz), 6.71 (2H, s), 6.86 (1H, d, J = 5.8 Hz), 7.39 (2H, ddd, J = 2.1, 8.6, 13.7 Hz), 7.56 (1H, d, J = 1.7 Hz), 7.76 (1H, d, J = 5.8 Hz), 8.03 (2H, q, J = 2.3 Hz), 8.13 (1H, d, J = 8.6 Hz), 8.63 (1H, d, J = 2.1 Hz), 8.91 (1H, d, J = 2.1 Hz), 9.28 (1H, t, J = 6.0 Hz) |
| 69 | 1.76 (1H, dq, J = 9.5, 12.0 Hz), 2.09-2.14 (1H, m), 2.18 (6H, s), 2.71 (1H, m), 3.05 (1H, dd, J = 8.1, 10.1 Hz), 3.24-3.29 (1H, m), 3.51 (1H, ddd, J = 2.2, 8.7, 10.6 Hz), 3.61 (1H, dd, J = 7.1, 10.0 Hz), 3.88 (2H, s), 4.61 (2H, d, J = 5.9 Hz), 6.40 (1H, d, J = 8.6 Hz), 6.71 (2H, s), 6.86 (1H, d, J = 5.8 Hz), 7.37 (1H, dd, J = 2.5, 8.6 Hz), 7.40 (1H, dd, J = 1.8, 8.6 Hz), 7.56 (1H, d, J = 1.7 Hz), 7.76 (1H, d, J = 5.8 Hz), 8.03 (2H, q, J = 2.3 Hz), 8.13 (1H, d, J = 8.6 Hz), 8.63 (1H, d, J = 2.1 Hz), 8.91 (1H, d, J = 2.1 Hz), 9.28 (1H, t, J = 5.9 Hz) |
| 70 | 1.25 (6H, d, J = 6.2 Hz), 3.97 (2H, s), 4.61 (2H, d, J = 5.8 Hz), 5.19 (1H, h, J = 6.2 Hz), 6.67 (1H, dd, J = 0.7, 8.5 Hz), 6.71 (2H, s), 6.84-6.88 (1H, m), 7.41 (1H, dd, J = 1.7, 8.6 Hz), 7.54-7.59 (2H, m), 7.76 (1H, d, J = 5.8 Hz), 8.09 (1H, t, J = 2.2 Hz), 8.11 (1H, d, J = 2.4 Hz), 8.14 (1H, d, J = 8.6 Hz), 8.67 (1H, d, J = 2.1 Hz), 8.93 (1H, d, J = 2.1 Hz), 9.28 (1H, t, J = 6.0 Hz) |
| 71 | 1.70 (1H, m), 1.98 (1H, m), 2.37 (1H, m), 3.10 (1H, dd J = 6.4, 10.4 Hz), 3.25-3.30 (1H, m), 3.35-3.47 (4H, m), 3.88 (2H, s), 4.61 (2H, d, J = 5.9 Hz), 4.66 (1H, t, J = 5.2 Hz), 6.36 (1H, d, J = 8.6 Hz), 6.77 (2H, s), 6.87 (1H, d, J = 5.8 Hz), 7.36 (1H, dd, J = 2.4, 8.6 Hz), 7.41 (1H, dd, J = 1.7, 8.6 Hz), 7.57 (1H, d, J = 1.7 Hz), 7.75 (1H, d, J = 5.8 Hz), 8.00-8.07 (2H, m), 8.15 (1H, d, J = 8.6 Hz), 8.63 (1H, d, J = 2.1 Hz), 8.91 (1H, d, J = 2.1 Hz), 9.28 (1H, t, J = 5.9H) |
| 72 | 1.19 (3H, t J = 7.1 Hz), 2.06-2.16 (1H, m), 2.16-2.25 (1H, m), 3.19-3.27 (1H, m), 3.36-3.46 (2H, m), 3.51 (1H, dd, J = 6.2, 10.5 Hz), 3.60 (1H, dd, J = 7.9, 10.5 Hz), 3.89 (2H, s), 4.09 (2H, q, J = 7.1 Hz), 4.61 (2H, d, J = 5.8 Hz), 6.42 (1H, d, J = 8.6 Hz), 6.71 (2H, s), 6.86 (1H, d, J = 5.8 Hz), 7.39 (2H, ddd, J = 2.1, 7.2, 8.9 Hz), 7.56 (1H, d, J = 1.7 Hz), 7.76 (1H, d, J = 5.8 Hz), 8.00-8.09 (2H, m), 8.13 (1H, d, J = 8.6 Hz), 8.63 (1H, d, J = 2.1 Hz), 8.91 (1H, d, J = 2.1 Hz), 9.28 (1H, t, J = 5.9 Hz) |
| 73 | 1.07 (6H, d, J = 6.7 Hz), 2.74 (3H, s), 3.88 (2H, s), 4.62 (2H, d, J = 5.9 Hz), 4.78 (1H, p, J = 6.7 Hz), 6.55 (1H, d, J = 8.8 Hz), 6.91 (1H, d, J = 6.0 Hz), 6.98 (2H, s), 7.37 (1H, dd, J = 2.5, 8.8 Hz), 7.44 (1H, dd, J = 1.8, 8.7 Hz), 7.59 (1H, d, J = 1.8 Hz), 7.74 (1H, d, J = 5.9 Hz), 8.01-8.09 (2H, m), 8.18 (1H, d, J = 8.6 Hz), 8.64 (1H, d, J = 2.1 Hz), 8.91 (1H, d, J = 2.1 Hz), 9.30 (1H, t, J = 5.9 Hz) |
| 74 | 1.07 (6H, d, J = 3.3 Hz); 1.72 (2H, t, J = 7.1 Hz); 3.11 (1H, s); 3.21-3.27 (1H, m); 3.40 (2H, t, J = 7.0 Hz); 3.87 (2H, s); 4.61 (2H, d, J = 5.9 Hz); 6.34 (1H, d, J = 8.6 Hz); 6.81 (2H, s); 6.88 (1H, d, J = 5.8 Hz); 7.35 (1H, dd, J = 2.5 & 8.6 Hz); 7.42 (1H, dd, J = 1.8 & 8.6 Hz); 7.57 (1H, d, J = 1.7 Hz); 7.75 (1H, d, J = 5.9 Hz); 7.98-8.09 (2H, m); 8.15 (1H, d, J = 8.6 Hz); 8.63 (1H, d, J = 2.1 Hz); 8.91 (1H, d, J = 2.1 Hz); 9.29 (1H, t, J = 5.9 Hz). |
| 75 | 2.07-2.22 (2H, m), 3.11-3.18 (1H, m), 3.36-3.45 (2H, m), 3.48-3.59 (2H, m), 3.89 (2H, s), 4.63 (2H, d, J = 5.8 Hz), 6.41 (1H, d, J = 8.6 Hz), 6.97 (1H, d, J = 6.2 Hz), 7.29 (2H, s), 7.38 (1H, d, J = 10.9 Hz), 7.49 (1H, d, J = 8.4 Hz), 7.64 (1H, s), 7.73 (1H, d, J = 6.1 Hz), 8.04 (2H, s), 8.23 (1H, d, J = 8.6 Hz), 8.64 (1H, d, J = 2.0 Hz), 8.91 (1H, d, J = 2.0 Hz), 9.31 (1H, t, J = 5.9 Hz), 12.46 (1H, s) |
| 76 | 1.96-2.07 (2H, m), 2.54 (2H, t, J = 8.0 Hz), 3.95 (2H, t, J = 7.1 Hz), 4.10 (2H, s), 4.61 (2H, d, J = 5.8 Hz), 6.72 (2H, s), 6.87 (1H, d, J = 5.9 Hz), 7.05 (1H, dd, J = 1.5, 5.2 Hz), 7.41 (1H, dd, J = 1.8, 8.6 Hz), 7.56 (1H, s), 7.76 (1H, d, J = 5.8 Hz), 8.09 (1H, t, J = 2.2 Hz), 8.13 (1H, d, J = 8.6 Hz), 8.21 (1H, s), 8.29 (1H, ds, J = 0.8, 5.1 Hz), 8.67 (1H, d, J = 2.1 Hz), 8.96 (1H, d, J = 2.1 Hz), 9.31 (1H, t, J = 5.9 Hz). |
| 78 | 1.45-1.64 (6H, m), 3.45-3.50 (4H, m), 3.93 (2H, s), 4.62 (2H, d, J = 5.8 Hz), 6.46 (1H, dd, J = 1.2, 5.1 Hz), 6.71 (2H, s), 6.77 (1H, s), 6.86 (1H, d, J = 5.9 Hz), 7.41 (1H, dd, J = 1.7, 8.6 Hz), 7.57 (1H, s), 7.76 (1H, d, J = 5.8 Hz), 7.97 (1H, d, J = 5.1 Hz), 8.09-8.16 (2H, m), 8.68 (1H, d, J = 2.1 Hz), 8.94 (1H, d, J = 2.1 Hz), 9.29 (1H, t, J = 5.9 Hz). |
| 79 | 1.11 (3H, d, J = 6.2 Hz), 1.57-1.69 (1H, m), 1.86-2.05 (3H, m), 3.16-3.26 (1H, m), 3.38-3.46 (1H, m), 3.93 (2H, s), 4.04-4.13 (1H, m), 4.62 (2H, d, J = 5.8 Hz), 6.36 (1H, s), 6.40 (1H, dd, J = 5.2, 1.3 Hz), 6.74 (2H, s), 6.86 (1H, d, J = 5.8 Hz), 7.41 (1H, dd, J = 8.7, 1.7 Hz), 7.57 (1H, d, J = 1.7 Hz), 7.76 (1H, d, J = 5.8 Hz), 7.94 (1H, d, J = 5.1 Hz), 8.09-8.16 (2H, m), 8.68 (1H, d, J = 2.1 Hz), 8.94 (1H, d, J = 2.1 Hz), 9.30 (1H, t, J = 5.9 Hz) |
| 80 | 2.44-2.58 (2H, m), 3.58 (2H, t, J = 7.3 Hz), 3.80 (2H, t, J = 13.2 Hz), 3.96 (2H, s), 4.62 (2H, d, J = 5.8 Hz), 6.52 (1H, s), 6.56 (1H, dd, J = 5.1, 1.3 Hz), 6.79 (2H, s), 6.87 (1H, d, J = 5.8 Hz), 7.41 (1H, dd, J = 8.6, 1.7 Hz), 7.58 (1H, d, J = 1.7 Hz), |

TABLE 11-continued

<sup>1</sup>H NMR data of examples (solvent d6-DMSO)

| Example No | Chemical Shift (ppm) |
|---|---|
|  | 7.75 (1H, d, J = 5.8 Hz), 8.00 (1H, d, J = 5.1 Hz), 8.11 (1H, t, J = 2.2 Hz), 8.15 (1H, d, J = 8.6 Hz), 8.68 (1H, d, J = 2.1 Hz), 8.94 (1H, d, J = 2.1 Hz), 9.30 (1H, t, J = 5.9 Hz). |
| 81 | 1.81-1.91 (1H, m), 1.93-2.05 (1H, m), 3.23-3.29 (1H, m), 3.37-3.48 (3H, m), 3.93 (2H, s), 4.32-4.40 (1H, m), 4.62 (2H, d, J = 5.8 Hz), 4.91 (1H, d, J = 3.7 Hz), 6.36 (1H, s), 6.41 (1H, dd, J = 5.2, 1.3 Hz), 6.91 (1H, d, J = 6.0 Hz), 7.02 (2H, s), 7.45 (1H, dd, J = 8.6, 1.7 Hz), 7.61 (1H, d, J = 1.7 Hz), 7.74 (1H, d, J = 6.0 Hz), 7.94 (1H, d, J = 5.1 Hz), 8.10 (1H, t, J = 2.1 Hz), 8.19 (1H, d, J = 8.6 Hz), 8.68 (1H, d, J = 2.1 Hz), 8.94 (1H, d, J = 2.1 Hz), 9.31 (1H, t, J = 5.9 Hz). |
| 82 | 2.05-2.30 (2H, m), 3.35-3.44 (1H, m), 3.48-3.76 (3H, m), 3.96 (2H, s), 4.63 (2H, d, J = 5.8 Hz), 5.43 (1H, d, J = 54.3 Hz), 6.45 (1H, s), 6.48 (1H, dd, J = 5.4, 1.4 Hz), 6.79 (2H, s), 6.88 (1H, d, J = 6.0 Hz), 7.43 (1H, dd, J = 8.6, 1.7 Hz), 7.58 (1H, d, J = 1.7 Hz), 7.76 (1H, d, J = 5.8 Hz), 7.98 (1H, d, J = 5.2 Hz), 8.12 (1H, t, J = 2.2 Hz), 8.15 (1H, d, J = 8.6 Hz), 8.69 (1H, d, J = 2.1 Hz), 8.95 (1H, d, J = 2.1 Hz), 9.31 (1H, t, J = 5.9 Hz) |
| 83 | 1.05 (3H, d, J = 6.6 Hz), 1.46-1.61 (1H, m), 2.00-2.11 (1H, m), 2.24-2.37 (1H, m), 2.87 (1H, dd, J = 10.1, 7.6 Hz), 3.26-3.33 (1H, m), 3.41-3.51 (1H, m), 3.54 (1H, dd, J = 10.1, 7.2 Hz), 3.92 (2H, s), 4.62 (2H, d, J = 5.8 Hz), 6.34 (1H, s), 6.40 (1H, dd, J = 5.2, 1.3 Hz), 6.82 (2H, s), 6.88 (1H, d, J = 6.0 Hz), 7.42 (1H, dd, J = 8.6, 1.8 Hz), 7.58 (1H, d, J = 1.7 Hz), 7.75 (1H, d, J = 5.9 Hz), 7.93 (1H, d, J = 5.2 Hz), 8.10 (1H, t, J = 2.1 Hz), 8.15 (1H, d, J = 8.6 Hz), 8.67 (1H, d, J = 2.1 Hz), 8.94 (1H, d, J = 2.1 Hz), 9.30 (1H, t, J = 5.9 Hz). |
| 84 | 1.44 (6H, s), 1.79-1.90 (4H, m), 3.30-3.34 (2H, m), 3.91 (2H, s), 4.62 (2H, d, J = 5.8 Hz), 6.32 (1H, s), 6.38 (1H, dd, J = 5.1, 1.3 Hz), 6.82 (2H, s), 6.87 (1H, d, J = 5.8 Hz), 7.42 (1H, dd, J = 8.6, 1.7 Hz), 7.58 (1H, s), 7.75 (1H, d, J = 5.9 Hz), 7.93 (1H, d, J = 5.1 Hz), 8.12 (1H, t, J = 2.2 Hz), 8.15 (1H, d, J = 8.6 Hz), 8.68 (1H, d, J = 2.1 Hz), 8.94 (1H, d, J = 2.1 Hz), 9.30 (1H, t, J = 5.9 Hz). |
| 85 | 3.38-3.45 (4H, m), 3.63-3.71 (4H, m), 3.96 (2H, s), 4.62 (2H, d, J = 5.8 Hz), 6.57 (1H, dd, J = 5.1, 1.2 Hz), 6.77-6.93 (4H, m), 7.43 (1H, dd, J = 8.6, 1.7 Hz), 7.58 (1H, s), 7.75 (1H, d, J = 5.8 Hz), 8.02 (1H, d, J = 5.1 Hz), 8.11 (1H, t, J = 2.2 Hz), 8.16 (1H, d, J = 8.5 Hz), 8.68 (1H, d, J = 2.1 Hz), 8.94 (1H, d, J = 2.1 Hz), 9.30 (1H, t, J = 5.9 Hz) |
| 86 | 2.23 (3H, s), 2.37-2.45 (4H, m), 3.41-3.52 (4H, m), 3.94 (2H, s), 4.62 (2H, d, J = 5.8 Hz), 6.53 (1H, dd, J = 5.1, 1.2 Hz), 6.75 (2H, s), 6.80 (1H, s), 6.87 (1H, d, J = 5.9 Hz), 7.41 (1H, dd, J = 8.6, 1.7 Hz), 7.57 (1H, s), 7.76 (1H, d, J = 5.8 Hz), 8.00 (1H, d, J = 5.1 Hz), 8.11 (1H, t, J = 2.2 Hz), 8.14 (1H, d, J = 8.6 Hz), 8.68 (1H, d, J = 2.1 Hz), 8.94 (1H, d, J = 2.1 Hz), 9.29 (1H, t, J = 5.9 Hz). |
| 87 | 1.06 (6H, t, J = 6.9 Hz), 3.45 (4H, q, J = 7.0 Hz), 3.92 (2H, s), 4.62 (2H, d, J = 5.8 Hz), 6.37 (1H, s), 6.50 (1H, s), 6.71 (2H, s), 6.86 (1H, d, J = 5.9 Hz), 7.41 (1H, dd, J = 8.6, 1.8 Hz), 7.56 (1H, s), 7.76 (1H, d, J = 5.8 Hz), 7.93 (1H, d, J = 5.0 Hz), 8.10-8.16 (2H, m), 8.68 (1H, d, J = 2.1 Hz), 8.94 (1H, d, J = 2.1 Hz), 9.29 (1H, t, J = 5.9 Hz). |
| 88 | 1.98-2.07 (2H, m), 3.24 (3H, s), 3.28-3.47 (4H, m), 3.93 (2H, s), 4.01-4.08 (1H, m), 4.62 (2H, d, J = 5.8 Hz), 6.39 (1H, s), 6.43 (1H, dd, J = 5.2, 1.3 Hz), 6.84-7.03 (3H, m), 7.44 (1H, dd, J = 8.7, 1.7 Hz), 7.59 (1H, s), 7.75 (1H, d, J = 5.9 Hz), 7.95 (1H, d, J = 5.1 Hz), 8.11 (1H, t, J = 2.2 Hz), 8.17 (1H, d, J = 8.6 Hz), 8.68 (1H, d, J = 2.1 Hz), 8.94 (1H, d, J = 2.1 Hz), 9.30 (1H, t, J = 5.9 Hz). |
| 89 | 1.77-2.01 (4H, m), 3.11-3.29 (2H, m), 3.35-3.44 (1H, m), 3.50-3.59 (1H, m), 3.93 (2H, s), 3.97-4.07 (1H, m), 4.62 (2H, d, J = 5.8 Hz), 4.90 (1H, t, J = 5.7 Hz), 6.40-6.47 (2H, m), 6.71 (2H, s), 6.86 (1H, d, J = 5.8 Hz), 7.41 (1H, dd, J = 8.6, 1.7 Hz), 7.57 (1H, s), 7.76 (1H, d, J = 5.8 Hz), 7.94 (1H, d, J = 5.9 Hz), 8.07-8.19 (2H, m), 8.68 (1H, d, J = 2.1 Hz), 8.94 (1H, d, J = 2.1 Hz), 9.29 (1H, t, J = 5.9 Hz). |
| 90 | 1.75-1.88 (1H, m), 2.11-2.21 (1H, m), 2.27 (6H, s), 2.84-2.94 (1H, m), 3.09-3.16 (1H, m), 3.26-3.32 (1H, m), 3.50-3.58 (1H, m), 3.62-3.71 (1H, m), 3.93 (2H, s), 4.62 (2H, d, J = 5.8 Hz), 6.39-6.47 (2H, m), 6.79 (2H, s), 6.87 (1H, d, J = 5.9 Hz), 7.42 (1H, dd, J = 8.6, 1.7 Hz), 7.57 (1H, s), 7.76 (1H, d, J = 5.8 Hz), 7.95 (1H, d, J = 5.1 Hz), 8.10 (1H, t, J = 2.2 Hz), 8.15 (1H, d, J = 8.6 Hz), 8.68 (1H, d, J = 2.1 Hz), 8.94 (1H, d, J = 2.1 Hz), 9.29 (1H, t, J = 5.9 Hz). |
| 91 | 1.75-1.88 (1H, m), 2.11-2.21 (1H, m), 2.28 (6H, s), 2.84-2.94 (1H, m), 3.09-3.16 (1H, m), 3.26-3.32 (1H, m), 3.50-3.58 (1H, m), 3.62-3.71 (1H, m), 3.93 (2H, s), 4.62 (2H, d, J = 5.8 Hz), 6.39-6.47 (2H, m), 6.79 (2H, m), 6.87 (1H, d, J = 5.9 Hz), 7.42 (1H, dd, J = 8.6, 1.7 Hz), 7.57 (1H, s), 7.76 (1H, d, J = 5.8 Hz), 7.95 (1H, d, J = 5.1 Hz), 8.10 (1H, t, J = 2.2 Hz), 8.15 (1H, d, J = 8.6 Hz), 8.68 (1H, d, J = 2.1 Hz), 8.94 (1H, d, J = 2.1 Hz), 9.29 (1H, t, J = 5.9 Hz). |
| 92 | 1.65-1.76 (1H, m), 1.93-2.04 (1H, m), 2.34-2.43 (1H, m), 3.07-3.15 (1H, m), 3.30-3.50 (5H, m), 3.93 (2H, s), 4.62 (2H, d, J = 5.9 Hz), 4.67 (1H, t, J = 5.2 Hz), 6.36 (1H, s), 6.41 (1H, dd, J = 5.2, 1.4 Hz), 6.84-6.94 (3H, m), 7.44 (1H, dd, J = 8.7, 1.8 Hz), 7.59 (1H, s), 7.75 (1H, d, J = 5.8 Hz), 7.94 (1H, d, J = 5.1 Hz), 8.10 (1H, t, J = 2.2 Hz), 8.17 (1H, d, J = 8.6 Hz), 8.68 (1H, d, J = 2.1 Hz), 8.94 (1H, d, J = 2.1 Hz), 9.30 (1H, t, J = 6.0 Hz). |
| 93 | 1.98 (3H, s), 2.30 (3H, s), 3.18 (2H, br s), 3.65 (2H, s), 4.00 (2H, s), 4.42 (2H, d, J = 5.6 Hz), 5.19 (2H, s), 7.02-7.19 (5H, m), 7.22 (2H, s), 7.24 (1H, s), 7.52 (1H, s), 8.04 (1H, d, J = 2.0 Hz), 8.62 (1H, d, J = 2.0 Hz), 8.88 (1H, d, J = 2.0 Hz), 9.01 (1H, t, J = 5.5 Hz). |
| 94 | 2.04 (3H, s), 2.38 (6H, s), 3.24 (2H, br s), 3.70 (2H, s), 4.03 (2H, s), 4.50 (2H, d, J = 4.7 Hz), 5.24 (2H, s), 7.04 (2H, s), 7.18 (2H, d, J = 8.1 Hz), 7.26 (1H, s), 7.28 (2H, s), |

TABLE 11-continued

<sup>1</sup>H NMR data of examples (solvent d6-DMSO)

| Example No | Chemical Shift (ppm) |
|---|---|
|  | 7.57 (1H, s), 8.05 (1H, t, J = 2.0 Hz), 8.63 (1H, d, J = 2.0 Hz), 8.66 (1H, t, J = 4.6 Hz), 8.86 (1H, d, J = 2.0 Hz). |
| 95 | 1.98 (3H, s), 2.34 (6H, s), 3.62 (2H, s), 4.16 (2H, s), 4.51 (2H, d, J = 5.6 Hz), 5.18 (2H, s), 6.98 (2H, s), 7.11 (2H, d, J = 8.0 Hz), 7.23 (1H, s), 7.27 (2H, d, J = 8.1 Hz), 7.51 (1H, s), 8.48 (1H br.s), 8.76 (1H, s), 8.98 (1H, s). |
| 96 | 1.98 (3H, s), 2.70-3.20 (2H, br s), 3.72 (2H, s), 4.00 (2H, s), 4.44 (2H, d, J = 5.6 Hz), 5.18 (2H, s), 7.04-7.14 (4H, m), 7.22-7.24 (3H, m), 7.41 (1H, dd, J = 8.0, 8.0 Hz), 7.51 (1H, s), 8.03 (1H, s), 8.62 (1H, d, J = 2.0 Hz), 8.87 (1H, d, J = 2.0 Hz), 9.19 (1H, t, J = 5.6 Hz). |

Biological Methods

The ability of the compounds of formula (I) to inhibit plasma kallikrein may be determined using the following biological assays:

Determination of the $IC_{50}$ Plasma Kallikrein

Plasma kallikrein inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human plasma kallikrein (Protogen) was incubated at 37° C. with the fluorogenic substrate H-DPro-Phe-Arg-AFC and various concentrations of the test compound. Residual enzyme activity (initial rate of reaction) was determined by measuring the change in optical absorbance at 410 nm and the $IC_{50}$ value for the test compound was determined.

Data acquired from these assays are shown in Table 12 below. Generally, but not exclusively, preferred compounds demonstrate an $IC_{50}$ of less than 200 nM.

TABLE 12

| Example No | IC50 (human PKal) nM |
|---|---|
| 1 | 3.86 |
| 2 | 216 |
| 3 | 159 |
| 4 | 6610 |
| 5 | 24.7 |
| 6 | 580 |
| 7 | 35.3 |
| 8 | 119 |
| 9 | 30.8 |
| 10 | 194 |
| 11 | 82.3 |
| 12 | 244 |
| 13 | 923 |
| 14 | 2670 |
| 15 | 159 |
| 16 | 179 |
| 17 | 27.5 |
| 18 | 702 |
| 19 | 434 |
| 20 | 621 |
| 21 | 53.3 |
| 22 | 104 |
| 23 | 40000 |
| 24 | 1710 |
| 25 | 2640 |
| 26 | 941 |
| 27 | 1010 |
| 28 | 1100 |
| 29 | 20200 |
| 30 | 302 |
| 31 | 144 |
| 32 | 237 |
| 33 | 17.1 |
| 34 | 1020 |
| 35 | 3510 |
| 36 | 6650 |
| 37 | 1180 |
| 38 | 107 |
| 39 | 10000 |
| 40 | 127 |
| 41 | 2750 |
| 42 | 1830 |
| 43 | 11000 |
| 44 | 6790 |
| 45 | 33600 |
| 46 | 7510 |
| 47 | 40000 |
| 48 | 21900 |
| 49 | 6990 |
| 50 | 10000 |
| 51 | 8110 |
| 52 | 10000 |
| 53 | 200 |
| 54 | 14600 |
| 55 | 103 |
| 56 | 313 |
| 57 | 240 |
| 58 | 153 |
| 59 | 417 |
| 60 | 137 |
| 61 | 137 |
| 62 | 255 |
| 63 | 432 |
| 64 | 610 |
| 65 | 131 |
| 66 | 52.7 |
| 67 | 73.3 |
| 68 | 375 |
| 69 | 579 |
| 70 | 1740 |
| 71 | 306 |
| 72 | 860 |
| 73 | 51.1 |
| 74 | 83.1 |
| 75 | 6120 |
| 76 | 242 |
| 77 | 37.7 |
| 78 | 164 |
| 79 | 155 |
| 80 | 88.5 |
| 81 | 674 |
| 82 | 67.8 |
| 83 | 106 |
| 84 | 683 |
| 85 | 1670 |
| 86 | 395 |
| 87 | 358 |
| 88 | 234 |
| 89 | 104 |
| 90 | 1550 |
| 91 | 1710 |
| 92 | 355 |

TABLE 12-continued

| Example No | IC50 (human PKal) nM |
|---|---|
| 93 | 14.4 |
| 94 | 7.47 |
| 95 | 53.6 |
| 96 | 365 |

Selected compounds were further screened for inhibitory activity against the related enzyme KLK1. The ability of the compounds of formula (I) to inhibit KLK1 may be determined using the following biological assay:

Determination of the $IC_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human KLK1 (Callbiochem) was incubated at 37° C. with the fluorogenic substrate H-DVal-Leu-Arg-AFC and various concentrations of the test compound. Residual enzyme activity (initial rate of reaction) was determined by measuring the change in optical absorbance at 410 nm and the $IC_{50}$ value for the test compound was determined.

Data acquired from this assay are shown in Table 13 below:

TABLE 13

| Example No | IC50 (human KLK1) nM |
|---|---|
| 1 | >10,000 |
| 2 | >10,000 |
| 3 | >40,000 |
| 4 | >40,000 |
| 5 | 28900 |
| 6 | 27800 |
| 7 | 8020 |
| 8 | 28200 |
| 9 | 5340 |
| 10 | 3020 |
| 11 | 37100 |
| 12 | 14900 |
| 13 | 236 |
| 14 | 4160 |
| 15 | 17600 |
| 16 | 2060 |
| 17 | 1120 |
| 18 | 1740 |
| 19 | 1210 |
| 20 | 2490 |
| 21 | 5990 |
| 22 | 484 |
| 23 | 32700 |
| 24 | 4000 |
| 25 | 6170 |
| 26 | >40,000 |
| 27 | 12100 |
| 28 | 5900 |
| 29 | 7350 |
| 30 | 2850 |
| 31 | 4130 |
| 32 | 9530 |
| 33 | 17100 |
| 34 | >40,000 |
| 35 | 29800 |
| 36 | 23800 |
| 37 | 29100 |
| 38 | 8600 |
| 39 | >10,000 |
| 40 | 4870 |
| 41 | 37000 |
| 42 | 24300 |
| 43 | 17900 |
| 44 | 28000 |

TABLE 13-continued

| Example No | IC50 (human KLK1) nM |
|---|---|
| 45 | 26900 |
| 46 | 29200 |
| 47 | >40,000 |
| 48 | >40,000 |
| 49 | >10,000 |
| 50 | >10,000 |
| 51 | >10,000 |
| 52 | >10,000 |
| 53 | 3860 |
| 54 | 10700 |
| 55 | 4960 |
| 56 | >40,000 |
| 57 | >40,000 |
| 58 | 6520 |
| 59 | 6010 |
| 60 | 8690 |
| 61 | 6550 |
| 62 | 8890 |
| 63 | >10,000 |
| 64 | 5340 |
| 65 | >10,000 |
| 66 | 5850 |
| 67 | 5150 |
| 68 | 3510 |
| 69 | 2430 |
| 70 | >10,000 |
| 71 | 3950 |
| 72 | 3620 |
| 73 | 6690 |
| 74 | >10,000 |
| 75 | >10,000 |
| 76 | 3750 |
| 77 | 4800 |
| 78 | 6930 |
| 79 | 7140 |
| 80 | 7550 |
| 81 | 9570 |
| 82 | 4000 |
| 83 | 2870 |
| 84 | 10700 |
| 85 | 8540 |
| 86 | 4460 |
| 87 | 4980 |
| 88 | 9850 |
| 89 | 4840 |
| 90 | 3880 |
| 91 | 2110 |
| 92 | 7510 |
| 93 | >40,000 |
| 94 | >40,000 |
| 95 | >40,000 |
| 96 | >40,000 |

The invention claimed is:

1. A compound of formula I:

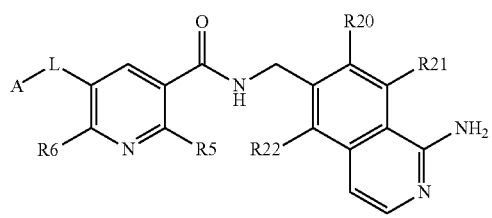

wherein:

R5 and R6 are, independently, H, $CH_3$, $OCH_3$, OH, or —$NHCH_3$;

A is aryl, heteroaryl, or a substituent group which is formula (A), (B), (C), or (D):

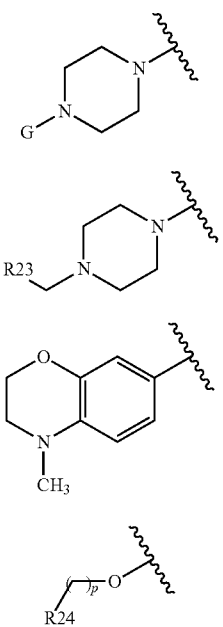

Formula (A)

Formula (B)

Formula (C)

Formula (D)

wherein:
G is H, alkyl, cycloalkyl, CO-aryl, SO$_2$-aryl, (CH$_2$)$_m$-aryl, or (CH$_2$)$_m$-heteroaryl;
m is 0 or 1;
p is 0, 1, 2, or 3;
R23 is aryl or heteroaryl;
R24 is aryl or heteroaryl;
L is a linker which is —CH$_2$— or —(CHOH)—;
R20, R21, and R22 are H;
alkyl is a C$_1$-C$_{10}$ linear saturated hydrocarbon or a C$_3$-C$_{10}$ branched saturated hydrocarbon;
  alkyl is optionally substituted with 1 or 2 independent substituents which are (C$_1$-C$_6$)alkoxy, OH, CN, CF$_3$, COOR10, CONR10R11, fluoro, phenyl, or NR10R11;
cycloalkyl is a C$_3$-C$_7$ monocyclic saturated hydrocarbon;
a cyclic ether is a monocyclic saturated hydrocarbon of between 4 and 7 carbon atoms, wherein one of the ring carbons is replaced by an oxygen atom;
alkoxy is a C$_1$-C$_6$ linear O-linked hydrocarbon or a C$_3$-C$_6$ branched O-linked hydrocarbon;
  alkoxy is optionally substituted with 1 or 2 independent substituents which are OH, OCH$_3$, CN, CF$_3$, COOR10, CONR10R11, fluoro, or NR10R11;
aryl is phenyl, biphenyl, or naphthyl; each aryl being optionally substituted with 1, 2, or 3 substituents which are independently alkyl, alkoxy, methylenedioxy, ethylenedioxy, OH, halo, CN, morpholinyl, piperidinyl, heteroaryl, —(CH$_2$)$_{0-3}$—O-heteroaryl, aryl$^b$, —O-aryl$^b$, —(CH$_2$)$_{1-3}$-aryl$^b$, —(CH$_2$)$_{1-3}$-heteroaryl, —COOR10, —CONR10R11, —(CH$_2$)$_{1-3}$—NR14R15, CF$_3$, or —NR10R11;
aryl$^b$ is phenyl, biphenyl, or naphthyl, which is optionally substituted with 1, 2, or 3 substituents which are independently alkyl, alkoxy, OH, halo, CN, morpholinyl, piperidinyl, —COOR10, —CONR10R11, CF$_3$, or NR10R11;
heteroaryl is a 5, 6, 9, or 10 membered mono- or bi-cyclic aromatic ring, independently containing 1, 2, or 3 ring members which are N, NR8, S, or O; heteroaryl is optionally independently substituted with 1, 2, or 3 substituents which are alkyl, alkoxy, OH, halo, CN, aryl, morpholinyl, piperidinyl, —(CH$_2$)$_{1-3}$-aryl, heteroaryl$^b$, —COOR10, —CONR10R11, CF$_3$, or —NR10R11;
heteroaryl$^b$ is a 5, 6, 9, or 10 membered mono- or bi-cyclic aromatic ring, independently containing 1, 2, or 3 ring members which are N, NR8, S, or O; wherein heteroaryl$^b$ is optionally independently substituted with 1, 2, or 3 substituents which are alkyl, alkoxy, OH, halo, CN, morpholinyl, piperidinyl, aryl, —(CH$_2$)$_{1-3}$-aryl, —COOR10, —CONR10R11, CF$_3$, or NR10R11;
R8 is H or alkyl;
R10 and R11 are, independently, H or alkyl; or R10 and R11 together with the nitrogen to which they are attached form a 4-, 5-, 6-, or 7-membered heterocyclic ring which is saturated or unsaturated with 1 or 2 double bonds and is optionally mono- or di-substituted with substituents which are oxo, alkyl, alkoxy, COOR8, OH, F, or CF$_3$;
R14 and R15 are independently alkyl, aryl$^b$ or heteroaryl$^b$; or R14 and R15 together with the nitrogen to which they are attached form a 4-, 5-, 6-, or 7-membered heterocyclic ring which is saturated or unsaturated with 1 or 2 double bonds, and optionally is oxo substituted;
or a tautomer, stereoisomer, or pharmaceutically acceptable salt solvate thereof.

2. A compound according to claim 1 wherein L is —CH$_2$—.

3. A compound according to claim 1 wherein A is heteroaryl substituted by optionally substituted phenyl or phenyl substituted by heteroaryl, —(CH$_2$)$_{1-3}$-heteroaryl, or —(CH$_2$)$_{1-3}$—NR14R15.

4. A compound according to claim 1 wherein A is:

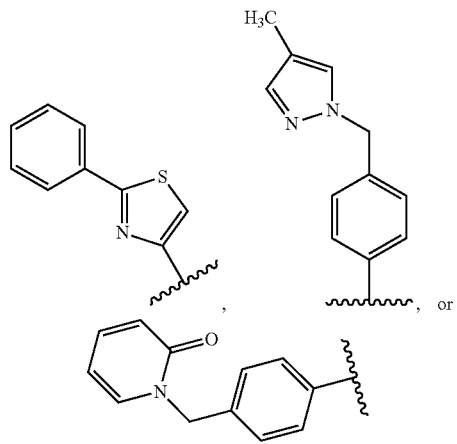

5. A compound according to claim 1, which is:
N-[(1-Aminoisoquinolin-6-yl)methyl]-5-({4-[(4-methyl-pyrazol-1-yl)methyl]phenyl}methyl) pyridine-3-carboxamide;
N-((1-Aminoisoquinolin-6-yl)methyl)-5-(hydroxy(4-((4-methyl-1H-pyrazol-1-yl)methyl)phenyl)methyl)nicotinamide;
N-[(1-Aminoisoquinolin-6-yl)methyl]-5-[(2-methylquinolin-6-yl)methyl]pyridine-3-carboxamide;
N-[(1-Aminoisoquinolin-6-yl)methyl]-6-(methylamino)-5-[(2-methylquinolin-6-yl)methyl]pyridine-3-carboxamide;

N-[(1-Aminoisoquinolin-6-yl)methyl]-2-methyl-5-[(2-methylquinolin-6-yl)methyl]pyridine-3-carboxamide;
N-[(1-Aminoisoquinolin-6-yl)methyl]-5-(quinolin-6-ylmethyl)pyridine-3-carboxamide;
N-[(1-Aminoisoquinolin-6-yl)methyl]-5-({3-methoxy-4-[(4-methylpyrazol-1-yl)methyl]phenyl}methyl)pyridine-3-carboxamide;
N-[(1-Aminoisoquinolin-6-yl)methyl]-5-[(4-methyl-2,3-dihydro-1,4-benzoxazin-7-yl)methyl]pyridine-3-carboxamide;
N-[(1-Aminoisoquinolin-6-yl)methyl]-5-{[2-(4-methylpyrazol-1-yl)ethoxy]methyl}pyridine-3-carboxamide;
N-[(1-Aminoisoquinolin-6-yl)methyl]-5-{[6-(2-oxopyrrolidin-1-yl)pyridin-3-yl]methyl}pyridine-3-carboxamide;
N-[(1-Aminoisoquinolin-6-yl)methyl]-5-{[6-(pyrrolidin-1-yl)pyridin-3-yl]methyl}pyridine-3-carboxamide;
N-[(1-Aminoisoquinolin-6-yl)methyl]-5-{[6-(2-methylpyrrolidin-1-yl)pyridin-3-yl]methyl}pyridine-3-carboxamide;
N-[(1-Aminoisoquinolin-6-yl)methyl]-5-{[6-(3-fluoropyrrolidin-1-yl)pyridin-3-yl]methyl}pyridine-3-carboxamide;
N-[(1-Aminoisoquinolin-6-yl)methyl]-5-{[6-(3-methylpyrrolidin-1-yl)pyridin-3-yl]methyl}pyridine-3-carboxamide;
N-[(1-Aminoisoquinolin-6-yl)methyl]-5-{[6-(2,2-dimethylpyrrolidin-1-yl)pyridin-3-yl]methyl}pyridine-3-carboxamide;
N-[(1-Aminoisoquinolin-6-yl)methyl]-5-{[6-(diethylamino)pyridin-3-yl]methyl}pyridine-3-carboxamide;
N-[(1-Aminoisoquinolin-6-yl)methyl]-5-({6-[2-(hydroxymethyl)pyrrolidin-1-yl]pyridin-3-yl}methyl)pyridine-3-carboxamide;
N-[(1-Aminoisoquinolin-6-yl)methyl]-5-({6-[isopropyl(methyl)amino]pyridin-3-yl}methyl) pyridine-3-carboxamide;
N-[(1-Aminoisoquinolin-6-yl)methyl]-5-{[6-(3,3-dimethylpyrrolidin-1-yl)pyridin-3-yl]methyl}pyridine-3-carboxamide;
N-[(1-Aminoisoquinolin-6-yl)methyl]-5-{[2-(pyrrolidin-1-yl)pyridin-4-yl]methyl}pyridine-3-carboxamide;
N-[(1-Aminoisoquinolin-6-yl)methyl]-5-{[2-(piperidin-1-yl)pyridin-4-yl]methyl}pyridine-3-carboxamide;
N-[(1-Aminoisoquinolin-6-yl)methyl]-5-{[2-(2-methylpyrrolidin-1-yl)pyridin-4-yl]methyl}pyridine-3-carboxamide;
N-[(1-Aminoisoquinolin-6-yl)methyl]-5-{[2-(3,3-difluoropyrrolidin-1-yl)pyridin-4-yl]methyl}pyridine-3-carboxamide;
N-[(1-Aminoisoquinolin-6-yl)methyl]-5-{[2-(3-fluoropyrrolidin-1-yl)pyridin-4-yl]methyl}pyridine-3-carboxamide;
N-[(1-Aminoisoquinolin-6-yl)methyl]-5-{[2-(3-methylpyrrolidin-1-yl)pyridin-4-yl]methyl}pyridine-3-carboxamide;
N-[(1-Aminoisoquinolin-6-yl)methyl]-5-({2-[2-(hydroxymethyl)pyrrolidin-1-yl]pyridin-4-yl}methyl) pyridine-3-carboxamide;
or a pharmaceutically acceptable salt or solvate thereof.

6. A pharmaceutical composition comprising a compound of claim 1 and a pharmaceutically acceptable carrier, diluent or excipient.

7. A method of treating a disease or condition in which plasma kallikrein activity is implicated, comprising administering to a subject in need thereof a therapeutically effective amount of a compound of claim 1, wherein said disease or condition is impaired visual acuity, diabetic retinopathy, diabetic macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, blood coagulation during cardiopulmonary bypass surgery, or bleeding from post operative surgery.

8. The method of claim 7, wherein the disease or condition in which plasma kallikrein activity is implicated is retinal vascular permeability associated with diabetic retinopathy and diabetic macular edema.

9. A compound according to claim 1, wherein said stereoisomer is an enantiomer, diastereoisomer, or racemic or scalemic mixture thereof.

10. The method of claim 7, wherein the disease or condition in which plasma kallikrein activity is implicated is impaired visual acuity.

11. The method of claim 7, wherein the disease or condition in which plasma kallikrein activity is implicated is diabetic retinopathy.

12. The method of claim 7, wherein the disease or condition in which plasma kallikrein activity is implicated is diabetic macular edema.

13. The method of claim 7, wherein the disease or condition in which plasma kallikrein activity is implicated is hereditary angioedema.

14. The method of claim 7, wherein the disease or condition in which plasma kallikrein activity is implicated is diabetes.

15. The method of claim 7, wherein the disease or condition in which plasma kallikrein activity is implicated is pancreatitis.

16. The method of claim 7, wherein the disease or condition in which plasma kallikrein activity is implicated is cerebral haemorrhage.

17. The method of claim 7, wherein the disease or condition in which plasma kallikrein activity is implicated is nephropathy.

18. The method of claim 7, wherein the disease or condition in which plasma kallikrein activity is implicated is cardiomyopathy.

19. The method of claim 7, wherein the disease or condition in which plasma kallikrein activity is implicated is neuropathy.

20. The method of claim 7, wherein the disease or condition in which plasma kallikrein activity is implicated is inflammatory bowel disease or arthritis.

21. The method of claim 7, wherein the disease or condition in which plasma kallikrein activity is implicated is inflammation.

22. The method of claim 7, wherein the disease or condition in which plasma kallikrein activity is implicated is septic shock or hypotension.

23. The method of claim 7, wherein the disease or condition in which plasma kallikrein activity is implicated is cancer.

24. The method of claim 7, wherein the disease or condition in which plasma kallikrein activity is implicated is adult respiratory distress syndrome.

25. The method of claim 7, wherein the disease or condition in which plasma kallikrein activity is implicated is disseminated intravascular coagulation.

26. The method of claim 7, wherein the disease or condition in which plasma kallikrein activity is implicated is blood coagulation during cardiopulmonary bypass surgery.

27. The method of claim 7, wherein the disease or condition in which plasma kallikrein activity is implicated is bleeding from post-operative surgery.

28. A pharmaceutical composition comprising a compound of claim 5 and a pharmaceutically acceptable carrier, diluent or excipient.

29. A method of treating a disease or condition in which plasma kallikrein activity is implicated, comprising administering to a subject in need thereof a therapeutically effective amount of a compound of claim 5, wherein the disease or condition is impaired visual acuity, diabetic retinopathy, diabetic macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, blood coagulation during cardiopulmonary bypass surgery or bleeding from post operative surgery.

30. The method of claim 29, wherein the disease or condition in which plasma kallikrein activity is implicated is retinal vascular permeability associated with diabetic retinopathy and diabetic macular edema.

31. The method of claim 29, wherein the disease or condition in which plasma kallikrein activity is implicated is diabetic macular edema.

32. The method of claim 29, wherein the disease or condition in which plasma kallikrein activity is implicated is hereditary angioedema.

* * * * *